US007892566B2

(12) United States Patent
Hermon-Taylor et al.

(10) Patent No.: US 7,892,566 B2
(45) Date of Patent: Feb. 22, 2011

(54) IMMUNOGENIC CONSTRUCTS

(75) Inventors: John Hermon-Taylor, London (GB);
Timothy John Bull, London (GB)

(73) Assignee: HAV Vaccines Limited, Wimbledon, London (GB)

( * ) Notice: Subject to any disclaimer, the term of this patent is extended or adjusted under 35 U.S.C. 154(b) by 155 days.

(21) Appl. No.: 11/997,627

(22) PCT Filed: Aug. 3, 2006

(86) PCT No.: PCT/GB2006/002893

§ 371 (c)(1),
(2), (4) Date: Feb. 1, 2008

(87) PCT Pub. No.: WO2007/017635

PCT Pub. Date: Feb. 15, 2007

(65) Prior Publication Data

US 2009/0203593 A1    Aug. 13, 2009

Related U.S. Application Data

(60) Provisional application No. 60/706,594, filed on Aug. 9, 2005.

(51) Int. Cl.
*A61K 39/04* (2006.01)
(52) U.S. Cl. .............. 424/248.1; 424/185.1; 424/190.1; 424/192.1; 435/975
(58) Field of Classification Search ........................ None
See application file for complete search history.

(56) References Cited

U.S. PATENT DOCUMENTS

| 5,225,324 A | 7/1993 | McFadden et al. |
| 6,156,322 A | 12/2000 | Hermon-Taylor et al. |
| 7,541,181 B2 | 6/2009 | Hermon-Taylor et al. |

FOREIGN PATENT DOCUMENTS

| EP | 0 288 306 A1 | 10/1988 |
| FR | 2 682 967 | 4/1993 |
| NZ | 244 901 | 7/1995 |
| WO | WO 97/23624 | 7/1997 |
| WO | WO 99/49054 | 9/1999 |

OTHER PUBLICATIONS

Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Greenspan et al (Nature Biotechnology 7: 936-937, 1999).*
Chothia et al (The EMBO Journal, 1986, 5/4:823-26).*
Bull et al., "Further Studies on the GS Element. A Novel Mycobacterial Insertion Sequence (IS1612), Inserted into an Acetylase Gene (*mpa*) in *Mycobacterium avium* Subsp. *Silvaticum* but not in *Mycobacterium Avium* Subsp. *Paratuberculosis*," Vet. Microbiol. 77:453-463, 2000.

Gowzdz et al., "Vaccination Against Paratuberculosis of Lambs Already Infected Experimentally with *Mycobacterium avium* Subspecies *Paratuberculosis*," Aust. Vet. J. 78:560-566, 2000.
Hermon-Taylor, "Treatment with Drugs Active Against *Mycobacterium avium* Subspecies *Paratuberculosis* can Heal Crohn's Disease: More Evidence for a Neglected Public Health Tragedy," Dig. Liver. Dis. 34:9-12, 2002.
Hermon-Taylor et al., "Causation of Crohn's Disease by *Mycobacterium avium* Subspecies *Paratuberculosis*," Can. J. Gastroenterol. 14:521-539, 2000.
Tizard et al., "A Low G C Content Genetic Island in *Mycobacterium avium* Subsp. *Paratuberculosis* and *M. avium* Subsp. *Silvaticum* with Homologous Genes in *Mycobacterium tuberculosis*," Microbiol. 144:3413-3423, 1998.
International Search Report and Written Opinion from International Application No. PCT/GB2006/002893 dated Oct. 18, 2006.
U.S. Appl. No. 09/646,568, Hermon-Taylor et al.
Belisle et al., "Isolation and Expression of a Gene Cluster Responsible for Biosynthesis of the Glycopeptidolipid Antigens of *Mycobacterium avium*," J. Bacteriol. 173:6991-6997, 1991.
Belisle et al., "Rough Morphological Variants of *Mycobacterium avium*," J. Biol. Chem. 268:10517-10523, 1993.
Bull et al., "A Novel Multi-Antigen Virally Vectored Vaccine Against *Mycobacterium avium* Subspecies *Paratuberculosis*," PLoS One 11(e1229):1-14, 2007.

(Continued)

*Primary Examiner*—Jennifer E Graser
(74) *Attorney, Agent, or Firm*—Clark & Elbing LLP

(57) ABSTRACT

The present invention relates to molecules, which can be used to induce a therapeutic or prophylactic immune response against MAP. In particular, the present invention relates to polypeptides comprising an alipC polypeptide sequence, a gsd polypeptide sequence, a pl2 polypeptide sequence and an mpa polypeptide sequence, wherein said ahpC polypeptide comprises the sequence of SEQ ID NO: 2, a variant thereof having more than 70% amino acid sequence identity to SEQ ID NO: 2 across the full length of SEQ ID NO: 2, or a fragment of at least 8 amino acids of SEQ ID NO: 2 which comprises an epitope; said gsd polypeptide comprises the sequence of SEQ ID NO: 6, a variant thereof having more than 70% amino acid sequence identity to SEQ ID NO: 6 across the full length of SEQ ID NO: 6, or a fragment of at least 8 amino acids of SEQ ID NO: 6 which comprises an epitope; said pi 2 polypeptide comprises the sequence of SEQ ID NO: 10, a variant thereof having more than 70% amino acid sequence identity to SEQ ID NO: 10 across the full length of SEQ ID NO: 10, or a fragment of at least 8 amino acids of SEQ ID NO: 10 which comprises an epitope; and said mpa polypeptide comprises the sequence of SEQ ID NO: 14, a variant thereof having more than 70% amino acid sequence identity to SEQ ID NO: 14 across the full length of SEQ ID NO: 14, or a fragment of at least 8 amino acids of SEQ ID NO: 14 which comprises an epitope. Preferably such a variant maintains the ability to generate an immune response against the unmodified polypeptide.

22 Claims, 9 Drawing Sheets

OTHER PUBLICATIONS

Cousins et al., "Use of BACTEC Radiometric Culture Method and Polymerase Chain Reaction for the Rapid Screening of Faeces and Tissues for *Mycobacterium paratuberculosis*," Aust. Vet. J. 72:458-462, 1995.

Eckstein et al., "A Genetic Mechanism for Deletion of the *ser2* Gene Cluster and Formation of Rough Morphological Variants of *Mycobacterium avium*," J. Bacteriol. 182:6177-6182, 2000.

Eckstein et al., "Proposed Pathway for the Biosynthesis of Serovar-Specific Glycopeptidolipids in *Mycobacterium avium* Serovar 2," Microbiol. 149:2797-2807, 2003.

Khachaturyan et al., "Formation of Acylases by Hydrocarbon-Oxidizing Microorganisms," Chemical Abstracts, 74:20614, 1970.

Krzywinska et al., "Characterization of Genetic Differences Between *Mycobacterium avium* subsp. *Avium* Strains of Diverse Virulence with a Focus on the Glycopeptidolipid Biosynthesis Cluster," Vet. Microbiol. 91:249-264, 2003.

Mills et al., "Loci of *Mycobacterium avium ser2* Gene Cluster and Their Functions," J. Bacteriol. 176:4803-4808, 1994.

Sasaya et al., "Biological, Serological, and Molecular Variabilities of Clover Yellow Vein Virus," Phytopathol. 87:1014-1019, 1997.

Sheridan et al., "Use of Bioinformatics to Predict a Function for the GS Element in *Mycobacterium avium* Subspecies *Paratuberculosis*," J. Mol. Microbiol. Biotechnol. 5:57-66, 2003.

\* cited by examiner

```
TACCCGGGATATTCTGCAGTCACCGTATTTGACACGATGCAGATCTTCGT            50
                                   M  Q  I  F  V
CAAACTGCCCCTTCTCACTATCGGAGACCAGTTCCCCGCTTACGAACTTA           100
 K  L  P  L  L  T  I  G  D  Q  F  P  A  Y  E  L
CAGCTCTTATCGCTGGAGATCTGAGTAAGGTTGACGCCAAACAGCCCGGC           150
 T  A  L  I  A  G  D  L  S  K  V  D  A  K  Q  P  G
GATTATTTCACTACCGTTACCAGTGAGGATCACGCAGGTAAATGGAGAGT           200
 D  Y  F  T  T  V  T  S  E  D  H  A  G  K  W  R  V
CGTCTTCTTCTGGCCTAAAGACTTCACCTTTGTGTGCCCTACTGAGATCG           250
 V  F  F  W  P  K  D  F  T  F  V  C  P  T  E  I
CAACATTCGGGAAGCTGAACGATGAGTTCGAAGATCGAGACGCACAGGTT           300
 A  T  F  G  K  L  N  D  E  F  E  D  R  D  A  Q  V
TTGGGCGTGTCTATCGATTCCGAGTTCGTGCACTTCAACTGGAGAGCACA           350
 L  G  V  S  I  D  S  E  F  V  H  F  N  W  R  A  Q
GCATGAAGATCTCAAGAACCTTCCATTCCCCATGCTCAGCGACATCAAGA           400
 H  E  D  L  K  N  L  P  F  P  M  L  S  D  I  K
GAGAACTGAGCTTGGCAACAGGTGTTCTGAATGCTGATGGCGTTGCTGAC           450
 R  E  L  S  L  A  T  G  V  L  N  A  D  G  V  A  D
AGAGCAACATTCATTGTTGACCCCAATAACGAGATCCAGTTCGTTTCCGT           500
 R  A  T  F  I  V  D  P  N  N  E  I  Q  F  V  S  V
TACTGCTGGTTCTGTCGGTAGAAACGTTGAAGAGGTCCTGAGAGTTCTCG           550
 T  A  G  S  V  G  R  N  V  E  E  V  L  R  V  L
ACGCACTTCAGAGTGATGAACTGTGTGCCTGCAATTGGCGGAAAGGAGAT           600
 D  A  L  Q  S  D  E  L  C  A  C  N  W  R  K  G  D
CCTACTCTCAATGCCACAGAGCTGCTTAAAGCAAGTGCTCTCGGATCCAT           650
 P  T  L  N  A  T  E  L  L  K  A  S  A  L  G  S  I
TGTCGGACAGACCTATAGAGAGGTGGAAGTTGTCCTGGTCGATGGTGGAT           700
 V  G  Q  T  Y  R  E  V  E  V  V  L  V  D  G  G
CTACAGATAGGACTCTCGACATTGCCAACTCCTTTAGACCAGGAGCTCGGT          750
 S  T  D  R  T  L  D  I  A  N  S  F  R  P  E  L  G
TCAAGGCTCGTTGTTCATTCTGGACCAGATGATGGACCATACGACGCCAT           800
 S  R  L  V  V  H  S  G  P  D  D  G  P  Y  D  A  M
GAACAGAGGTGTTGGAGTTGCTACAGGAGAATGGGTCTTGTTCCTTGGAG           850
 N  R  G  V  G  V  A  T  G  E  W  V  L  F  L  G
CTGATGACACTCTGTACGAACCGACTACATTGGCTCAGGTTGCAGCATTT           900
 A  D  D  T  L  Y  E  P  T  T  L  A  Q  V  A  A  F
TTGGGAGATCATGCAGCTTCTCACCTTGTGTACGGAGATGTGGTCATGAG           950
 L  G  D  H  A  A  S  H  L  V  Y  G  D  V  V  M  R
ATCCACCAAGTCCAGACATGCTGGACCATTCGATCTTGACAGACTCCTGT          1000
 S  T  K  S  R  H  A  G  P  F  D  L  D  R  L  L
TCGAGACCAACCTCTGTCATCAGAGCATCTTCTACAGACGGGAACTCTTC          1050
 F  E  T  N  L  C  H  Q  S  I  F  Y  R  R  E  L  F
GACGGAATTGGACCTTACAACCTCAGGTACAGGGTTTGGGCAGACTGGGA          1100
 D  G  I  G  P  Y  N  L  R  Y  R  V  W  A  D  W  D
TTTCAACATCAGGTGCTTCTCGAACCCAGCTTTGATCACACGGTACATGG          1150
 F  N  I  R  C  F  S  N  P  A  L  I  T  R  Y  M
ATGTTGTGATCTCCGAGTACAACGATATGACCGGCTTCTCCATGAGACAG          1200
 D  V  V  I  S  E  Y  N  D  M  T  G  F  S  M  R  Q
GGAACCGACAAAGAGTTCAGGAAGCGCTTGCCAATGTACTTCTGGGTTGC          1250
 G  T  D  K  E  F  R  K  R  L  P  M  Y  F  W  V  A
TGGATGGGAAACATGTCGGAGAATGCTTGCTTTCCTGAAGGACAAGGAGA          1300
 G  W  E  T  C  R  R  M  L  A  F  L  K  D  K  E
ACAGGAGACTTGCTCTCAGGACTAGACTCATCAGGGTCAAAGCAGTGTCC          1350
 N  R  R  L  A  L  R  T  R  L  I  R  V  K  A  V  S
AAGGAAGGAGTGCTGAACCTAGAATTCGGAGACATAGACATGCAGAGAT           1400
 K  E  R  S  A  E  P  R  I  R  R  H  R  H  A  E  I
CATCCTGAGCATGCCTGGATTTGGCGTTATCCTCGGAGCTGAATTTCTTG          1450
 I  L  S  M  P  G  F  G  V  I  L  G  A  E  F  L
CAGCAACAGGAGGTGATATGGCAGCTTTCGCATCAGCTGACAGATTGGCT          1500
 A  A  T  G  G  D  M  A  A  F  A  S  A  D  R  L  A
GGAGTTGCAGGTTTTGGCTCCAGTTCCAAGAGATTCAGGGAGAATCAGCGG        1550
 G  V  A  G  L  A  P  V  P  R  D  S  G  R  I  S  G
TAACCTCAAGAGACCTAGACGCTACGACAGAAGACTGCTTAGAGCCTGCT         1600
 N  L  K  R  P  R  R  Y  D  R  R  L  L  R  A  C
ATCTGAGTGCTTTGGTTAGCATTAGAACCGACCCCTCTAGTCGAACCTAC         1650
 Y  L  S  A  L  V  S  I  R  T  D  P  S  S  R  T  Y
TACGATAGGAAGCGGACTGAAGGTAAGAGACATACCCAGGCAGTGTTGGC         1700
 Y  D  R  K  R  T  E  G  K  R  H  T  Q  A  V  L  A
ACTTGCTAGAAGACGGCTTAATGTTCTGTGGGCTATGCTGAGAGATCATG         1750
 L  A  R  R  R  L  N  V  L  W  A  M  L  R  D  H
CCGTGTACCATCCTGCTACCACAACAGCTGCTGCTAGACTTAAGCTTCGC         1800
 A  V  Y  H  P  A  T  T  T  A  A  A  R  L  K  L  R
AGAGGTGAGAGACCTATGAGTCTTGGCCAGGTCTTTGATCCTAGAGCTAA         1850
 R  G  E  R  P  M  S  L  G  Q  V  F  D  P  R  A  N
TGCACTGCACTCTTTCCCTCTTACAGGACGCATGCCTTGGGCTCCATTTA         1900
 A  L  H  S  F  P  L  T  G  R  M  P  W  A  P  F
TCGTTAGTTCCTGGCTCAGAAACCCTCATCCAGCTCAGTACTTCACAGCC         1950
 I  V  S  S  W  L  R  N  P  H  P  A  Q  Y  F  T  A
AGATGTCTCAGAATCCTTCCTGGTCTTTGGATTGGAGCACAGGGTGGTTC         2000
 R  C  L  R  I  L  P  G  L  W  I  G  A  Q  G  G  S
CGCAGCTAAGCTGTTGATGAGTGGTGCACCAATCGAATACGTCCTGAAAG         2050
 A  A  K  L  L  M  S  G  A  P  I  E  Y  V  L  K
ACTCAGCAGTGTGGATGTTCAAGTTCGACATTGGAGGAACACCAAGGGAT         2100
 D  S  A  V  W  M  F  K  F  D  I  G  G  T  P  R  D
ATTCCTGTCGCTGGTATCTGGAATGGAAGTTTGTGGACCCCAGCATGGGG         2150
 I  P  V  A  G  I  W  N  G  S  L  W  T  P  A  W  G
AGGTATTCATGCTATCGCTTCCAACGCTTACCAGTTCCGAAATGTGATCC         2200
 G  I  H  A  I  A  S  N  A  Y  Q  F  R  N  V  I
CTGCAAGATGGTCTGTGAGTTCAGCCGTGTTGCCAAACTATAGACTTGTT         2250
 P  A  R  W  S  V  S  S  A  V  L  P  N  Y  R  L  V
GCTGCTCTCCCCATGGCCTACCATAATCAGCGAATGAGGTTTCGGACAGA         2300
 A  A  L  P  M  A  Y  H  N  Q  R  M  R  F  R  T  D
TCTGTCCTATGGTGTGTACGGGTTCGCTGAAATCAATCCCATCGCTCTGG         2350
 L  S  Y  G  V  Y  G  F  A  E  I  N  P  I  A  L
TTGAGAAACCTGCCCTGTCTTGGAAATCCAGACTGAGACGGAAGAACTCT         2400
 V  E  K  P  A  L  S  W  K  S  R  L  R  R  K  N  S
TCCATCGCTCTCGCAAACATGGAAGATGGTGGTAGTGTTGGAAGGAGTAA        2450
 S  I  A  L  A  N  M  E  D  G  G  S  V  G  R  S  N
CGACATCCCTGGGGAGGAGGGCTAGATTTATTGGTGAGAAAGCCGAAGATC        2500
 D  I  P  G  R  R  R  A  R  F  I  G  E  K  A  E  D
CTCCTGCTCCATCTCCTAGACCCGCCTTGAGGATTCCAAACCCTCTTCTC         2550
 P  P  A  P  S  P  R  P  A  L  R  I  P  N  P  L  L
GGTCTTGATTGAATATCTAGACAGTGACCCGGGATCGACTAGATCGATCA         2600
 G  L  D
```

Figure 1

A
PLLTIGDQFPAYELTALIAGDLSKVDAKQPGDYFTTVTSEDHAGKWR
*VVFFWPKDF*TFVCPTEIATFGKLNDEFEDRDAQVLGVSIDSE*FVHFN
WRAQHED*LKNLPFPMLSDIKRELSLATGVLNADGVADRATFIVDPNN
EIQFVSVTAGSVGRNVEEV*LRVLDALQS*DELCACNWRKGDPTLNAT
ELLKASAL

B
GSIVGQTYREVEVVLVDGGSTDRTLDIANSFRPELGSRLVVHSGPDD
GPYDAMNRGVGVATGE*WVLFLGADDTLYE*PTTLAQVAAFLGDHAA
SH*LVYGDVVMRSTKSRHA*GPFDLDRLLFETNLCHQSIFYRRELFDGI
GPYNLRYRVWADWDFNIRCFSNPALITRYMDVVISEYNDMTGFSMR
QGTDKE*FRKRLPMYFWVAGWE*TCRRMLAFLKDKENRR*LALRTRLI
RVKAVSKERS*AEP

C
RI*RRHRHAEI*ILSMPGFGVILGAEFLAATGGDMAAFASADRLAGVAG
LAPVPRDSGRISGNLKRPRRYDRRLLRACYLSALVSIRTDPSSRTYY
DRKRTEGKRHTQAVLALARRRLNVLWAMLRDHAVYHPATTTAAARL

D
KLRRGERPMSLGQVFDPRANALHSFPLTGRMPWAPFIVSSWLRNP
HPAQYFTARC*LRILPGLWI*GAQGGSAAKLLMSGAPIEYVLKDSAVW
MFKFDIGGTPRDIPVAGIWNGSLWTPAWGGIHAIASNAYQFRNVIPA
RWSVSSAVLPN*YRLVAALPMA*YHNQRMRFRTDLSYGVYGFAEINPI
ALVEKPALSWKSRLRRKNSSIALANMEDGGSVGRSNDIPGRRARFI
GEKAEDPPAPSPRPAL

Figure 2 a
LPLLTIGDQFPAYEL
IGDQFPAYELTALIA
PAYELTALIAGDLSK
TALIAGDLSKVDAKQ
GDLSKVDAKQPGDYF
VDAKQPGDYFTTVTS
PGDYFTTVTSEDHAG
TTVTSEDHAGKWRVV
EDHAGKWRVVFFWPK
KWRVVFFWPKDFTFV b
FFWPKDFTFVCPTEI
DFTFVCPTEIATFGK
CPTEIATFGKLNDEF
ATFGKLNDEFEDRDA
LNDEFEDRDAQVLGV
EDRDAQVLGVSIDSE
QVLGVSIDSEFVHFN
SIDSEFVHFNWRAQH
FVHFNWRAQHEDLKN
WRAQHEDLKNLPFPM c
EDLKNLPFPMLSDIK
LPFPMLSDIKRELSL
LSDIKRELSLATGVL
RELSLATGVLNADGV
ATGVLNADGVADRAT
NADGVADRATFIVDP
ADRATFIVDPNNEIQ
FIVDPNNEIQFVSVT
NNEIQFVSVTAGSVG
FVSVTAGSVGRNVEE d
AGSVGRNVEEVLRVL
RNVEEVLRVLDALQS
VLRVLDALQSDELCA
DALQSDELCACNWRK
DELCACNWRKGDPTL
CNWRKGDPTLNATEL
GDPTLNATELLKASA
NATELLKASALGSRI e
RRGERPMSLGQVFDP
PMSLGQVFDPRANAL
HSFPLTGRMPWAPF
IVSSWLRNPHPAQYF
LRNPHPAQYFTARCL
PAQYFTARCLRILPGLWI
GAQGGSAAKLLMSGA
SAAKLLMSGAPIEYV
LMSGAPIEYVLKDSA
PIEYVLKDSAVWMFK f
LKDSAVWMFKFDIGG
VWMFKFDIGGTPRDI
FDIGGTPRDIPVAGI
TPRDIPVAGIWNGSLWT
PAWGGIHAIASNA
YQFRNVIPARWS
VSSAVLPNYRLVAAL
LPNYRLVAALPMAY
HNQRMRFRTDLSYGVY
GFAEINPIA g
LVEKPALSWKSRLRR
ALSWKSRLRRKNSSI
SRLRRKNSSIALANM
KNSSIALANMEDGGS
ALANMEDGGSVGRSN
EDGGSVGRSNDIPGR
VGRSNDIPGRRARFI
DIPGRRARFIGEKAE
RARFIGEKAEDPPAP
GEKAEDPPAPSPRPAL h
RIRRHRHAEIILSMP
RHAEIILSMPGFGVI
ILSMPGFGVILGAEF
GFGVILGAEFLAATG
LGAEFLAATGGDMAA
LAATGGDMAAFASAD
GDMAAFASADRLAGV
FASADRLAGVAGLAP
RLAGVAGLAPVPRDS
AGLAPVPRDSGRISG i
VPRDSGRISGNLKRP
GRISGNLKRPRRYDR
NLKRPRRYDRRLLRA
RRYDRRLLRACYLSA
RLLRACYLSALVSIR
CYLSALVSIRTDPSS
LVSIRTDPSSRTYYD
TDPSSRTYYDRKRTE
RTYYDRKRTEGKRHT
RKRTEGKRHTQAVLA j
GKRHTQAVLALARRR
QAVLALARRRLNVLW
LARRRLNVLWAMLRD
LNVLWAMLRDHAVYH
AMLRDHAVYHPATTT
HAVYHPATTTAAARL
IVGQTYREVEVVLVD
TYREVEVVLVDGGST
EVVLVDGGSTDRTLD
DGGSTDRTLDIANSF k
DRTLDIANSFRPELG
IANSFRPELGSRLVV
RPELGSRLVVHSGPD
SRLVVHSGPDDGPYD
HSGPDDGPYDAMNRG
DGPYDAMNRGVGVAT
AMNRGVGVATGEWVL
VGVATGEWVLFLGAD
GEWVLFLGADDTLYE
FLGADDTLYEPTTLA l
DTLYEPTTLAQVAAF
PTTLAQVAAFLGDHA
QVAAFLGDHAASHLV
LGDHAASHLVYGDVV
ASHLVYGDVVMRSTK
YGDVVMRSTKSRHAG
MRSTKSRHAGPFDLD
SRHAGPFDLDRLLFEPF
DLDRLLFETNLCHRLL
FETNLCHQSIFY m
TNLCHQSIFYRRELF
QSIFYRRELFDGIGP
RRELFDGIGPYNLRY
DGIGPYNLRYRVWAD
YNLRYRVWADWDFNI
RVWADWDFNIRCFSN
WDFNIRCFSNPALIT
RCFSNPALITRYMDV
PALITRYMDVVISEY
RYMDVVISEYNDMTG
VISEYNDMTGFSMRQ n
NDMTGFSMRQGTDKE
FSMRQGTDKEFRKRL
GTDKEFRKRLPMYFW
FRKRLPMYFWVAGWE
PMYFWVAGWETCRRM
VAGWETCRRMLAFLK
TCRRMLAFLKDKENR
LAFLKDKENRRLALR
DKENRRLALRTRLIR
RLALRTRLIRVKAVS
TRLIRVKAVSKERSA

Figure 4

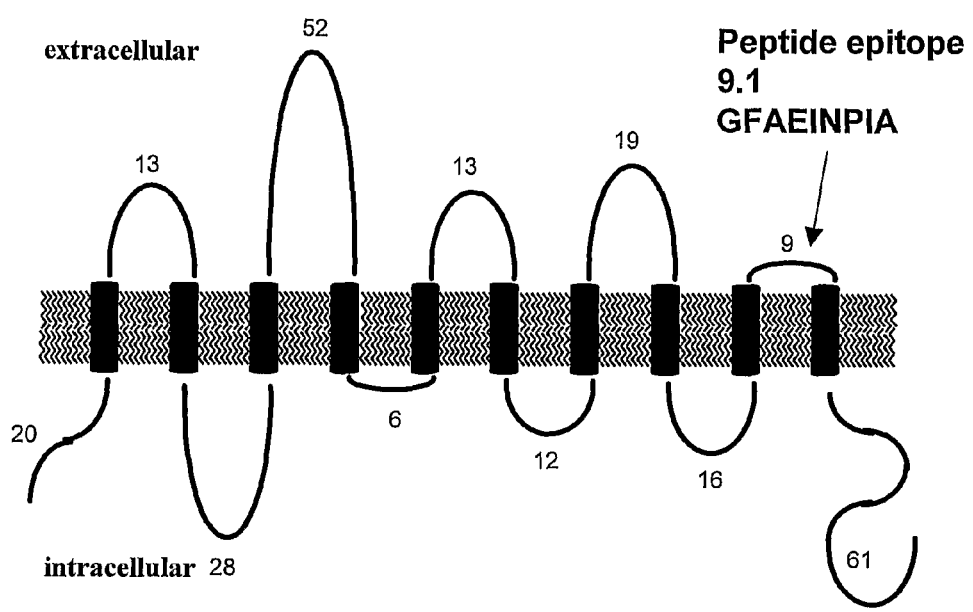
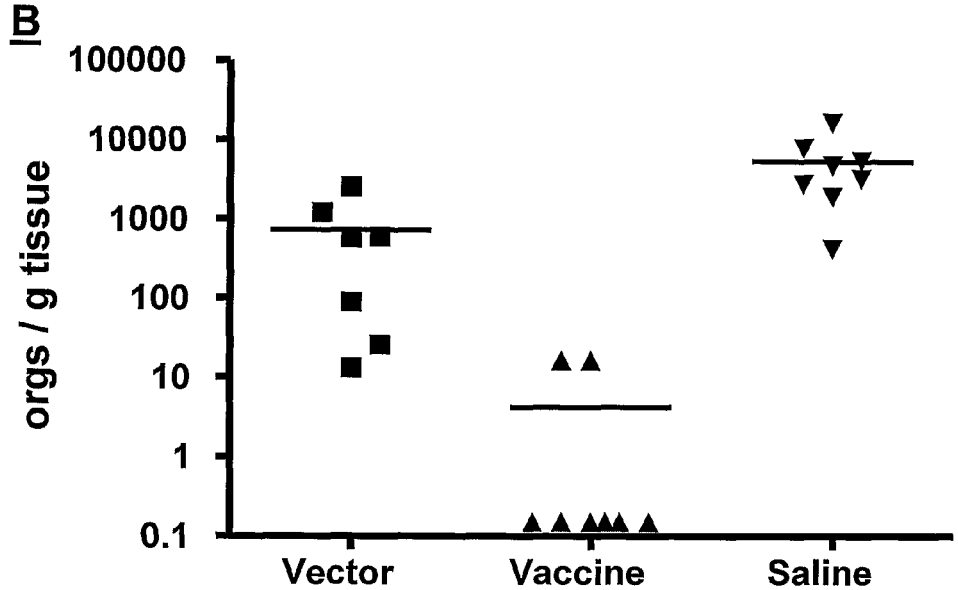
Figure 5

IMMUNOGENIC CONSTRUCTS

CROSS-REFERENCE TO RELATED APPLICATIONS

This application claims priority under 35 U.S.C. §371 from International Application No. PCT/GB2006/002893, filed Aug. 3, 2006, which claims priority from U.S. Provisional Patent Application No. 60/706,594, filed Aug. 9, 2005.

FIELD OF THE INVENTION

The present invention relates to the treatment or prevention of infection with *Mycobacterium avium* subspecies *paratuberculosis* (MAP), and to the treatment or prevention of disorders associated with such infection.

BACKGROUND TO THE INVENTION

*Mycobacterium avium* subspecies *paratuberculosis* (MAP) is a member of the *Mycobacterium avium* complex MAC. Unlike other environmental MAC, MAP has the specific ability to cause chronic inflammation of the intestine of a range of histopathological types in many animals including primates. Despite its broad pathogenicity, MAP can live in animals for years without causing clinical disease. MAP is more thermotolerant than *M. bovis* and has been cultured from retail pasteurised milk in the UK, Czech Republic and the USA. Transmittal from livestock to humans by this route is therefore probable. There is also a high risk of transmittal from sources of environmental contamination such as rivers and surface waters used for domestic supply.

MAP can cause of Crohn's disease in humans, in particular in people who have an inherited or acquired susceptibility. Recent studies have confirmed that the inflamed intestine of most people with Crohn's disease is infected with these chronic enteric pathogens. Further studies have reported that MAP can be cultured from the blood of 50% of patients with Crohn's disease showing that, as in animals, the infection is often systemic. Furthermore a high proportion of people with Irritable Bowel Syndrome are also infected with MAP.

The organisms in humans are very slow growing and exceedingly difficult to isolate and passage in conventional culture. They are present in low abundance and adopt a Ziehl Neelsen (ZN) staining negative form which cannot be seen in tissues by ordinary light microscopy. They appear to be able to minimise immune recognition and unlike conventional spheroplasts, their ZN negative form is highly resistant to chemical and enzymatic lysis procedures essential for reliable detection by PCR.

MAP infections are extremely difficult to eradicate. ZN-negative intracellular MAP are highly resistant in vivo to standard anti-TB drugs. However, a substantial proportion of patients with Crohn's disease who can take rifabutin/clarithromycin combinations, to which MAP are more sensitive, heal, sometimes dramatically.

SUMMARY OF THE INVENTION

The present invention relates to molecules, in particular polypeptides and the polynucleotides which can be used to express them, which can be used to induce a therapeutic or prophylactic immune response against MAP in humans and animals.

In particular, the present invention provides a polypeptide comprising an ahpC polypeptide sequence, a gsd polypeptide sequence, a p12 polypeptide sequence and an mpa polypeptide sequence, wherein said ahpC polypeptide comprises the sequence of SEQ ID NO: 2, a variant thereof having more than 70% amino acid sequence identity to SEQ ID NO: 2 across the full length of SEQ ID NO: 2, or a fragment of at least 8 amino acids of SEQ ID NO: 2 which comprises an epitope;

said gsd polypeptide comprises the sequence of SEQ ID NO: 6, a variant thereof having more than 70% amino acid sequence identity to SEQ ID NO: 6 across the full length of SEQ ID NO: 6, or a fragment of at least 8 amino acids of SEQ ID NO: 6 which comprises an epitope;

said p12 polypeptide comprises the sequence of SEQ ID NO: 10, a variant thereof having more than 70% amino acid sequence identity to SEQ ID NO: 10 across the full length of SEQ ID NO: 10, or a fragment of at least 8 amino acids of SEQ ID NO: 10 which comprises an epitope; and said mpa polypeptide comprises the sequence of SEQ ID NO: 14, a variant thereof having more than 70% amino acid sequence identity to SEQ ID NO: 14 across the full length of SEQ ID NO: 14, or a fragment of at least 8 amino acids of SEQ ID NO: 14 which comprises an epitope.

Preferably such a variant maintains the ability to generate an immune response against the unmodified polypeptide. A preferred variant ahpC polypeptide has the amino acid sequence given in SEQ ID NO: 4. A preferred variant gsd polypeptide has the amino acid sequence given in SEQ ID NO: 8. A preferred variant p12 polypeptide has the amino acid sequence given in SEQ ID NO: 12. A preferred variant mpa polypeptide has the amino acid sequence given in SEQ ID NO: 16. A preferred polypeptide of the invention comprises the amino acid sequence of SEQ ID Nos: 4, 8, 12 and 16. A particularly preferred amino acid sequence is given in SEQ ID NO: 24.

The present invention also provides polynucleotides which encode such polypeptides. A polynucleotide of the invention may comprise (a) the ahpC polynucleotide of SEQ ID NO: 1 or a variant thereof having at least 70% homology to SEQ ID NO: 1 across the full length of SEQ ID NO: 1 or a fragment of at least 24 nucleotides of SEQ ID NO: 1 which encodes an epitope;

(b) the gsd polynucleotide of SEQ ID NO: 5 or a variant thereof having at least 70% homology to SEQ ID NO: 5 across the full length of SEQ ID NO: 5 or a fragment of at least 24 nucleotides of SEQ ID NO: 5 which encodes an epitope;

(c) the p12 polynucleotide of SEQ ID NO: 9 or a variant thereof having at least 70% homology to SEQ ID NO: 1 across the full length of SEQ ID NO: 9 or a fragment of at least 24 nucleotides of SEQ ID NO: 9 which encodes an epitope; and (d) the mpa polynucleotide of SEQ ID NO: 13 or a variant thereof having at least 70% homology to SEQ ID NO: 1 across the full length of SEQ ID NO: 13 or a fragment of at least 24 nucleotides of SEQ ID NO: 13 which encodes an epitope.

A polynucleotide of the invention will encode a polypeptide of the invention. In one embodiment a polynucleotide variant as defined above will differ from the given SEQ ID NO by virtue of degeneracy in the genetic code. In one embodiment, a polynucleotide variant will be codon optimised for the species which it is desired to treat.

The present invention also provides:

A vector comprising a polynucleotide of the invention, or a vector capable of expressing an ahpC polypeptide, a gsd polypeptide, a p12 polypeptide and an mpa polypeptide as defined above. Preferred vector types include poxvirus vectors, adenovirus vectors and plasmids.

A host cell comprising a polypeptide, polynucleotide or vector of the invention or a host cell capable of expressing a polypeptide of the invention.

A polypeptide, polynucleotide, vector or host cell of the invention for use in therapy. In particular, the use of such a polypeptide, polynucleotide, vector or host cell in the manufacture of a medicament for treating or preventing MAP infection or a condition or symptom associated with MAP infection.

A method of treating or preventing MAP infection of a condition or symptom associated with MAP infection comprising administering to a subject in need thereof an effective amount of a polypeptide, polynucleotide, vector or host cell of the invention. The subject may also be administered with a further therapeutic agent.

A kit for use in treating or preventing MAP infection or a condition or symptom associated with MAP infection, said kit comprising (i) at least one polypeptide, polynucleotide, vector or host cell of the invention and (ii) at least one other therapeutic agent, for simultaneous, sequential or separate use.

BRIEF DESCRIPTION OF THE FIGURES

FIG. 1 shows the nucleotide and amino acid sequences of the Havilah construct (SEQ ID NOs:26 and 27). The amino acid sequence comprises a ubiquitin leader sequence followed by an ahpC sequence (italics), a gsd sequence (bold), a p12 sequence (plain text) and an mpa sequence (bold italics). The amino acid sequence ends with a pK tag.

FIG. 2 shows the ahpC (A) (SEQ ID NO:4), gsd (B) (SEQ ID NO:8), p12 (C) (SEQ ID NO:2) and mpa (D) (SEQ ID NO:16) polypeptides included in the Havilah construct. Bold italics=predicted strong class II human epitope. Underlined=predicted class I epitope.

FIG. 4. Summary of the sequences of the synthetic peptide antigens spanning the Havilah polyprotein used in the detection of epitope regions (SEQ ID NOs:28-167). AhpC peptides in italics, Mpa peptides in bold italics, p12 peptides in plain text, and gsd peptides in bold.

FIG. 5. A. Diagram of the structure of the mpa antigen in the cell surface membrane of MAP showing intracellular, transmembrane and extracellular domains. The strong T cell epitope GFAEINPIA (SEQ ID NO:25) in peptide 9.1 is seen to comprise the fifth and smallest extracellular loop of the protein. B. Highly significant reduction by 2-3 log units and elimination of MAP organisms in the spleen tissue of MAP-infected C57/BL6 mice in response to therapeutic vaccination, 26 weeks after infection with a slow growing laboratory strain of MAP compared to vector-only and sham vaccinated animals. * MAP not detected by sensitive qPCR in the spleens of 6 of the 8 mice.

BRIEF DESCRIPTION OF THE SEQUENCES

SEQ ID Nos 1 and 2 are the polynucleotide and polypeptide sequences respectively for the MAP ahpC gene.

SEQ ID Nos 3 and 4 are a modified version of the MAP ahpC gene, in which the polynucleotide sequence has been codon optimised for human use.

SEQ ID Nos 5 and 6 are the polynucleotide and polypeptide sequences respectively for the MAP gsd gene.

SEQ ID Nos 7 and 8 are a modified version of the MAP gsd gene, in which the polynucleotide sequence has been codon optimised for human use and which is truncated at the N-terminal in order to remove the cysteine residue at position 22.

SEQ ID Nos 9 and 10 are the polynucleotide and polypeptide sequences respectively for the MAP p12 gene.

SEQ ID Nos 11 and 12 are a modified version of the MAP p12 gene, in which the polynucleotide sequence has been codon optimised for human use.

SEQ ID Nos 13 and 14 are the polynucleotide and polypeptide sequences respectively for the MAP mpa gene.

SEQ ID Nos 15 and 16 are a modified version of the MAP mpa gene, in which the polynucleotide sequence has been codon optimised for human use and a number of transmembrane regions have been removed.

SEQ ID NO: 17 is a ubiquitin leader sequence.

SEQ ID NO: 18 is a pK Tag sequence.

SEQ ID Nos 19 and 20 are a polynucleotide construct and the encoded peptide consisting of the modified ahpC, gsd, p12 and mpa sequences above.

SEQ ID Nos 21 and 22 are a polynucleotide construct and the encoded peptide consisting of the modified ahpC, gsd, p12 and mpa sequences above, together with a ubiquitin leader sequence and a pK tag.

SEQ ID NO: 23 is the polynucleotide sequence of the Havilah construct and SEQ ID NO: 24 is the polypeptide sequence encoded by Havilah.

Figure 3:
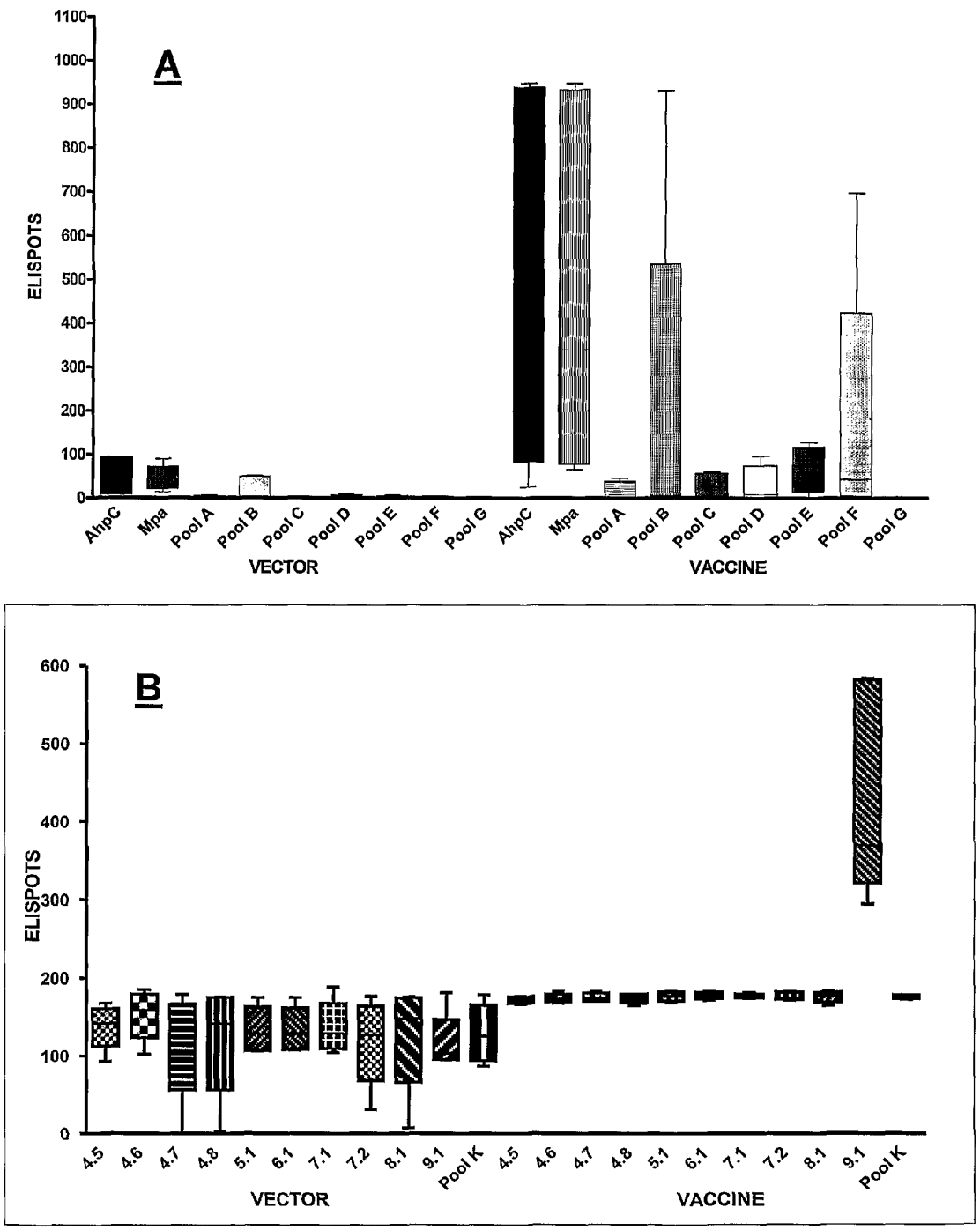
FIG. 3. A. Shows the highly significantly increased antigen-specific ELISPOT responses to rec.AhpC and rec.Mpa, as well as to synthetic peptides from the Havilah polyprotein in pools B and F, resulting from vaccination of naïve uninfected C57/BL6 MICE with the recombinant plasmid pSG2.HAV followed by MVA.HAV when compared to vector-only controls. B. example of the identification of an epitope from ELISPOT responses to the synthetic peptides in pool F (see also FIG. 4) in the pSG2.HAV/MVA.HAV vaccinated animals. The response in vaccinated, but not unvaccinated animals is seen to be due to the strong recognition of the peptide 9.1 with the amino acid sequence GFAEINPIA constituting a specific T cell epitope.

SEQ ID NO: 25 is a T cell epitope from the mpa polypeptide sequence as identified in FIGS. 3 and 4.

DETAILED DESCRIPTION OF THE INVENTION

The present invention relates to the use of a combination of four proteins deriving from MAP in the treatment or prevention of MAP infection or conditions associated with the presence of MAP in humans or animals. The four proteins are ahpC, gsd, p12 and mpa. AhpC and p12 are secreted components while gsd and mpa are both membrane bound molecules in MAP.

ahpC is a secreted component shared by many pathogenic mycobacteria. It is involved in the ability of MAP to survive within macrophages and is upregulated on entry into a state of microbial dormancy. The nucleic acid and amino acid sequences of the MAP ahpC gene and protein are given in SEQ ID Nos 1 and 2 respectively. For use in the present invention, this sequence, or a variant thereof as discussed below may be used. For example, the MAP ahpC gene sequence may be codon optimised as discussed further below to make it more suitable for mammalian, in particular human, use. A suitable modified ahpC sequence and encoded protein are given in SEQ ID Nos 3 and 4 respectively.

gsd is a glycosyl transferase encoded by the GS pathogenicity element with a predicted signal sequence and lipid acylation site. Microarray analysis shows that it is up-regulated in the intracellular environment. It is expressed on the microbial cell surface and is predicted to transfer GDP-fucose to sub-terminal rhamnose to cap surface glycopeptidolipid on MAP with derivatised fucose giving the pathogen in its ZN-negative state an inert, hydrophobic, and highly resistant cell surface. The nucleic acid and amino acid sequences of the MAP gsd gene and protein are given in SEQ ID Nos 5 and 6 respectively. For use in the present invention, this sequence, or a variant thereof as discussed below, may be used. For example, the MAP gsd gene sequence may be codon optimised as discussed further below to make it more suitable for mammalian, in particular human, use. Other modifications may be made, for example potential acylation sites may be removed. One suitable modified gsd sequence and encoded protein are given in SEQ ID Nos 7 and 8 respectively.

p12 is the carboxyterminal 17 kDa fragment of p43 encoded by IS900 which is also up-regulated intracellularly. It is strongly predicted on the cell surface and both in MAP and in p43.rec.*E. coli* it is the substrate for specific proteolytic cleavage and exodomain release. The nucleic acid and amino acid sequences of the MAP p12 gene and protein are given in SEQ ID Nos 9 and 10 respectively. For use in the present invention, this sequence, or a variant thereof as discussed below may be used. For example, the MAP p12 gene sequence may be codon optimised as discussed further below to make it more suitable for mammalian, in particular human, use. One suitable modified p12 sequence and encoded protein are given in SEQ ID Nos 11 and 12 respectively.

mpa is also expressed on the surface of MAP and is believed to be unique to the pathogen. It is both an acetylase and a predicted pore molecule with 10 transmembrane regions and a large extracellular peptide loop. The nucleic acid and amino acid sequences of the MAP mpa gene and protein are given in SEQ ID Nos 13 and 14 respectively. For use in the present invention, this sequence, or a variant thereof as discussed below may be used. For example, the MAP mpa gene sequence may be codon optimised as discussed further below to make it more suitable for mammalian, in particular human, use. Other modifications may be made, for example transmembrane regions may be removed to reduce the hydrophobicity of the protein. One suitable modified mpa sequence and encoded protein are given in SEQ ID Nos 15 and 16 respectively.

According to the present invention each of these four proteins, or variants of any thereof, are provided in combination.

Polypeptides

The invention relates to the provision of an ahpC polypeptide, a gsd polypeptide, a p12 polypeptide and an mpa polypeptide in combination.

A "polypeptide" is used herein in its broadest sense to refer to a compound of two or more subunit amino acids, amino acid analogs, or other peptidomimetics. The term "polypeptide" thus includes short peptide sequences and also longer polypeptides and proteins. As used herein, the term "amino acid" refers to either natural and/or unnatural or synthetic amino acids, including glycine and both the D or L optical isomers, and amino acid analogs and peptidomimetics.

A suitable ahpC polypeptide may have the amino acid sequence of SEQ ID NO: 2 or SEQ ID NO: 4. A suitable gsd polypeptide may have the amino acid sequence of SEQ ID NO: 6 or SEQ ID NO: 8. A suitable p12 polypeptide may have the amino acid sequence of SEQ ID NO: 10 or SEQ ID NO: 12. A suitable mpa polypeptide may have the amino acid sequence of SEQ ID NO: 14 or SEQ ID NO: 16. A suitable ahpC, gsd, p12 or mpa sequence may alternatively be a variant of one of these specific sequences. For example, a variant may be a substitution, deletion or addition variant of any of the above amino acid sequences, or may be a fragment of any thereof as described further below.

A variant of one of the four polypeptide may comprise 1, 2, 3, 4, 5, up to 10, up to 20, up to 30 or more amino acid substitutions and/or deletions from the sequences given in the sequence listing. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| | |
|---|---|
| Ala | aliphatic, hydrophobic, neutral |
| Cys | polar, hydrophobic, neutral |
| Asp | polar, hydrophilic, charged (−) |
| Glu | polar, hydrophilic, charged (−) |
| Phe | aromatic, hydrophobic, neutral |

-continued

| | |
|---|---|
| Gly | aliphatic, neutral |
| His | aromatic, polar, hydrophilic, charged (+) |
| Ile | aliphatic, hydrophobic, neutral |
| Lys | polar, hydrophilic, charged (+) |
| Leu | aliphatic, hydrophobic, neutral |
| Met | hydrophobic, neutral |
| Asn | polar, hydrophilic, neutral |
| Pro | hydrophobic, neutral |
| Gln | polar, hydrophilic, neutral |
| Arg | polar, hydrophilic, charged (+) |
| Ser | polar, hydrophilic, neutral |
| Thr | polar, hydrophilic, neutral |
| Val | aliphatic, hydrophobic, neutral |
| Trp | aromatic, hydrophobic, neutral |
| Tyr | aromatic, polar, hydrophobic |

Preferred “derivatives” or “variants” include those in which instead of the naturally occurring amino acid the amino acid which appears in the sequence is a structural analog thereof. Amino acids used in the sequences may also be derivatized or modified, e.g. labelled, providing the function of the peptide is not significantly adversely affected.

Derivatives and variants as described above may be prepared during synthesis of the peptide or by post-production modification, or when the peptide is in recombinant form using the known techniques of site-directed mutagenesis, random mutagenesis, or enzymatic cleavage and/or ligation of nucleic acids.

Suitable variants may also be naturally occurring polypeptides from mycobacteria other than MAP. For example, a variant ahpC polypeptide sequence may derive from a different mycobacterial strain to MAP. Such naturally occurring variants preferably maintain the ability to stimulate an immune response which is capable of acting against MAP. That is, the immune response to the variant polypeptide will react against MAP polypeptides as well as the variant polypeptide used.

Preferably variants according to the invention have an amino acid sequence which has more than 60%, or more than 70%, e.g. 75 or 80%, preferably more than 85%, e.g. more than 90 or 95% amino acid identity to, for example, SEQ ID NO: 2, 4, 6, 8, 10, 12, 14 or 16, (according to the test described hereinafter). This level of amino acid identity may be seen across the full length of the sequence or over a part of the sequence, such as 20, 30, 50, 75, 100, 150, 200 or more amino acids, depending on the size of the full length polypeptide.

In connection with amino acid sequences, “sequence identity” refers to sequences which have the stated value when assessed using ClustalW (Thompson et al., 1994, supra) with the following parameters:

Pairwise alignment parameters—Method: accurate, Matrix: PAM, Gap open penalty: 10.00, Gap extension penalty: 0.10;

Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: GPSNDQEKR. Sequence identity at a particular residue is intended to include identical residues which have simply been derivatized.

Particular modifications can be made to any of the wild type MAP proteins sequences given in SEQ ID Nos: 2, 6, 10 and 14. For example, modification can be made to try to improve the overall properties of the variant protein as an immunogen.

In one embodiment, a wild-type protein may be modified by deletion or substitution to remove an acylation site. Such an acylation site might affect the overall conformation of the protein. By omitting acylation sites, for example by excluding or substituting a cysteine residue, the presentation of effective epitopes within the protein may be optimised. For example, the wild type MAP gsd sequence given in SEQ ID NO: 6 includes a cysteine residue at position 22. In the variant of SEQ ID NO: 8, the amino acid sequence has been modified by truncation at the N-terminal such that this cysteine residue is no longer present. Such a modification may be made to a wild type protein or to any of the variant or fragment sequences, such as the codon optimised sequences, described herein.

In another embodiment, a wild type MAP protein may be modified to disable or remove potential cross-reacting epitopes. For example, where a polypeptide of the invention is intended for use in a human, the polypeptide sequence may be modified to disable or remove potential cross-reacting human epitopes, such as sequences which generate antibodies in human patients which may cross-react with similar sequences in human proteins. Modifications may thus be made to the MAP sequences to avoid such cross-reactivity but to maintain the ability to generate an anti-MAP immune response.

For example within the wild type MAP gsd sequence the lysine residues at positions 239 and 241 (see SEQ ID NO: 6) may each be substituted with asparagine. An equivalent substitution may be made in any of the variant or fragment gsd sequences described herein. For example in the variant sequence of SEQ ID NO: 8, the lysine residues at positions 216 and 218 may be replaced with asparagines. This may be achieved by modifying the nucleic acid sequence which encodes the gsd polypeptide. For example, in the gsd polynucleotide sequence of SEQ ID NO: 7, the AAG codons at positions 646 to 648 and 651 to 654 may be replaced by AAT. This maintains the optimised human codon usage of SEQ ID NO: 7 and further removes potentially cross-reacting human epitopes.

Similarly, modifications mat be made to the MAP ahpC sequence. In the wild-type ahpC sequence of SEQ ID NO: 2, the lysine at position 29 may be replaced with threonine and the proline at position 31 may be replaced with leucine. An equivalent substitution may be made in any of the variant or fragment ahpC sequences described herein. For example, in the modified variant sequence of SEQ ID NO: 4, the same substitutions may be made at the position 28 lysine and the position 30 proline. This may be achieved by modifying the nucleic acid sequence which encodes the ahpC polypeptide. For example, in the ahpC polynucleotide sequence of SEQ ID NO: 3, the AAA codon at positions 82 to 84 may be replaced by ACA and the CCC codon at positions 88 to 90 may be replaced by CTC. This maintains the optimised human codon usage of SEQ ID NO: 3 and further removes potentially cross-reacting human epitopes.

Similarly, modifications may be made to reduce the hydrophobicity of the protein and thus to help optimise the surface presentation of epitopes. For example, the wild-type mpa sequence of SEQ ID NO: 14 includes ten transmembrane regions. In order to reduce the hydrophobicity of the protein, one or more of these regions, or parts of these regions, may be omitted or substituted. For example, one, more or all of the transmembrane regions may be deleted. Such regions may be deleted totally or partially, optionally leaving none, one, two or more amino acid residues from the ends of the transmembrane sequence in the protein. Thus one modification may be the deletion or substitution of one or more hydrophobic amino acids. An example of this is seen in SEQ ID NO: 16 which is a variant of MAP mpa in which most of the transmembrane sequences have been deleted, leaving only one or two amino acids from the transmembrane regions in the variant polypeptide.

Polypeptide "fragments" according to the invention may be made by truncation, e.g. by removal of one or more amino acids from the N and/or C-terminal ends of a polypeptide. Up to 10, up to 20, up to 30, up to 40 or more amino acids may be removed from the N and/or C terminal in this way. Fragments may also be generated by one or more internal deletions. For example, a variant of the invention may consist of or comprise two or more epitope regions from a full length polypeptide of the region in the absence of non-epitope amino acids. Preferably a fragment of an ahpC, gsd, p12 or mpa polypeptide comprises at least one epitope capable of inducing an immune response against the unmodified MAP polypeptide. Such fragments may be derived from a sequence of SEQ ID NO: 2, 4, 6, 8, 10, 12, 14 or 16 or may be derived from a variant peptide as described herein. Preferably such fragments are between 8 and 150 residues in length, e.g. 8 to 50 or 8 to 30 residues. Alternatively, fragments of the invention may be longer sequences, for example comprising at least 50%, at least 60%, at least 70%, at least 80% or at least 90% of a full length polypeptide of the invention.

Preferably, a variant of one of the four polypeptides is a functional variant thereof. In particular, a variant polypeptide should retain the ability to stimulate an immune response against the unmodified MAP polypeptide. In one embodiment, a functional variant polypeptide should be capable of acting as an antigen and should include at least one functional epitope from the original polypeptide.

An "antigen" refers to any agent, generally a macromolecule, which can elicit an immunological response in an individual. As used herein, "antigen" is generally used to refer to a polypeptide molecule or portion thereof which contains one or more epitopes. Furthermore, for the purposes of the present invention, an "antigen" includes a polypeptide having modifications, such as deletions, additions and substitutions (generally conservative in nature) to the native sequence, so long as the polypeptide maintains sufficient immunogenicity. These modifications may be deliberate, for example through site-directed mutagenesis, or may be accidental, such as through mutations of hosts which produce the antigens.

An "immune response" against an antigen of interest is the development in an individual of a humoral and/or a cellular immune response to that antigen. For purposes of the present invention, a "humoral immune response" refers to an immune response mediated by antibody molecules, while a "cellular immune response" is one mediated by T-lymphocytes and/or other white blood cells.

As used herein, the term "epitope" generally refers to the site on a target antigen which is recognised by an immune receptor such as a T-cell receptor and/or an antibody. Preferably it is a short peptide derived from or as part of a protein. However the term is also intended to include peptides with glycopeptides and carbohydrate epitopes. A single antigenic molecule, such as one of the four proteins described herein, may comprise several different epitopes. The term "epitope" also includes modified sequences of amino acids or carbohydrates which stimulate responses which recognise the whole organism.

It is advantageous if the selected epitope is specific to MAP, or involved in the pathogenicity of MAP. For example, it is advantageous if the immune receptor and/or antibody which recognises the epitope will only recognise this epitope from MAP, and not epitopes in other unrelated proteins, in particular proteins from unrelated organisms or host proteins. If the epitope is involved in pathogenicity of MAP, then an immune response against such an epitope may be used to target pathogenic MAP infections.

An epitope may also be related to equivalent epitopes on other mycobacteria. For example, many individuals suffering from MAP infection are also infected by M. avium as a secondary co-pathogen. Other M. avium complexes may be present or involved in Crohn's disease. Many of the proteins expressed in MAP such as AhpC are very similar to those expressed in M. avium. If the polypeptide of the invention includes one or more epitopes which are capable of stimulating an immune response which acts against M. avium in addition to MAP, a further, secondary, therapeutic effect may be achieved.

Epitopes can be identified from knowledge of the amino acid and corresponding DNA sequences of the peptide or polypeptide, as well as from the nature of particular amino acids (e.g., size, charge, etc.) and the codon dictionary, without undue experimentation. See, e.g., Ivan Roitt, Essential Immunology, 1988; Janis Kuby, Immunology, 1992 e.g., pp. 79-81. Some guidelines in determining whether a protein or an epitope of interest will stimulate a response, include: peptide length—the peptide should be at least 8 or 9 amino acids long to fit into the MHC class I complex and at least 8-25, such at least as 13-25 amino acids long to fit into a class II MHC complex. These lengths are the minimum for the peptide to bind to the respective MHC complex. It is preferred for the peptides to be longer than these lengths because cells may cut peptides. The peptide should contain an appropriate anchor motif which will enable it to bind to the various class I or class II molecules with high enough specificity to generate an immune response. This can be done, without undue experimentation, by comparing the sequence of the protein of interest with published structures of peptides associated with the MHC molecules. Thus, the skilled artisan can ascertain an epitope of interest by comparing the protein sequence with sequences listed in the protein database.

Suitable epitopes may thus be identified by routinely used methods such as those demonstrated in FIGS. 3 and 4 for identifying the strong T cell epitope GFAEINPIA (peptide 9.1) in the $5^{th}$ extracellular loop of mpa. In such a method, a library of short peptides which are fragments of the polypeptide sequence of interested may be generated and each of these peptides assessed separately for their ability to identify an immune response against the full length polypeptide. Members of the library may be screened in groups or pools or individual members of the library, such as individual members of a single pool, may be assessed separately.

In a further example, epitope scanning of the individual proteins of SEQ ID Nos 4, 8, 12 and 16 revealed a number of predicted class I and class II epitopes.

In the ahpC variant sequence of SEQ ID NO: 4, predicted strong class II epitopes were identified at amino acids 48 to 56, 90 to 101 and 161 to 169. An ahpC polypeptide of the invention, such as an ahpC variant or fragment polypeptide, preferably comprises at least one, for example one, two or all three of these epitopes.

In the gsd variant sequence of SEQ ID NO: 8, predicted class I epitopes were identified at amino acids 1 to 32, 58 to 68, 99 to 119, 123 to 147, 159 to 169, 180 to 194 and 200 to 231, and predicted strong class II epitopes were identified at amino acids 64 to 76, 95 to 110, 192 to 206 and 223 to 240. A gsd polypeptide of the invention, such as a gsd variant or fragment polypeptide, preferably comprises at least one, for example one, two, three, four, five, six, seven, eight, nine, ten or all of these epitopes.

In the p12 variant sequence of SEQ ID NO 12, predicted class I epitopes were identified at amino acids 33 to 56 and 98 to 117 and a predicted strong class II epitope was identified at amino acids 3 to 10. A p12 polypeptide of the invention, such as a p12 variant or fragment polypeptide, preferably comprises at least one, for example one, two or all three of these epitopes.

In the mpa variant sequence of SEQ ID NO: 16, a predicted class I epitope was identified at amino acids 130 to 160, and predicted strong class II epitopes were identified at amino acids 56 to 64 and 150 to 160. An mpa polypeptide of the invention, such as an mpa variant or fragment polypeptide, preferably comprises at least one, for example one, two or all three of these epitopes.

As shown in the Examples, a particular strong T cell epitope has been identified in the mpa polypeptide sequence. This epitope has the amino acid sequence GFAEINPIA (SEQ ID NO: 25) and is located at amino acids 357 to 365 of SEQ ID NO: 14 and amino acids 177 to 185 of SEQ ID NO: 16. This sequence is found in the construct of SEQ ID NO: 24 at amino acids 761 to 769. A preferred mpa polypeptide sequence is a sequence which comprises GFAEINPIA. Such a sequence may also comprise one, two or all three of the predicted class I and class II epitopes mentioned above.

This epitope is believed to be located in the fifth extracellular loop of mpa (FIG. 5A). A preferred mpa polypeptide may therefore maintain the sequence of the fifth extracellular loop. An mpa polypeptide may therefore comprise the amino acid sequence GFAEINPIA and also adjacent amino acids from the fifth extracellular loop of mpa. Preferably, this fifth extracellular loop will be present in a polypeptide of the invention in a suitable form and conformation for it to be recognised by the immune system.

Preferably, the four polypeptides ahpC, gsd, p12 and mpa are provided together in a single fusion protein. The four polypeptide sequences in such a fusion protein may be any of the polypeptides or variants described herein. The four polypeptides may be provided in any order in the fusion protein. In one embodiment they are provided in the order ahpC-gsd-p12-mpa.

In one embodiment, the four polypeptides present in a fusion protein are those given in SEQ ID Nos 4, 8, 12 and 16. For example, these four proteins may be provided in a fusion protein in this order as shown in SEQ ID NO: 20.

In an alternative embodiment, the polypeptides may be present in two or more separate polypeptide molecules, which may or may not be linked by non-covalent linkages. For example, the four polypeptides may be provided separately, or may be provided in two or three separate fusion protein polypeptide molecules. For example, three of the polypeptides may be provided in a single polypeptide molecule and the fourth provided separately, two may be provided in one molecule and the other two provided separately, or the four polypeptides may be provided in two polypeptide molecules, each comprising two of the four polypeptides.

In a fusion protein of the invention, linker sequences may separate the required polypeptide sequences and/or there may or may not be additional sequences present at the N terminal or C terminal of the peptide. Typically the fusion protein comprises 1, 2, 3, or more such linkers. The linkers are typically 1, 2, 3, 4 or more amino acids in length. Thus in the peptide 1, 2, 3 or all of the polypeptide sequences may be contiguous with each other or may be separated from each other, for example by such linkers.

A polypeptide of the invention may comprise further additional sequences, for example those encoded by the polynucleotides and vectors described below. For example, it may comprise additional epitopes, therapeutic polypeptides, adjuvants or immunomodulatory molecules.

The polypeptide may comprise a leader sequence, i.e. a sequence at or near the amino terminus of the polypeptide that functions in targeting or regulation of the polypeptide. For example a sequence may be included in the polypeptide that targets it to particular tissues in the body, or which helps the processing or folding of the polypeptide upon expression. Various such sequences are well known in the art and could be selected by the skilled reader depending upon, for example, the desired properties and production method of the polypeptide. One example of such a leader is the ubiquitin leader sequence given in SEQ ID NO: 17.

A polypeptide may further comprise a tag or label to identify or screen for the polypeptide, or for expression of the polypeptide. Suitable labels include radioisotopes such as $^{125}I$, $^{32}P$ or $^{35}S$, fluorescent labels, enzyme labels, or other protein labels such as biotin. Suitable tags may be short amino acid sequences that can be identified by routine screening methods. For example, a short amino acid sequence may be included that is recognised by a particular monoclonal antibody. One such tag of the pK tag given in SEQ ID NO: 18.

In one embodiment, a polypeptide of the invention has the sequence given in SEQ ID NO: 24. This is referred to herein as the Havilah polypeptide sequence and comprises the four modified polypeptides of SEQ ID Nos: 4, 8, 12 and 16, and additional sequences such as a ubiquitin leader sequence and a pK tag.

Peptides of the invention, as defined herein, may be chemically modified, for example, post-translationally modified. For example they may be glycosylated or comprise modified amino acid residues. They can be in a variety of forms of polypeptide derivatives, including amides and conjugates with polypeptides.

Chemically modified peptides also include those having one or more residues chemically derivatized by reaction of a functional side group. Such derivatized side groups include those which have been derivatized to form amine hydrochlorides, p-toluene sulfonyl groups, carbobenzoxy groups, t-butyloxycarbonyl groups, chloroacetyl groups and formyl groups. Free carboxyl groups may be derivatized to form salts, methyl and ethyl esters or other types of esters or hydrazides. Free hydroxyl groups may be derivatized to form O-acyl or O-allyl derivatives. The imidazole nitrogen of histidine may be derivatized to form N-im-benzylhistidine. Peptides may also be modified by phosphorylation, for example 3 amino phosphorylation and by glycosylation for example mannosylation.

Also included as chemically modified peptides are those which contain one or more naturally occurring amino acid derivatives of the twenty standard amino acids. For example, 4-hydroxyproline may be substituted for proline or homoserine may be substituted for serine.

Polynucleotides

The invention also relates to polynucleotide constructs comprising nucleic acid sequences which encode the four polypeptides or variants thereof. For example, a single nucleic acid molecule may be provided which encodes an ahpC polypeptide, a gsd polypeptide, a p12 polypeptide and an mpa polypeptide. These four polypeptides may be encoded in any order in the nucleic acid molecule, but are preferably provided in the order ahpC-gsd-p12-mpa. For example, a polynucleotide of the invention may encode any of the polypeptides or fusion proteins described above.

The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or purified form.

A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

In one embodiment, therefore, a polynucleotide of the invention comprises an ahpC gene sequence, a gsd gene sequence, a p12 gene sequence and an mpa gene sequence. Suitable gene sequences are provided in SEQ ID Nos 1, 3, 5, 7, 9, 11, 13 and 15. A suitable ahpC, gsd, p12 or mpa sequence may alternatively be a variant of one of these specific sequences. For example, a variant may be a substitution, deletion or addition variant of any of the above nucleic acid sequences. A variant of one of the four genes may comprise 1, 2, 3, 4, 5, up to 10, up to 20, up to 30, up to 40, up to 50, up to 75 or more nucleic acid substitutions and/or deletions from the sequences given in the sequence listing.

Suitable variants may be at least 70% homologous to a MAP polynucleotide of the invention, preferably at least 80 or 90% and more preferably at least 95%, 97% or 99% homologous thereto. Methods of measuring homology are well known in the art and it will be understood by those of skill in the art that in the present context, homology is calculated on the basis of nucleic acid identity. Such homology may exist over a region of at least 15, preferably at least 30, for instance at least 40, 60, 100, 200 or more contiguous nucleotides. Such homology may exist over the entire length of the unmodified MAP polynucleotide sequence.

Methods of measuring polynucleotide homology or identity are known in the art. For example the UWGCG Package provides the BESTFIT program which can be used to calculate homology (e.g. used on its default settings) (Devereux et al (1984) Nucleic Acids Research 12, p 387-395).

The PILEUP and BLAST algorithms can also be used to calculate homology or line up sequences (typically on their default settings), for example as described in Altschul S. F. (1993) J Mol Evol 36:290-300; Altschul, S. F et al (1990) J Mol Biol 215:403-10.

Software for performing BLAST analysis is publicly available through the National Centre for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89:10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90:5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologues typically hybridize with the relevant polynucleotide at a level significantly above background. The signal level generated by the interaction between the homologue and the polynucleotide is typically at least 10 fold, preferably at least 100 fold, as intense as "background hybridisation". The intensity of interaction may be measured, for example, by radiolabelling the probe, e.g. with $^{32}$P. Selective hybridisation is typically achieved using conditions of medium to high stringency, (for example, 0.03M sodium chloride and 0.003M sodium citrate at from about 50° C. to about 60° C.

Stringent hybridization conditions can include 50% formamide, 5×Denhardt's Solution, 5×SSC, 0.1% SDS and 100 µg/ml denatured salmon sperm DNA and the washing conditions can include 2×SSC, 0.1% SDS at 37° C. followed by 1×SSC, 0.1% SDS at 68° C. Defining appropriate hybridization conditions is within the skill of the art. See, e.g., Sambrook et al., supra.

The homologue may differ from a sequence in the relevant polynucleotide by less than 3, 5, 10, 15, 20 or more mutations (each of which may be a substitution, deletion or insertion). These mutations may be measured over a region of at least 30, for instance at least 40, 60 or 100 or more contiguous nucleotides of the homologue.

In one embodiment, a variant sequence may vary from the specific sequences given in the sequence listing by virtue of the redundancy in the genetic code. The DNA code has 4 primary nucleic acid residues (A, T, C and G) and uses these to "spell" three letter codons which represent the amino acids the proteins encoded in an organism's genes. The linear sequence of codons along the DNA molecule is translated into the linear sequence of amino acids in the protein(s) encoded by those genes. The code is highly degenerate, with 61 codons coding for the 20 natural amino acids and 3 codons representing "stop" signals. Thus, most amino acids are coded for by more than one codon—in fact several are coded for by four or more different codons. A variant polynucleotide of the invention may therefore encode the same polypeptide sequence as another polynucleotide of the invention, but may have a different nucleic acid sequence due to the use of different codons to encode the same amino acids.

In one embodiment the coding sequence of the polynucleotide construct may be optimised to more closely resemble the codon usage of highly expressed genes in mammalian cells. Where more than one codon is available to code for a given amino acid, it has been observed that the codon usage patterns of organisms are highly non-random. Different species show a different bias in their codon selection and, furthermore, utilization of codons may be markedly different in a single species between genes which are expressed at high and low levels. This bias is different in viruses, plants, bacteria and mammalian cells, and some species show a stronger bias away from a random codon selection than others.

For example, humans and other mammals are less strongly biased than certain bacteria or viruses. For these reasons, it is possible that, for example a mycobacterial gene expressed in mammalian cells will have an inappropriate distribution of codons for efficient expression. It is believed that the presence in a heterologous DNA sequence of clusters of codons which are rarely observed in the host in which expression is to occur, is predictive of low heterologous expression levels in that host.

In the polynucleotide of the invention, the codon usage pattern may therefore be altered from that found naturally in MAP to more closely represent the codon bias of the target organism, e.g. a mammal, especially a human. The "codon usage coefficient" is a measure of how closely the codon pattern of a given polynucleotide sequence resembles that of a target species. Codon frequencies can be derived from literature sources for the highly expressed genes of many species (see e.g. Nakamura et. al. Nucleic Acids Research 1996, 24:214-215). The codon frequencies for each of the 61 codons (expressed as the number of occurrences occurrence per 1000 codons of the selected class of genes) are normalised for each of the twenty natural amino acids, so that the value for the most frequently used codon for each amino acid is set to 1 and the frequencies for the less common codons are scaled to lie between zero and 1. Thus each of the 61 codons is assigned a value of 1 or lower for the highly expressed genes of the target species. In order to calculate a codon usage coefficient for a specific polynucleotide, relative to the highly expressed genes of that species, the scaled value for each codon of the specific polynucleotide are noted and the geometric mean of all these values is taken (by dividing the sum of the natural logs of these values by the total number of codons and take the anti-log). The coefficient will have a value between zero and 1 and the higher the coefficient the more codons in the polynucleotide are "frequently used codons". If a polynucleotide sequence has a codon usage coefficient of 1, all of the codons are "most frequent" codons for highly expressed genes of the target species.

According to the present invention, the codon usage pattern of the polynucleotide of the invention will preferably exclude codons with a relative synonymous codon usage (RSCU) value of less than 0.2 in highly expressed genes of the target organism. A RSCU value is the observed number of codons divided by the number expected if all codons for that amino acid were used equally frequently. The polynucleotide of the invention will generally have a codon usage coefficient for highly expressed human genes of greater than 0.3, preferably greater than 0.4, most preferably greater than 0.5. Codon usage tables for human can also be found in GenBank.

It can thus be seen that the particular polynucleotide sequence which encodes a polypeptide of the invention may be altered to optimise the codons based on the species to be treated. As an example of this, the MAP sequences given in SEQ ID Nos: 1, 5, 9 and 13 have been codon optimised for human use in the polynucleotides of SEQ ID Nos: 3, 7, 11 and 17. Such modifications may improve the ability of such polynucleotides to express their encoded proteins in a human cell.

As explained above in relation to polypeptides, the polynucleotides of the invention may also be modified to disable or remove potential cross-reacting epitopes in the encoded polypeptide.

Polynucleotide "fragments" according to the invention may be made by truncation, e.g. by removal of one or more nucleotides from one or both ends of a polynucleotide. Up to 10, up to 20, up to 30, up to 40, up to 50, up to 75, up to 100, up to 200 or more amino acids may be removed from the 3' and/or 5' end of the polynucleotide in this way. Fragments may also be generated by one or more internal deletions. For example, a variant of the invention may encode a polypeptide that consists of or comprises two or more epitope regions from a full length polypeptide of the invention in the absence of non-epitope amino acids. Preferably a fragment of an ahpC, gsd, p12 or mpa polynucleotide sequence comprises at least one region encoding an epitope capable of inducing an immune response against the unmodified MAP polypeptide. Such fragments may be derived from a sequence of SEQ ID NO: 1, 3, 5, 7, 9, 11, 13 or 15 or may be derived from a variant polynucleotide as described herein. Preferably such fragments are between 24 and 500 residues in length, e.g. 24 to 400, 24 to 300, 24 to 100, 100 to 200 or 200 to 400 residues. Alternatively, fragments of the invention may be longer sequences, for example comprising at least 50%, at least 60%, at least 70%, at least 80% or at least 90% of a full length polynucleotide of the invention.

A peptide of the invention may thus be produced from or delivered in the form of a polynucleotide which encodes, and is capable of expressing, it. Polynucleotides of the invention can be synthesised according to methods well known in the art, as described by way of example in Sambrook et al (1989, Molecular Cloning—a laboratory manual; Cold Spring Harbor Press). Substantially pure antigen preparations can be obtained using standard molecular biological tools. That is, polynucleotide sequences coding for the above-described moieties can be obtained using recombinant methods, such as by screening cDNA and genomic libraries from cells expressing an antigen, or by deriving the coding sequence for a polypeptide from a vector known to include the same. Furthermore, the desired sequences can be isolated directly from cells and tissues containing the same, using standard techniques, such as phenol extraction and PCR of cDNA or genomic DNA. See, e.g., Sambrook et al., supra, for a description of techniques used to obtain and isolate DNA. Polynucleotide sequences can also be produced synthetically, rather than cloned.

Yet another convenient method for isolating specific nucleic acid molecules is by the polymerase chain reaction (PCR). Mullis et al. (1987) Methods Enzymol. 155:335-350. This technique uses DNA polymerase, usually a thermostable DNA polymerase, to replicate a desired region of DNA. The region of DNA to be replicated is identified by oligonucleotides of specified sequence complementary to opposite ends and opposite strands of the desired DNA to prime the replication reaction. The product of the first round of replication is itself a template for subsequent replication, thus repeated successive cycles of replication result in geometric amplification of the DNA fragment delimited by the primer pair used.

Once the sequences have been obtained, they may be linked together to provide a nucleic acid molecule using standard cloning or molecular biology techniques. Alternatively, the sequences can be produced synthetically, rather than cloned. The nucleotide sequence can be designed with the appropriate codons for the particular amino acid sequence desired. As explained herein, one will generally select preferred codons for the intended host in which the sequence will be expressed. The complete sequence can then be assembled from overlapping oligonucleotides prepared by standard methods and assembled into a complete coding sequence.

Vectors

The nucleic acid molecules of the present invention may be provided in the form of an expression cassette which includes control sequences operably linked to the inserted sequence, thus allowing for expression of the polypeptide of the invention in vivo in a targeted subject species. These expression cassettes, in turn, are typically provided within vectors (e.g., plasmids or recombinant viral vectors) which are suitable for use as reagents for nucleic acid immunization. Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a polypeptide of the invention.

The present invention thus includes expression vectors that comprise such polynucleotide sequences. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

Thus, a polypeptide of the invention may be provided by delivering such a vector to a cell and allowing transcription from the vector to occur. Preferably, a polynucleotide of the invention or for use in the invention in a vector is operably linked to a control sequence which is capable of providing for the expression of the coding sequence by the host cell, i.e. the vector is an expression vector.

"Operably linked" refers to an arrangement of elements wherein the components so described are configured so as to perform their usual function. Thus, a given regulatory sequence, such as a promoter, operably linked to a nucleic acid sequence is capable of effecting the expression of that sequence when the proper enzymes are present. The promoter need not be contiguous with the sequence, so long as it functions to direct the expression thereof. Thus, for example, intervening untranslated yet transcribed sequences can be present between the promoter sequence and the nucleic acid sequence and the promoter sequence can still be considered "operably linked" to the coding sequence.

A number of expression systems have been described in the art, each of which typically consists of a vector containing a gene or nucleotide sequence of interest operably linked to expression control sequences. These control sequences include transcriptional promoter sequences and transcriptional start and termination sequences. The vectors of the invention may be for example, plasmid, virus or phage vectors provided with an origin of replication, optionally a promoter for the expression of the said polynucleotide and optionally a regulator of the promoter. A "plasmid" is a vector in the form of an extrachromosomal genetic element. The vectors may contain one or more selectable marker genes, for example an ampicillin resistance gene in the case of a bacterial plasmid or a resistance gene for a fungal vector. Vectors may be used in vitro, for example for the production of DNA or RNA or used to transfect or transform a host cell, for example, a mammalian host cell. The vectors may also be adapted to be used in vivo, for example to allow in vivo expression of the polypeptide.

A "promoter" is a nucleotide sequence which initiates and regulates transcription of a polypeptide-encoding polynucleotide. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is repressed by an analyte, cofactor, regulatory protein, etc.), and constitutive promoters. It is intended that the term "promoter" or "control element" includes full-length promoter regions and functional (e.g., controls transcription or translation) segments of these regions.

Promoters and other expression regulation signals may be selected to be compatible with the host cell for which expression is designed. For example, yeast promoters include S. cerevisiae GAL4 and ADH promoters, S. pombe nmt1 and adh promoter. Mammalian promoters, such as β-actin promoters, may be used. Tissue-specific promoters are especially preferred. Mammalian promoters include the metallothionein promoter which can be induced in response to heavy metals such as cadmium.

In one embodiment a viral promoter is used to drive expression from the polynucleotide. Typical viral promoters for mammalian cell expression include the SV40 large T antigen promoter, adenovirus promoters, the Moloney murine leukaemia virus long terminal repeat (MMLV LTR), the mouse mammary tumor virus LTR promoter, the rous sarcoma virus (RSV) LTR promoter, the SV40 early promoter, the human cytomegalovirus (CMV) IE promoter, adenovirus, including the adenovirus major late promoter (Ad MLP), HSV promoters (such as the HSV IE promoters), or HPV promoters, particularly the HPV upstream regulatory region (URR). All these promoters are readily available in the art.

In one embodiment, the promoter is a Cytomegalovirus (CMV) promoter. A preferred promoter element is the CMV immediate early (IE) promoter devoid of intron A, but including exon 1. Thus the expression from the polynucleotide may be under the control of hCMV IE early promoter. Expression vectors using the hCMV immediate early promoter include for example, pWRG7128, and pBC12/CMV and pJW4303. A hCMV immediate early promoter sequence can be obtained using known methods. A native hCMV immediate early promoter can be isolated directly from a sample of the virus, using standard techniques. U.S. Pat. No. 5,385,839, for example, describes the cloning of a hCMV promoter region. The sequence of a hCMV immediate early promoter is available at Genbank #M60321 (hCMV Towne strain) and X17403 (hCMV Ad169 strain). A native sequence could therefore be isolated by PCR using PCR primers based on the known sequence. See e.g Sambrook et al, supra, for a description of techniques used to obtain and isolate DNA. A suitable hCMV promoter sequence could also be isolated from an existing plasmid vector. Promoter sequences can also be produced synthetically.

A polynucleotide, expression cassette or vector of the invention may comprise an untranslated leader sequence. In general the untranslated leader sequence has a length of from about 10 to about 200 nucleotides, for example from about 15 to 150 nucleotides, preferably 15 to about 130 nucleotides. Leader sequences comprising, for example, 15, 50, 75 or 100 nucleotides may be used. Generally a functional untranslated leader sequence is one which is able to provide a translational start site for expression of a coding sequence in operable linkage with the leader sequence.

Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook et al., supra, as well as a bovine growth hormone terminator sequence. Introns, containing splice donor and acceptor sites, may also be designed into the expression cassette or vector.

Expression systems often include transcriptional modulator elements, referred to as "enhancers". Enhancers are broadly defined as a cis-acting agent, which when operably linked to a promoter/gene sequence, will increase transcription of that gene sequence. Enhancers can function from positions that are much further away from a sequence of interest than other expression control elements (e.g. promoters), and may operate when positioned in either orientation relative to the sequence of interest. Enhancers have been identified from a number of viral sources, including polyoma virus, BK virus, cytomegalovirus (CMV), adenovirus, simian virus 40 (SV40), Moloney sarcoma virus, bovine papilloma virus and Rous sarcoma virus. Examples of suitable enhancers include the SV40 early gene enhancer, the enhancer/promoter derived from the long terminal repeat (LTR) of the Rous Sarcoma Virus, and elements derived from human or murine CMV, for example, elements included in the CMV intron A sequence.

A polynucleotide, expression cassette or vector according to the present invention may additionally comprise a signal peptide sequence. The signal peptide sequence is generally inserted in operable linkage with the promoter such that the signal peptide is expressed and facilitates secretion of a polypeptide encoded by coding sequence also in operable linkage with the promoter.

Typically a signal peptide sequence encodes a peptide of 10 to 30 amino acids for example 15 to 20 amino acids. Often the amino acids are predominantly hydrophobic. In a typical situation, a signal peptide targets a growing polypeptide chain bearing the signal peptide to the endoplasmic reticulum of the expressing cell. The signal peptide is cleaved off in the endoplasmic reticulum, allowing for secretion of the polypeptide via the Golgi apparatus.

Nucleic acids encoding for polypeptides known to display antiviral or antibacterial activity, immunomodulatory molecules such as cytokines (e.g. TNF-alpha, interferons such as IL-6, and IL-2, interferons, colony stimulating factors such as GM-CSF), adjuvants and co-stimulatory and accessory molecules (B7-1, B7-2) may be included in a polynucleotide, expression cassette or vector of the invention. Alternatively, such polypeptides may be provided separately, for example in a formulation comprising a molecule of the invention, or may be administered simultaneously, sequentially or separately with a composition of the invention. Concurrent provision of an immunomodulatory molecule and a polypeptide of the invention at a site in vivo may enhance the generation of specific effectors which may help to enhance the immune response. The degree of enhancement of the immune response may be dependent upon the specific immunostimulatory molecules and/or adjuvants used because different immunostimulatory molecules may elicit different mechanisms for enhancing and/or modulating the immune response. By way of example, the different effector mechanisms/immunomodulatory molecules include but are not limited to augmentation of help signal (IL-2), recruitment of professional APC (GM-CSF), increase in T cell frequency (IL-2), effect on antigen processing pathway and MHC expression (IFN-gamma and TNF-alpha) and diversion of immune response away from the Th1 response and towards a Th2 response. Unmethylated CpG containing oligonucleotides are also preferential inducers of a Th1 response and are suitable for use in the present invention.

In some embodiments, the polynucleotide, expression cassette or vector will encode an adjuvant, or an adjuvant will otherwise be provided. As used herein, the term "adjuvant" refers to any material or composition capable of specifically or non-specifically altering, enhancing, directing, redirecting, potentiating or initiating an antigen-specific immune response.

A suitable adjuvant may be an ADP-ribosylating bacterial toxin. These include diphtheria toxin (DT), pertussis toxin (PT), cholera toxin (CT), the *E. coli* heat labile toxins (LT1 and LT2), *Pseudomonas* endotoxin A, *Pseudomonas* exotoxin S, *B. cereus* exoenzyme, *B. sphaericus* toxin, *C. botulinum* C2 and C3 toxins, *C. limosum* exoenzyme, as well as toxins from *C. perfringens, C. spiriforma* and *C. difficile* and *Staphylococcus aureus* EDIN. Most ADP-ribosylating bacterial toxins contain A and B subunits.

Polynucleotides of interest may be used in vitro or in vivo in the production of a peptide of the invention. Such polynucleotides may be administered or used in the manufacture of a medicament for the treatment of Crohn's disease or another disease or condition characterised by the expression of MAP.

Gene therapy and nucleic acid immunization are approaches which provide for the introduction of a nucleic acid molecule encoding one or more selected antigens into a host cell for the in vivo expression of the antigen or antigens. Methods for gene delivery are known in the art. See, e.g., U.S. Pat. Nos. 5,399,346, 5,580,859 and 5,589,466. The nucleic acid molecule can be introduced directly into the recipient subject, such as by standard intramuscular or intradermal injection; transdermal particle delivery; inhalation; topically, or by oral, intranasal or mucosal modes of administration. The molecule alternatively can be introduced ex vivo into cells which have been removed from a subject. In this latter case, cells containing the nucleic acid molecule of interest are re-introduced into the subject such that an immune response can be mounted against the antigen encoded by the nucleic acid molecule. The nucleic acid molecules used in such immunization are generally referred to herein as "nucleic acid vaccines."

Each of these delivery techniques requires efficient expression of the nucleic acid in the transfected cell, to provide a sufficient amount of the therapeutic or antigenic gene product. Several factors are known to affect the levels of expression obtained, including transfection efficiency, and the efficiency with which the gene or sequence of interest is transcribed and the mRNA translated.

The agent produced by a host cell may be secreted or may be contained intracellularly depending on the polynucleotide and/or the vector used. As will be understood by those of skill in the art, expression vectors containing the polynucleotides of the invention can be designed with signal sequences which direct secretion of the polypeptide expressed from the vector through a particular prokaryotic or eukaryotic cell membrane.

The vectors and expression cassettes of the present invention may be administered directly as "a naked nucleic acid construct", preferably further comprising flanking sequences homologous to the host cell genome. As used herein, the term "naked DNA" refers to a vector such as a plasmid comprising a polynucleotide of the present invention together with a short promoter region to control its production. It is called "naked" DNA because the vectors are not carried in any delivery vehicle. When such a vector enters a host cell, such as a eukaryotic cell, the proteins it encodes are transcribed and translated within the cell.

The vector of the invention may thus be a plasmid vector, that is, an autonomously replicating, extrachromosomal circular or linear DNA molecule. The plasmid may include additional elements, such as an origin of replication, or selector genes. Such elements are known in the art and can be included using standard techniques. Numerous suitable expression plasmids are known in the art. For example, one suitable plasmid is pSG2. This plasmid was originally isolated from *Streptomyces ghanaensis*. The length of 13.8 kb, single restriction sites for HindIII, EcoRV and PvuII and the possibility of deleting non-essential regions of the plasmid make pSG2 a suitable basic replicon for vector development.

Alternatively, the vectors of the present invention may be introduced into suitable host cells using a variety of viral techniques which are known in the art, such as for example infection with recombinant viral vectors such as retroviruses, herpes simplex viruses and adenoviruses.

In one embodiment, the vector itself may be a recombinant viral vector. Suitable recombinant viral vectors include but are not limited to adenovirus vectors, adeno-associated viral (AAV) vectors, herpes-virus vectors, a retroviral vector, lentiviral vectors, baculoviral vectors, pox viral vectors or parvovirus vectors. In the case of viral vectors, administration of the polynucleotide is mediated by viral infection of a target cell.

A number of viral based systems have been developed for transfecting mammalian cells.

For example, a selected recombinant nucleic acid molecule can be inserted into a vector and packaged as retroviral particles using techniques known in the art. The recombinant virus can then be isolated and delivered to cells of the subject either in vivo or ex vivo. Retroviral vectors may be based upon the Moloney murine leukaemia virus (Mo-MLV). In a retroviral vector, one or more of the viral genes (gag, pol & env) are generally replaced with the gene of interest.

A number of adenovirus vectors are known. Adenovirus subgroup C serotypes 2 and 5 are commonly used as vectors. The wild type adenovirus genome is approximately 35 kb of which up to 30 kb can be replaced with foreign DNA. There are four early transcriptional units (E1, E2, E3 & E4), which have regulatory functions, & a late transcript, which codes for structural proteins. Adenovirus vectors may have the E1 and/or E3 gene inactivated. The missing gene(s) may then be supplied in trans either by a helper virus, plasmid or integrated into a helper cell genome. Adenovirus vectors may use an E2a temperature sensitive mutant or an E4 deletion. Minimal adenovirus vectors may contain only the inverted terminal repeats (ITRs) & a packaging sequence around the transgene, all the necessary viral genes being provided in trans by a helper virus. Suitable adenoviral vectors thus include Ad5 vectors and simian adenovirus vectors.

Viral vectors may also be derived from the pox family of viruses, including vaccinia viruses and avian poxvirus such as fowlpox vaccines. For example, modified vaccinia virus Ankara (MVA) is a strain of vaccinia virus which does not replicate in most cell types, including normal human tissues. A recombinant MVA vector may therefore be used to deliver the polypeptide of the invention.

Addition types of virus such as adeno-associated virus (AAV) and herpes simplex virus (HSV) may also be used to develop suitable vector systems.

As an alternative to viral vectors, liposomal preparations can alternatively be used to deliver the nucleic acid molecules of the invention. Useful liposomal preparations include cationic (positively charged), anionic (negatively charged) and neutral preparations, with cationic liposomes particularly preferred. Cationic liposomes may mediate intracellular delivery of plasmid DNA and mRNA.

As another alternative to viral vector systems, the nucleic acid molecules of the present invention may be encapsulated, adsorbed to, or associated with, particulate carriers. Suitable particulate carriers include those derived from polymethyl methacrylate polymers, as well as PLG microparticles derived from poly(lactides) and poly(lactide-co-glycolides). Other particulate systems and polymers can also be used, for example, polymers such as polylysine, polyarginine, polyornithine, spermine, spermidine, as well as conjugates of these molecules.

In one embodiment, the vector may be a targeted vector, that is a vector whose ability to infect or transfect or transduce a cell or to be expressed in a host and/or target cell is restricted to certain cell types within the host subject, usually cells having a common or similar phenotype.

Preferably, a vector of the invention encodes an ahpC, a gsd, a p12 and an mpa polypeptide. As explained above, these four polypeptides may be expressed together as a single fusion protein molecule, or may be expressed in two or more separate polypeptides, each comprising one or more of the individual components. The vector of the invention may thus comprise a single expression cassette, from which a single polypeptide sequence can be expressed. Alternatively, a vector of the invention may comprise two or more expression cassettes each capable of expressing a different polypeptide, such that the vector as a whole is capable of expressing all four required polypeptides. In one embodiment, a vector of the invention may express all four required polypeptides separately as separate polypeptide molecules. Where the polypeptides are expressed from more than one locus in the vector, or are expressed as multiple separate molecules, the expression of the multiple sequences is preferably coordinated such that all four polypeptides are expressed together. For example, the same or similar promoters may be used to control expression of the various components. Inducible promoters may be used so that expression of the various polypeptide components can be coordinated.

Cell Lines

The invention also includes cells that have been modified to express a peptide of the invention. Such cells include transient, or preferably stable higher eukaryotic cell lines, such as mammalian cells or insect cells, lower eukaryotic cells, such as yeast or prokaryotic cells such as bacterial cells. Particular examples of cells which may be modified by insertion of vectors or expression cassettes encoding for a peptide of the invention include mammalian HEK293T, CHO, HeLa and COS cells. Preferably the cell line selected will be one which is not only stable, but also allows for mature glycosylation and cell surface expression of a polypeptide. Expression may be achieved in transformed oocytes. A suitable peptide may be expressed in cells of a transgenic non-human animal, preferably a mouse. A transgenic non-human animal expressing a peptide of the invention is included within the scope of the invention. A peptide of the invention may also be expressed in *Xenopus laevis* oocytes or melanophores.

Such cell lines of the invention may be cultured using routine methods to produce a polypeptide of the invention, or may be used therapeutically or prophylactically to deliver polypeptides of the invention to a subject. For example, cell lines capable of secreting a polypeptide of the invention may be administered to a subject. Alternatively, polynucleotides, expression cassettes or vectors of the invention may be administered to a cell from a subject ex vivo and the cell then returned to the body of the subject.

For example, methods for the ex vivo delivery and reimplantation of transformed cells into a subject are known (e.g., dextran-mediated transfection, calcium phosphate precipitation, electroporation, and direct microinjection into nuclei).

Antibodies

The present invention also extends to antibodies (monoclonal or polyclonal) and their antigen-binding fragments (e.g. F(ab)2, Fab and Fv fragments i.e. fragments of the "variable" region of the antibody, which comprises the antigen binding site) directed to peptides as defined hereinbefore, i.e. which bind to epitopes present on the peptides and thus bind selectively and specifically to such peptides, and which may be used in the methods of the invention. For example, a polyclonal antibody may be produced which has a broad spectrum effect against a variety of epitopes on a polypeptide of the invention.

Pharmaceutical Compositions

Formulation of a composition comprising a molecule of the invention, such as a polynucleotide, expression cassette, vector, polypeptide, cell or antibody as described above, can be carried out using standard pharmaceutical formulation chemistries and methodologies all of which are readily available to the reasonably skilled artisan. For example, compositions containing one or more molecules of the invention can be combined with one or more pharmaceutically acceptable excipients or vehicles. Auxiliary substances, such as wetting or emulsifying agents, pH buffering substances and the like, may be present in the excipient or vehicle. These excipients, vehicles and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid, glycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in Remington's Pharmaceutical Sciences (Mack Pub. Co., N.J. 1991).

Such compositions may be prepared, packaged, or sold in a form suitable for bolus administration or for continuous administration. Injectable compositions may be prepared, packaged, or sold in unit dosage form, such as in ampoules or in multi-dose containers containing a preservative. Compositions include, but are not limited to, suspensions, solutions, emulsions in oily or aqueous vehicles, pastes, and implantable sustained-release or biodegradable formulations. Such compositions may further comprise one or more additional ingredients including, but not limited to, suspending, stabilizing, or dispersing agents. In one embodiment of a composition for parenteral administration, the active ingredient is provided in dry (for e.g., a powder or granules) form for reconstitution with a suitable vehicle (e.g., sterile pyrogen-free water) prior to parenteral administration of the reconstituted composition. The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Other parentally-administrable compositions which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Certain facilitators of nucleic acid uptake and/or expression ("transfection facilitating agents") can also be included in the compositions, for example, facilitators such as bupivacaine, cardiotoxin and sucrose, and transfection facilitating vehicles such as liposomal or lipid preparations that are routinely used to deliver nucleic acid molecules. Anionic and neutral liposomes are widely available and well known for delivering nucleic acid molecules (see, e.g., Liposomes: A Practical Approach, (1990) RPC New Ed., IRL Press). Cationic lipid preparations are also well known vehicles for use in delivery of nucleic acid molecules. Suitable lipid preparations include DOTMA (N-[1-(2,3-dioleyloxy)propyl]-N,N, N-trimethylammonium chloride), available under the tradename Lipofectin™, and DOTAP (1,2-bis(oleyloxy)-3-(trimethylammonio)propane), see, e.g., Felgner et al. (1987) Proc. Natl. Acad. Sci. USA 84:7413-7416; Malone et al. (1989) Proc. Natl. Acad. Sci. USA 86:6077-6081; U.S. Pat. Nos. 5,283,185 and 5,527,928, and International Publication Nos WO 90/11092, WO 91/15501 and WO 95/26356. These cationic lipids may preferably be used in association with a neutral lipid, for example DOPE (dioleyl phosphatidylethanolamine). Still further transfection-facilitating compositions that can be added to the above lipid or liposome preparations include spermine derivatives (see, e.g., International Publication No. WO 93/18759) and membrane-permeabilizing compounds such as GALA, Gramicidine S and cationic bile salts (see, e.g., International Publication No. WO 93/19768).

Alternatively, the nucleic acid molecules of the present invention may be encapsulated, adsorbed to, or associated with, particulate carriers. Suitable particulate carriers include those derived from polymethyl methacrylate polymers, as well as PLG microparticles derived from poly(lactides) and poly(lactide-co-glycolides). See, e.g., Jeffery et al. (1993) Pharm. Res. 10:362-368. Other particulate systems and polymers can also be used, for example, polymers such as polylysine, polyarginine, polyornithine, spermine, spermidine, as well as conjugates of these molecules.

The formulated compositions will include an amount of the molecule (e.g. vector) of interest which is sufficient to mount an immunological response. An appropriate effective amount can be readily determined by one of skill in the art. Such an amount will fall in a relatively broad range that can be determined through routine trials. The compositions may contain from about 0.1% to about 99.9% of the vector and can be administered directly to the subject or, alternatively, delivered ex vivo, to cells derived from the subject, using methods known to those skilled in the art.

Therapeutic Methods

The present invention relates to immunogenic molecules which are intended to direct an immune response against MAP. The compositions of the invention can thus be used in the treatment or prevention of infection by MAP, or in the treatment or prevention of any disease, condition or symptom which is associated with MAP infection, that is any disease condition or symptom which is a direct or indirect result of MAP infection, or which results from a disease or condition to which the presence of MAP contributes. MAP is known to be linked to numerous specific medical conditions, such as chronic inflammation of the intestine, including inflammatory bowel disease and as well as Irritable Bowel Syndrome. For example, MAP infection can cause chronic enteritis, such as Johne's disease (*paratuberculosis*) in livestock and Crohn's disease and Irritable Bowel Syndrome in humans. The compositions of the invention may therefore be used in the prevention or treatment of any of these specific conditions.

Accordingly, the present invention relates to a polypeptide, polynucleotide, expression cassette, vector, cell, antibody or composition of the invention for use in a method of therapy, in particular in a method or treating or preventing a disease, disorder or symptoms associated with or caused by a MAP infection. These molecules of the invention may thus also be used in the manufacture of a medicament for treating or preventing such a disease, disorder or condition. In particular, the molecules of the invention are proposed for the treatment or prevention of a chronic inflammation of the intestine, preferably in a mammal such as a human, cow, sheep or goat. The invention thus also provides a method of treating or preventing any such disease, disorder or symptom comprising administering to a subject in need thereof a polypeptide, polynucleotide, expression cassette, vector, cell, antibody or composition of the invention.

The present invention is broadly applicable to vaccination methods and is relevant to the development of prophylactic and/or therapeutic vaccines (including immunotherapeutic vaccines). It is to be appreciated that all references herein to treatment include curative, palliative and prophylactic treatment.

According to the present invention, a polynucleotide, vector, polypeptide or other molecule of the invention may be employed alone as part of a composition, such as but not limited to a pharmaceutical composition or a vaccine composition or an immunotherapeutic composition to prevent and/or treat a condition associated with MAP infection. The administration of the composition may be for either "prophylactic" or "therapeutic" purpose. As used herein, the term "therapeutic" or "treatment" includes any of following: the prevention of infection or reinfection; the reduction or elimination of symptoms; and the reduction or complete elimination of a pathogen. Treatment may be effected prophylactically (prior to infection) or therapeutically (following infection).

Prophylaxis or therapy includes but is not limited to eliciting an effective immune response to a polypeptide of the invention and/or alleviating, reducing, curing or at least partially arresting symptoms and/or complications resulting from or associated with a MAP infection. When provided prophylactically, the composition of the present invention is typically provided in advance of any symptom. The prophylactic administration of the composition of the present invention is to prevent or ameliorate any subsequent infection or disease. When provided therapeutically, the composition of the present invention is typically provided at or shortly after the onset of a symptom of infection or disease. Thus the composition of the present invention may be provided either prior to the anticipated exposure to MAP or onset of the associated disease state or after the initiation of an infection or disease.

Subject to be Treated

The present invention relates in particular to the treatment or prevention of diseases or other conditions which are associated with infection by MAP. These treatments may be used on any animal which is susceptible to infection by MAP.

The subject to be treated may be any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The terms do not denote a particular age. Thus, both adult and newborn individuals are intended to be covered. The methods described herein are intended for use in any of the above vertebrate species, since the immune systems of all of these vertebrates operate similarly. If a mammal, the subject will preferably be a human, but may also be a domestic livestock, laboratory subject or pet animal.

The subject to be treated may thus be any vertebrate that is susceptible to infection by MAP. Numerous animals have been shown in the art to be capable of such infection, including livestock such as cattle, goat and sheep, primates such as macaques and humans, other mammals including alpaca, antelope, as, elk, horses, deer, dogs, gerbils and rabbits, and birds including the chicken. The compositions of the present invention may thus be used in the treatment of any such species.

Combined Therapy

In one instance, a molecule of the invention may be used in combination with another molecule, such as another polynucleotide, vector or polypeptide, preferably another therapeutic agent. The therapeutic agent may be, for example an agent which has activity against MAP, or an agent used in the treatment of a condition which is associated with MAP infection. The molecule of the invention is preferably administered in an amount which is sufficient to augment the anti-MAP effects of the other therapeutic agent or vice versa. Numerous other agents may be used in the treatment of MAP or conditions which are associated with MAP infection. These include the rifamycins such as rifabutin and rifaximin, claritliromycin and other macrolides. Various anti tuberculosis drugs may also be used.

The other therapeutic agent may be an agent which potentiates the effects of the molecule of the invention. For example, the other agent may be an immunomodulatory molecule or an adjuvant which enhances the immune response to the polypeptide of the invention. Alternatively, the other molecule may increase the susceptibility of MAP present in the subject to attack, such as attack from the immune system.

In one embodiment, therefore, a molecule of the invention is used for therapy in combination with one or more other therapeutic agents.

The two molecules may be administered separately, simultaneously or sequentially. The two may be administered in the same or different compositions. Accordingly, in a method of the invention, the subject may also be treated with a further therapeutic agent.

A composition may therefore be formulated which comprises a molecule of the invention and also one or more other therapeutic molecules. For example, a vector of the invention may be formulated with another vector which encodes one or more other antigens or therapeutic molecules. A vector of the invention may alternatively be formulated with one or more therapeutic proteins.

A composition of the invention may alternatively by used simultaneously, sequentially or separately with one or more other therapeutic conditions as part of a combined treatment. Thus the invention also provides the use of a molecule, such as a polypeptide, polynucleotide, vector or host cell of the invention, in the manufacture of one or more medicament(s) for the treatment or prevention of MAP infection or a disease, condition or symptom associated with MAP infection as described herein.

Delivery Methods

Once formulated the compositions can be delivered to a subject in vivo using a variety of known routes and techniques. For example, a composition can be provided as an injectable solution, suspension or emulsion and administered via parenteral, subcutaneous, epidermal, intradermal, intramuscular, intraarterial, intraperitoneal, intravenous injection using a conventional needle and syringe, or using a liquid jet injection system. Compositions can also be administered topically to skin or mucosal tissue, such as nasally, intratracheally, intestinal, rectally or vaginally, or provided as a finely divided spray suitable for respiratory or pulmonary administration. Other modes of administration include oral administration, suppositories, and active or passive transdermal delivery techniques. Particularly in relation to the present invention, compositions may be administered directly to the gastrointestinal tract.

Alternatively, the compositions can be administered ex vivo, for example delivery and reimplantation of transformed cells into a subject are known (e.g., dextran-mediated transfection, calcium phosphate precipitation, electroporation, and direct microinjection into nuclei).

Delivery Regimes

The compositions are administered to a subject in an amount that is compatible with the dosage formulation and that will be prophylactically and/or therapeutically effective. An appropriate effective amount will fall in a relatively broad range but can be readily determined by one of skill in the art by routine trials. The "Physicians Desk Reference" and "Goodman and Gilman's The Pharmacological Basis of Therapeutics" are useful for the purpose of determining the amount needed.

As used herein, the term "prophylactically or therapeutically effective dose" means a dose in an amount sufficient to elicit an immune response to one or more epitopes of a polypeptide of the invention and/or to alleviate, reduce, cure or at least partially arrest symptoms and/or complications from a disease, such as an inflammatory bowel disorder, which is associated with a MAP infection.

Prophylaxis or therapy can be accomplished by a single direct administration at a single time point or by multiple administrations, optionally at multiple time points. Administration can also be delivered to a single or to multiple sites. Those skilled in the art can adjust the dosage and concentration to suit the particular route of delivery. In one embodiment, a single dose is administered on a single occasion. In an alternative embodiment, a number of doses are administered to a subject on the same occasion but, for example, at different sites. In a further embodiment, multiple doses are administered on multiple occasions. Such multiple doses may be administered in batches, i.e. with multiple administrations at different sites on the same occasion, or may be administered individually, with one administration on each of multiple occasions (optionally at multiple sites). Any combination of such administration regimes may be used.

In one embodiment, different compositions of the invention may be administered at different sites or on different occasions as part of the same treatment regime. It is known that improved immune responses may be generated to an antigen by varying the vectors used to deliver the antigen. There is evidence that in some instances antibody and/or cellular immune responses may be improved by using two different vectors administered sequentially as a "prime" and a "boost".

For example, the same polynucleotide of the invention may be administered as a "prime" in one composition, and then subsequently administered as a "boost" in a different composition. The two vaccine compositions may differ in the choice of vector comprising the polynucleotide. For example, two or more of different vectors each selected from plasmid vectors, poxvirus vectors, adenovirus vectors or other vectors as described herein may be administered sequentially.

In one embodiment, a "prime" is effected by administering a polynucleotide of the invention, such as the Havilah polynucleotide of SEQ ID NO: 23, in a plasmid vector such as pSG2. A "boost" is then effected at a later time using a polynucleotide of the invention, such as the Havilah polynucleotide of SEQ ID NO: 23 in a poxvirus vector such as MVA.

In an alternative embodiment a "prime" is effected by administering a polynucleotide of the invention, such as the Havilah polynucleotide of SEQ ID NO: 23, in an adenovirus vector such as Ad5. A "boost" is then effected at a later time using a polynucleotide of the invention, such as the Havilah polynucleotide of SEQ ID NO: 23 in a poxvirus vector such as MVA.

In such a prime-boost protocol, one or more administrations of the prime and/or the boost may be performed. For example, the prime and/or boost step may be achieved using a single administration or using two or more administrations at different sites and/or on different occasions. In one embodiment, two administrations on different occasions are given for the prime step and a single administration on a later occasion is given for the boost step.

Different administrations may be performed on the same occasion, on the same day, one, two, three, four, five or six days apart, one, two, three, four or more weeks apart. Preferably, administrations are 1 to 5 weeks apart, more preferably 2 to 4 weeks apart, such as 2 weeks, 3 weeks or 4 weeks apart. The schedule and timing of such multiple administrations can be optimised for a particular composition or compositions by one of skill in the art by routine trials.

Dosages for administration will depend upon a number of factors including the nature of the composition, the route of administration and the schedule and timing of the administration regime. Suitable doses of a molecule of the invention may be in the order of up to 15 µg, up to 20 µg, up to 25 µg, up to 30 µg, up to 50 µg, up to 100 µg, up to 500 µg or more per administration. For some molecules of the invention, such as plasmids, the dose used may be higher, for example, up to 1 mg, up to 2 mg, up to 3 mg, up to 4 mg, up to 5 mg or higher. Such doses may be provided in a liquid formulation, at a concentration suitable to allow an appropriate volume for administration by the selected route. In the case of a viral vector, a dose of about $10^6$, $10^7$, $10^8$, $10^9$, $10^{10}$ or more pfu may be given per administration. For example, a dose of $10^9$ pfu or 25 µg of a vector of the invention may be administered in a 50 µl dose at multiple sites and/or on multiple occasions.

Kits

The invention also relates to a combination of components described herein suitable for use in a treatment of the invention which are packaged in the form of a kit in a container. Such kits may comprise a series of components to allow for a treatment of the invention. For example, a kit may comprise two or more different vectors of the invention, or one or more vectors of the invention and one or more additional therapeutic agents suitable for simultaneous administration, or for sequential or separate administration such as using a prime and boost protocol. The kit may optionally contain other suitable reagent(s), control(s) or instructions and the like.

Examples

1. Production of Havilah (HAV) Construct and Recombinant Vectors Expressing HAV A targeted bioinformatic analysis of the MAP genome was carried out and two secreted and two membrane bound components each related to the pathogenic phenotype were selected. These are AhpC, gsd, p12 and mpa. Three of these 4 components are 'seen' by antibody in sera from Crohn's disease patients as well as by sera from MAP infected C57/BL6 mice. Detailed epitope scans using the available databases revealed multiple predicted human class I and class II epitopes in the selected vaccine components. The peptides comprising these epitopes, when matched against the available human genome sequence, did not reveal any potential cross reacting antigens as potential targets for autoimmunity.

A construct consisting of a fusion of these four antigens was assembled from 40mer oligonucleotide precursors synthesized with optimal mammalian codon usage. Functional domains including potential cross-reacting human epitopes, lipid acylation sites and hydrophobic transmembrane regions were excluded. A monoclonal antibody recognition peptide was added to the C-terminus and a short human ubiquitin leader sequence to the N-terminus. This construct is referred to herein as Havilah and has the nucleic acid sequence given in SEQ ID NO: 23.

The Havilah (HAV) construct was cloned into the pSG2 expression vector and inserted by homologous recombination into the Modified Vaccinia Ankara (MVA) vector pMVA-GFP2 which carried a fluorescent marker. pMVA-GFP2 was used to transform MVA carrying a red marker at the target site for insertion, so that successful recombinants changed from red to green enabling them to be isolated using a fluorescence activated cell sorter. HAV was also inserted into the vector comprising replication defective human adenovirus 5. The rec.pSG2.HAV plasmid, rec.MVA.HAV, and rec.Ad5.hav were all shown to express the predicted 95 kDa HAV encoded polyprotein. The successful rec.pSG2.HAV, rec.MVA.HAV and rec.Ad5.HAV and corresponding control vectors were prepared in bulk, purified and stored ready for testing in vivo. E. coli were transformed with the individual components AhpC and mpa representing the upstream and downstream ends of HAV and the His-tagged recombinant proteins were purified. Libraries of synthetic 15 residue peptides spanning the entire amino acid sequences of Havilah were obtained (FIG. 4). The recombinant proteins and pools of the synthetic peptides were used to develop the ELISPOT and ELISA assays required to monitor the immune responses to the vaccine.

2. Safety and Immunogenicity of Vaccination Using pSG2.HAV then MVA.HAV

Two groups of 6 naïve 5 week old C57/BL6 female mice were isolator maintained. Their physical condition was monitored daily and body weights recorded twice weekly and at the end of the study. After an initial settle-in period of 7 days control Group 1 mice were prime vaccinated with 25 μg of pSG2 expression plasmid in 50 μl sterile buffered saline i.m. into each thigh. The experimental group received the same vaccination using recombinant pSG2.Hav plasmid expressing the Havilah construct. Ten days later Group 1 mice were boost vaccinated i.v. with 106 pfu Modified Vaccinia Ankara.GFP (MVA) vector alone. Group 2 mice received the same dose i.v. of recombinant MVA.Hav expressing the Havilah construct. At the end of the study 10 days later the mice were killed using a humane procedure. Spleen weights were recorded and spleen cells were obtained.

Stimulation of Splenocytes and ELISPOT Assay.

Spleen cells were harvested into 5 ml of RPMI (Sigma, UK) supplemented with 2 mM glutamine, 1× penicillin-streptomycin (from a 100× stock, Life Technologies, UK) and 10% FCS (Life Technologies, UK). Cells were strained using 70 μM cell strainer (BD biosciences) and pelleted by centrifugation 200 g for 5 minutes at 4° C. Erythrocytes were lysed using 1 ml of Red Cell Lysis Buffer (Sigma, UK) for 1 m at room temperature and neutralised with 14 ml of RPMI. Cells were washed with RPMI twice by centrifugation as described and resuspended in 2 ml of RPMI with supplements. 50 μl of each pool of previously prepared recombinant AhpC or MPA antigen diluted in RPMI and supplements were added to the wells of 96 well PVDF membrane filter plates (cat #S2EM04M99, Millipore, UK), which were previously coated with capture antibody. 50 μl of splenocytes adjusted to a concentration of $2.5 \times 10^7$ cells/ml were added to the wells containing antigen and incubated. Final concentration of antigens in each well was 2.5 μg/ml of recombinant protein. The following materials were obtained from BD Biosciences Pharmingen, UK. BD™ ELISPOT Horseradish peroxidase, BD™ AEC substrate set, and BD™ mouse gamma interferon cytokine ELISPOT pair consisting of a capture and detection antibody. The ELISPOT procedure followed was that described in BD Pharmingen Technical data sheet TDS Mar. 24, 2003. Spots were enumerated manually. Statistical analysis was performed using the Mann-Whitney (two tailed) test.

Results.

No adverse effects were seen in either control Group 1 mice or the experimental Group 2 mice during the course of the study or at autopsy. No significant difference was found in spleen weights between the two Groups. Mean ELISPOT responses (FIG. 3 A) by spleen cells to purified rec.AhpC antigen were 83.3 in sham vaccinated Group 1 and 903.8 in the test vaccinated Group 2 ($p<0.015$). Mean ELISPOT responses by spleen cells to purified rec.MPA antigen were 91.0 in sham vaccinated Group 1 and 900.7 in the test vaccinated Group 2 ($p<0.004$) (FIG. 3 A). Highly significant ELISPOT responses were also seen with peptide groups B and F compared with vector-only controls (FIG. 3 A). In a further experiment (FIG. 3 B) ELISPOT responses were determined for the individual peptides within pool F. The entire response is seen to be due to prominent recognition of peptide 9.1. This has the sequence GFAEINPIA (FIG. 4) and comprises a strong T cell epitope corresponding to the 5th extracellular loop in mpa (FIG. 5A) and within Havilah Seq ID. No 24 residues 761-769 and FIG. 1.

Conclusion.

Prime boost vaccination of female C57/BL6 mice using plasmid and MVA vectors expressing Havilah are highly immunogenic resulting in significant populations of antigen specific spleen cells against both AhpC at the amino terminus, and MPA at the carboxy terminus and with synthetic peptide epitopes of the Havilah polyprotein. The high level of antigen specific immunity to Havilah polyprotein and peptide epitopes following vaccination as described is not associated with any adverse effect.

3. Safety and Efficacy of Therapeutic and Protective Vaccination Against a Slow Growing Laboratory Strain of MAP Using pSG2.HAV then MVA.HAV A first study was carried out to test the Havilah vaccine as a treatment for pre-existing *Mycobacterium avium* subspecies *paratuberculosis* (MAP) infection as occurs in Johne's disease in animals and Crohn's disease and Irritable Bowel Syndrome in humans. Four groups of 8 naïve 4-6 week old C57/BL6 female mice were isolator maintained. Their physical condition was monitored daily and body weights recorded twice weekly and at the end of the study. After an initial settle-in period of 7 days all 32 mice were infected with $4\times10^7$ of a slow growing attenuated laboratory strain of bovine MAP i.p. in 200 μl sterile saline. Four weeks later control Group 1 mice were given 25 μg of pSG2 expression plasmid in 50 μl sterile endotoxin free TE buffer i.m. into each thigh. Experimental group 2 mice were prime vaccinated with 25 μg of rec.pSG2.Hav in 50 μl sterile endotoxin free TE buffer i.m. into each thigh. Control Group 3 mice received 50 μl of sterile endotoxin free TE buffer i.m. into each thigh. This priming procedure was repeated after 1 week. Nine days later control Group 1 mice were given $5\times10^6$ pfu Modified Vaccinia Ankara.GFP (MVA) vector alone i.v. into the tail vein in 100 μl sterile endotoxin free TE buffer. Experimental Group 2 mice were boost vaccinated with the same dose i.v. of recombinant MVA.Hav expressing the Havilah construct. Control Group 3 mice were given 100 μl sterile endotoxin free TE buffer i.v. into the tail vein. Pairs of naïve mice from Group 4 were autopsied at intervals throughout the study to monitor the progress of the MAP infection. The study was terminated 26 weeks after the original MAP infection. The infective load of MAP organisms was measured in the spleens and livers of all the mice using a sensitive and specific quantitative real-time IS900 PCR.

A second study was carried out to test the ability of the Havilah vaccine to confer some protection against subsequent MAP infection. Three groups of 8 naïve 4-6 week old C57/BL6 female mice were isolator maintained. Their physical condition was monitored daily and body weights recorded twice weekly and at the end of the study. After an initial settle-in period of 7 days control Group 1 mice were given 25 μg of pSG2 expression plasmid in 50 μl sterile endotoxin free TE buffer i.m. into each thigh. Experimental group 2 mice were prime vaccinated with 25 μg of rec.pSG2.Hav in 50 μl sterile endotoxin free TE buffer i.m. into each thigh. Control Group 3 mice received 50 μl of sterile endotoxin free TE buffer i.m. into each thigh. This priming procedure was repeated after 1 week. Ten days later control Group 1 mice were given $5\times10^6$ pfu Modified Vaccinia Ankara.GFP (MVA) vector alone i.v. into the tail vein in 100 μl sterile endotoxin free TE buffer. Experimental Group 2 mice were boost vaccinated with the same dose i.v. of recombinant MVA.Hav expressing the Havilah construct. Control Group 3 mice were given 100 μl sterile endotoxin free TE buffer i.v. into the tail vein. Eight days later all mice were infected with $4\times10^7$ MAP bovine strain K10 i.p. in 200 μl sterile saline. The study was terminated 24½ weeks later and the infective load of MAP organisms was measured in the spleens and livers of all the mice using quantitative real-time IS900 PCR as before.

Results.

No adverse effects of the vaccine were seen in any of the Havilah vaccinated or control mice throughout the study or at autopsy. In the therapeutic vaccination study the numbers of MAP organisms in the spleens of the mice in control Groups 1 and 3 were generally in the range 10 to 10,000 per gram of tissue. In the vaccine treated Group 2 no MAP organisms could be detected at all in the spleens of 6 of the 8 mice (FIG. 5B). In the other 2 animals in this group the number of MAP was around the lower limit of detection of the qRT-PCR in the range 1-10 per gram of tissue $p=0.003$ for Group 2 versus controls. The infective load of MAP in the liver of Havilah vaccine treated mice in Group 2 was also significantly reduced $p=0.019$. In the study of protective vaccination the efficacy of the vaccine was not as dramatic as therapeutic vaccination but the infective load of MAP in the liver was significantly lower than control mice $p=0.0074$.

Conclusions.

Therapeutic vaccination against MAP using plasmid and MVA vectors expressing the Havilah construct results in a highly significant attenuation of the MAP infection. Vaccination using these vectors expressing the Havilah construct has a smaller but significant protective effect against subsequent MAP infection. The pre-existence of MAP infection appears to confer advantage by priming the response to the vaccine used in its therapeutic role. Vaccination in the presence of MAP infection using vectors containing Havilah is safe and is not associated with any adverse effect.

4. Safety and Immunogenicity of Vaccination Using Ad5.HAV then MVA.HAV

A further study was carried out in 3 groups of six naïve 4-6 week old female C57/BL6 mice following the format previously described. Group 1 received 108 pfu of Ad5 vector in 50 μl buffer intradermally (i.d) into the pinna of the ear; group 2 received the same dose of Ad5.HAV i.d and group 3 received 50 μl buffered saline only. Two weeks later the groups 1-3 were vaccinated with $10^8$ pfu MVA vector only, $10^8$ pfu MVA.HAV or buffer i.d respectively. The animals were killed at 4 weeks noting clinical and autopsy conditions and body weights. Spleen cells and serum were obtained to quantify immunological responses to vaccine antigens.

Results.

No adverse effects due to the vaccination were seen in any of the animals. Significant recognition of rec.AhpC, rec.gsd and rec.mpa in ELISPOT assays as well as of pooled peptide antigens especially peptide 9.1 GFAEINPIA and pool J compared with controls, again occurred. There was also significant recognition of the recombinant antigens AhpC and mpa by antibody in the vaccinated group compared with control groups.

To test the reproducibility of these findings the study was repeated using 3 similar groups of eight mice and a dose of $2\times10^7$ pfu of either viral vector alone or $2\times10^7$ pfu Ad5.HAV followed by $2\times10^7$ pfu MVA.HAV i.d in 50 μl into the pinna of the ear. The animals were killed after 4 weeks.

Figure 6:
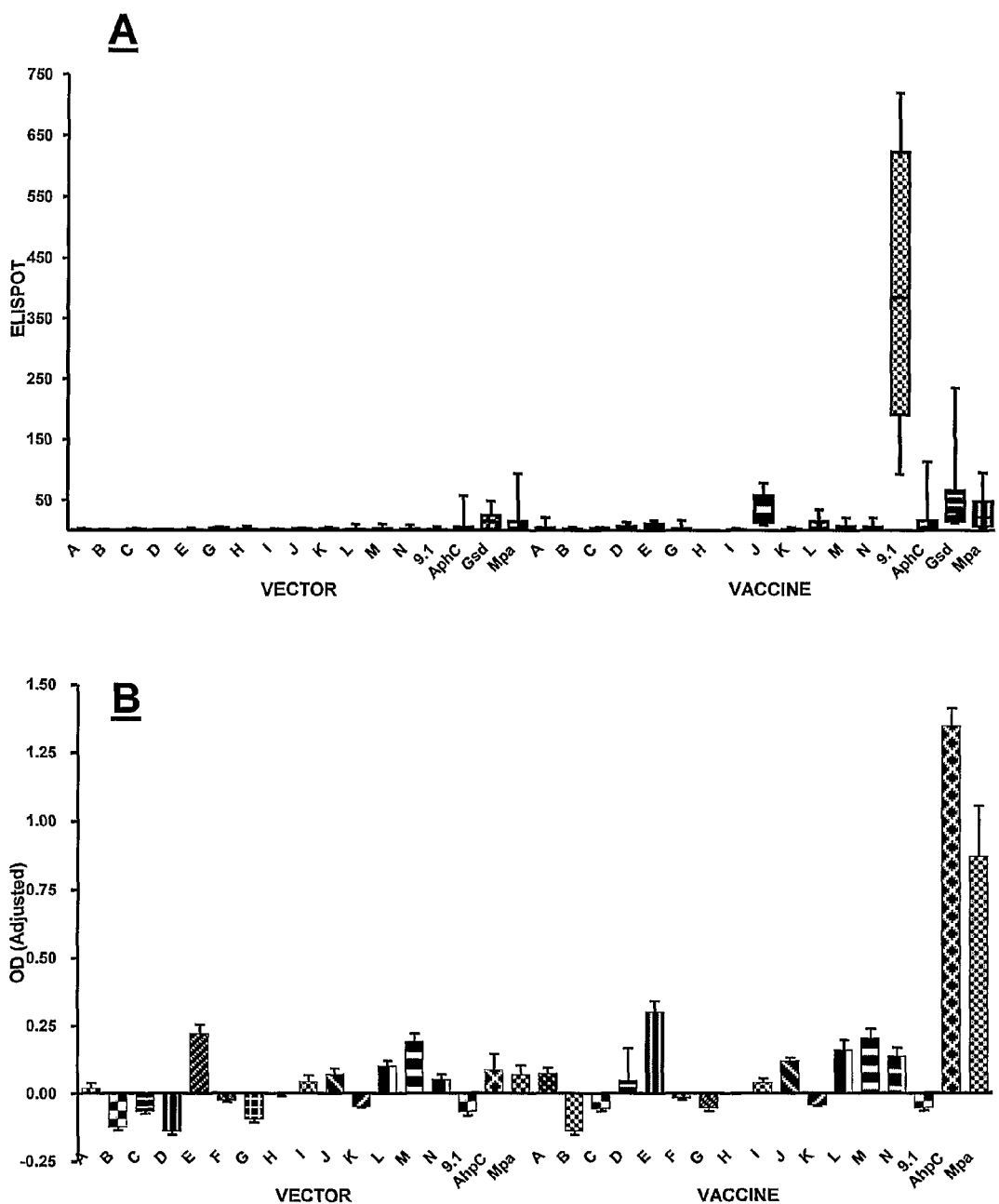
FIG. 6. Highly significant antigen-specific T cell (A. ELISPOT) and antibody (B. ELISA) responses to vaccination using Ad5.HAV to prime followed by MVA.HAV to boost in C57/BL6 mice. Prominent T cell recognition of the strong epitope in peptide 9.1 is again seen together with significant recognition of rec.Gsd and rec.Mpa proteins and peptide pools J and L, compared with animals vaccinated using vectors alone. By contrast none of the peptides including 9.1 are recognised by antibody in ELISA assays in response to vaccination but there is substantial recognition of rec.AhpC and rec.Mpa.

There was no evidence of adverse effects in any of these animals. Immune responses shown in FIGS. 6 A and B were the same as seen previously. There was again strong ELISPOT recognition of peptide 9.1 and significant responses to recombinant antigens and peptide pool J compared with vector only controls. By contrast there was no recognition of peptide 9.1 or any of the peptide pools by antibody and substantial antibody recognition of recombinant antigens AhpC and mpa.

Conclusions.

Vaccination of uninfected female C57/BL6 mice using Ad5.HAV followed by MVA.HAV expressing Havilah is highly immunogenic resulting in significant populations of antigen specific spleen cells recognizing both recombinant antigens and synthetic peptide epitope pools. Of particular note is the repeated demonstration of the strong specific T cell epitope GFAEINPIA comprising the 5$^{th}$ extracellular loop of mpa recognized in vaccinated mice. Antigen specific immunity to Havilah polyprotein following vaccination is reproducibly not associated with any adverse effect.

5. Safety and Efficacy of Therapeutic and Protective Vaccination Against a Virulent Recent Disease Isolate of MAP Using Ad5.HAV then MVA.HAV Two further studies were carried out each using 2 or 3 groups of eight 4-6 week old female C57/BL6 mice to determine the safety and efficacy of vaccination against a fast growing virulent recent disease isolate of bovine MAP using $2 \times 10^7$ pfu Ad5.HAV then $2 \times 10^7$ pfu MVA.HAV compared with control groups receiving vector-only or buffered saline alone, following the format previously described. In a high dose study the animals received $10^7$ MAP i.p and in a low dose study $10^5$ MAP i.p. The study was terminated after 8 weeks of MAP infection and the infective load of MAP organisms was measured in the spleens and livers of all the mice using a sensitive and specific quantitative real-time IS900 PCR.

Results.

Figure 7:
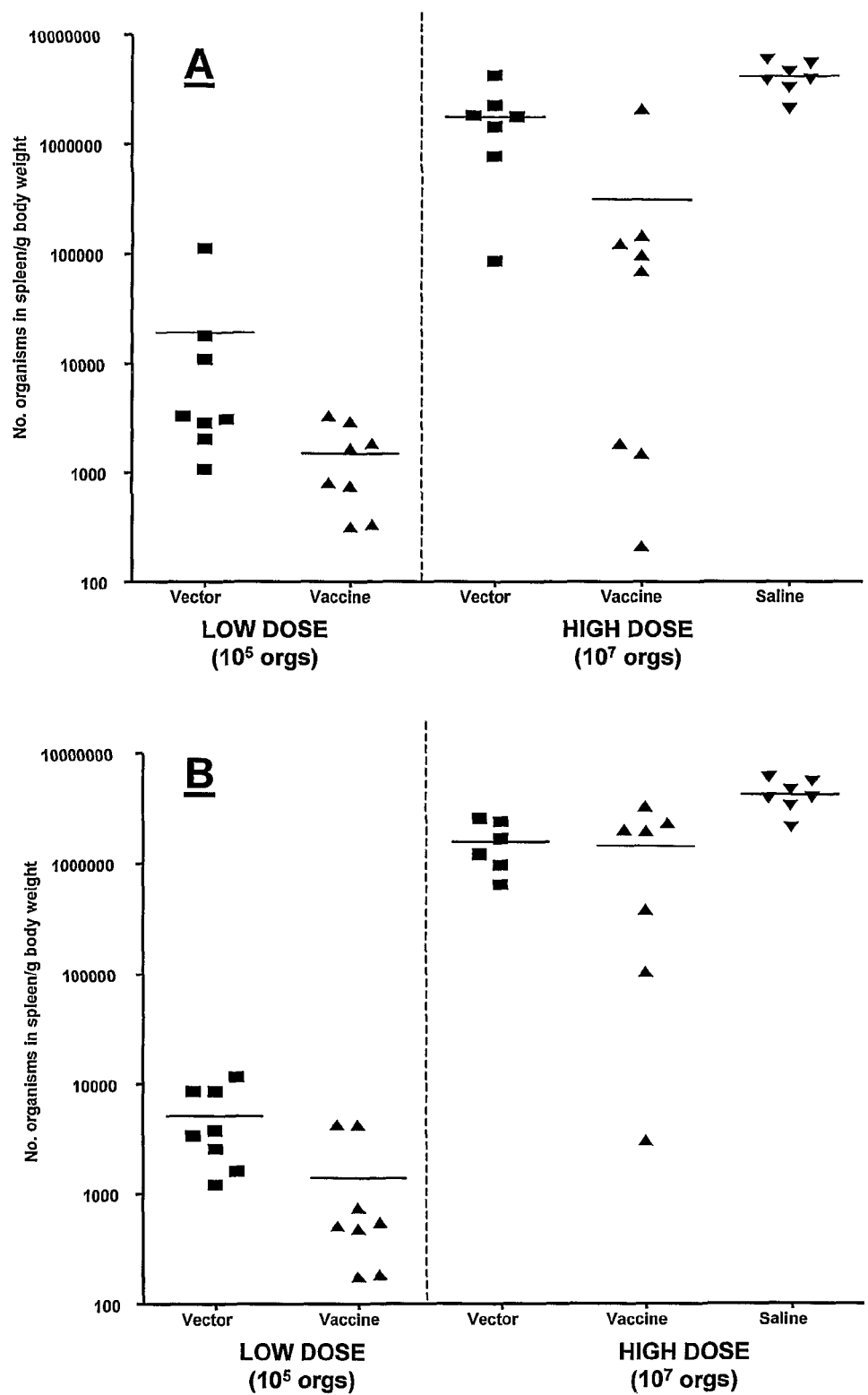
FIG. 7. Highly significant reduction compared to vector-only controls, in the infective load of MAP organisms in the spleen tissue of C57/BL6 mice challenged i.p with low dose or high dose MAP in response to vaccination using Ad5.HAV followed by MVA.HAV given either before (prophylactic) or after (therapeutic) the MAP challenge. A=prophylactic treatment (E1+G1). Low dose vector vs vaccine: p=0.0207; high dose vector vs vaccine: p=0.0205. B=therapeutic treatment (E2+G2). Low dose vector vs vaccine: p=0.0207; high dose vector vs vaccine: p=0.0023.
Figure 8:
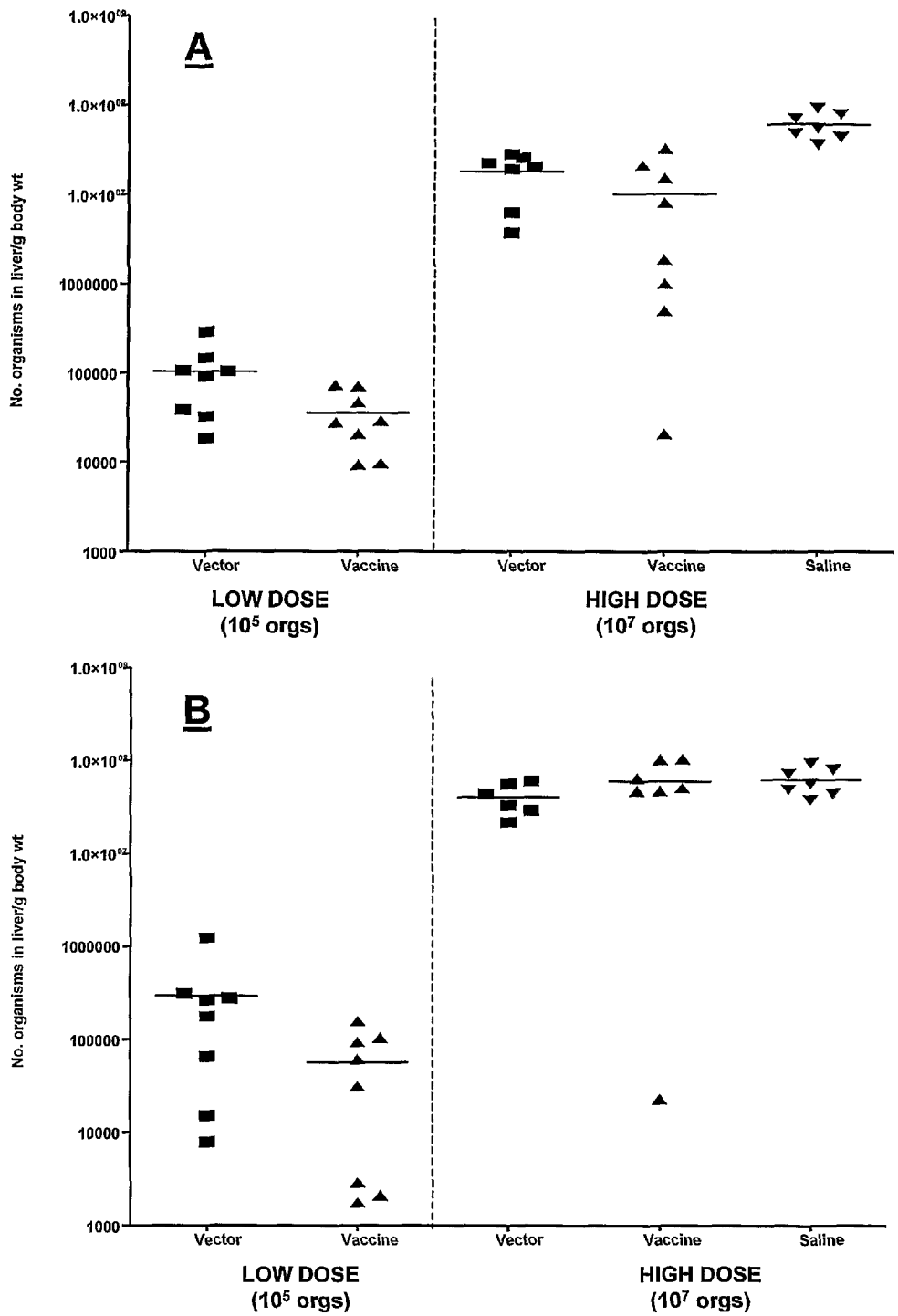
FIG. 8. The same experiment as in FIG. 7 also showing significant reductions in the MAP infective load in the liver tissues of mice vaccinated with Ad5.HAV followed by MVA-.HAV as described above. A=prophylactic treatment (E1+G1). Low dose vector vs vaccine: p=0.0379; high dose vector vs vaccine: p=0.0003. B=therapeutic treatment (E2+G2). Low dose vector vs vaccine: p~0.0499.
Figure 9:
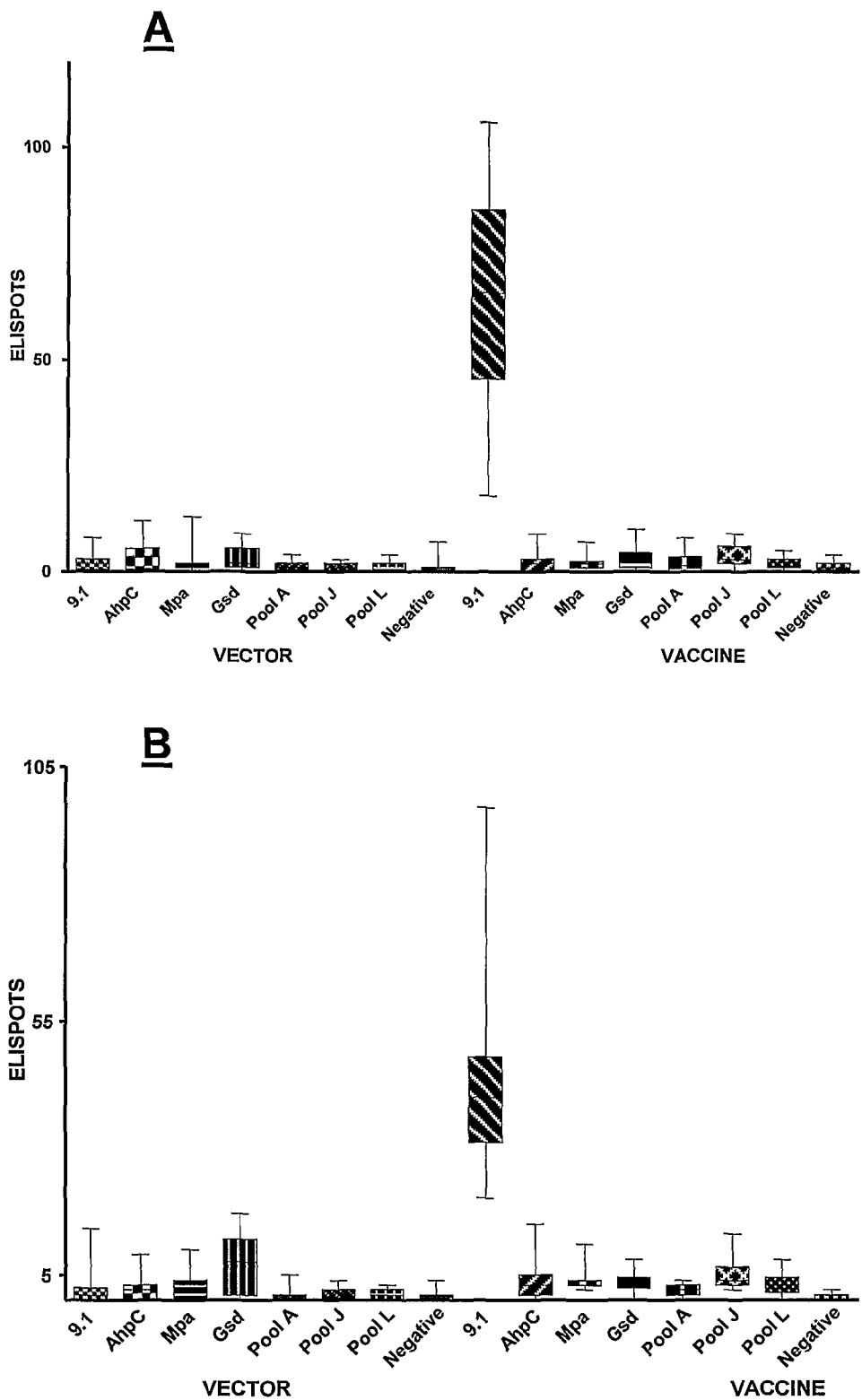
FIG. 9. Prominent recognition of the strong T cell epitope GFAEINPIA in mpa (peptide 9.1) and significant recognition of peptide pool J compared to vector-only controls, in the presence of MAP infection in C57/BL6 mice, in response to vaccination administered prophylactically (A) or therapeutically (B) as described for FIG. 7 above. In the presence of established MAP infection (therapeutic panel B) there is also significant recognition of peptide pool L compared to vector-only controls such that pre-existing MAP infection was capable of priming the response to vaccination. A=Pool J (p=0.0006); peptide 9.1 (p=<0.0001). B=Pool J (p=<0.0001); Pool L (p=0.0032); Peptide 9.1 (p=<0.0001).

None of the animals demonstrated any adverse effects of vaccination. The numbers of MAP organisms in the spleen tissues of the mice vaccinated therapeutically or prophylactically was significantly reduced compared to control groups both in the low dose and high dose studies (FIG. 7). With the exception of the high dose study the numbers of MAP organisms in the liver tissues of the mice vaccinated therapeutically or prophylactically was also significantly reduced compared to control groups (FIG. 8). FIG. 9 shows that the strong T cell epitope GFAEINPIA in peptide 9.1 is again prominently recognised despite the presence of virulent MAP infection. Peptide pool J is significantly recognised in both prophylactic and therapeutic vaccination. Peptide pool L is again significantly recognised when vaccination is given to animals which are already MAP infected consistent with the prior infection 'priming' the response to the vaccine used therapeutically.

Conclusions.

Vaccination using Havilah expressed in plasmid, Adenovirus and MVA pox virus vectors given by different immunisation routes in different doses demonstrates a reproducible and highly significant antigen-specific T cell immunogenicity in mice without adverse effect. Vaccination induced significant T cell recognition both of recombinant Havilah proteins and of synthetic peptide epitopes within the Havilah sequence, especially the strong T cell epitope GRAEINPIA corresponding to the 5$^{th}$ extracellular loop of the mpa moiety. Significant antibody responses to recombinant AhpC and mpa also occurred. Using different vector combinations in different doses and different routes of administration against different strains of MAP, vaccination using Havilah constructs repeatedly results in significant therapeutic attenuation of pre-existing MAP infection and protection against subsequent MAP infection. Furthermore, responses to therapeutic vaccination may be enhanced by the 'priming' effect of pre-existing MAP infection. Havilah may be used as a vaccine to confer protection against MAP infections and to treat MAP infections of animals and humans such as Johne's disease and Crohn's disease and Irritable Bowel syndrome as well as to potentiate the clinical response to treatment with anti-MAP drugs.

The invention claimed is:

1. A polynucleotide which encodes a polypeptide comprising an ahpC polypeptide sequence, a gsd polypeptide sequence, a p12 polypeptide sequence and an mpa polypeptide sequence, wherein
said ahpC polypeptide comprises:
(ai) the sequence of SEQ ID NO: 2,
(aii) a variant of SEQ ID NO: 2 having more than 70% amino acid
sequence identity to SEQ ID NO: 2 across the full length of SEQ ID NO: 2 which comprises at least one amino acid sequence selected from the group consisting of amino acids 48 to 56 of SEQ ID NO: 4, amino acids 90 to 101 of SEQ ID NO: 4 and amino acids 161 to 169 of SEQ ID NO: 4; or
(aiii) a fragment of SEQ ID NO: 2 which comprises at least one amino acid sequence selected from the group consisting of amino acids 48 to 56 of SEQ ID NO: 4, amino acids 90 to 101 of SEQ ID NO: 4 and amino acids 161 to 169 of SEQ ID NO: 4;
said gsd polypeptide comprises:
(bi) the sequence of SEQ ID NO: 6,
(bii) a variant of SEQ ID NO: 6 having more than 70% amino acid sequence identity to SEQ ID NO: 6 across the full length of SEQ ID NO: 6 which comprises at least one amino acid sequence selected from the group consisting of amino acids 1 to 32 of SEQ ID NO: 8, amino acids 58 to 68 of SEQ ID NO: 8, amino acids 99 to 119 of SEQ ID NO: 8, amino acids 123 to 147 of SEQ ID NO: 8, amino acids 159 to 169 of SEQ ID NO: 8, amino acids 180 to 194 of SEQ ID NO: 8, amino acids 200 to 231 of SEQ ID NO: 8, amino acids 64 to 76 of SEQ ID NO: 8, amino acids 95 to 110 of SEQ ID NO: 8, amino acids 192 to 206 of SEQ ID NO: 8 and amino acids 223 to 240 of SEQ ID NO: 8; or
(biii) a fragment of SEQ ID NO: 6 which comprises at least one amino acid sequence selected from the group consisting of amino acids 1 to 32 of SEQ ID NO: 8, amino acids 58 to 68 of SEQ ID NO: 8, amino acids 99 to 119 of SEQ ID NO: 8, amino acids 123 to 147 of SEQ ID NO: 8, amino acids 159 to 169 of SEQ ID NO: 8, amino acids 180 to 194 of SEQ ID NO: 8, amino acids 200 to 231 of SEQ ID NO: 8, amino acids 64 to 76 of SEQ ID NO: 8, amino acids 95 to 110 of SEQ ID NO: 8, amino acids 192 to 206 of SEQ ID NO: 8 and amino acids 223 to 240 of SEQ ID NO: 8;
said p12 polypeptide comprises:
(ci) the sequence of SEQ ID NO: 10,
(cii) a variant of SEQ ID NO: 10 having more than 70% amino acid sequence identity to SEQ ID NO: 10 across the full length of SEQ ID NO: 10 which comprises at least one amino acid sequence selected from the group consisting of amino acids 33 to 56 of SEQ ID NO: 12, amino acids 98 to 117 of SEQ ID NO: 12 and amino acids 3 to 10 of SEQ ID NO: 12; or
(ciii) a fragment of SEQ ID NO: 10 which comprises at least one amino acid sequence selected from the group consisting of amino acids 33 to 56 of SEQ ID NO: 12, amino acids 98 to 117 of SEQ ID NO: 12 and amino acids 3 to 10 of SEQ ID NO: 12; and said mpa polypeptide comprises:
(di) the sequence of SEQ ID NO: 14,
(dii) a variant of SEQ ID NO: 14 having more than 70% amino acid sequence identity to SEQ ID NO: 14 across the full length of SEQ ID NO: 14 which comprises at least one amino acid sequence selected from the group consisting of amino acids 130 to 160 of SEQ ID NO: 16, amino acids 56 to 64 of SEQ ID NO: 16, amino acids 150 to 160 of SEQ ID NO: 16 and amino acids 177 to 185 of SEQ ID NO: 16; or
(diii) a fragment of SEQ ID NO: 14 which comprises at least one amino acid sequence selected from the group consisting of amino acids 130 to 160 of SEQ ID NO: 16, amino acids 56 to 64 of SEQ ID NO: 16, amino acids 150 to 160 of SEQ ID NO: 16 and amino acids 177 to 185 of SEQ ID NO: 16.

2. A polynucleotide according to claim 1 wherein said ahpC polypeptide has the amino acid sequence given in SEQ ID NO: 4.

3. A polynucleotide according to claim 1 wherein said gsd polypeptide has the amino acid sequence given in SEQ ID NO: 8.

4. A polynucleotide according to claim 1 wherein said p12 polypeptide has the amino acid sequence given in SEQ ID NO: 12.

5. A polynucleotide according to claim 1 wherein said mpa polypeptide has the amino acid sequence given in SEQ ID NO: 16.

6. A polynucleotide according to claim 1 wherein said mpa polypeptide comprises the amino acid sequence GFAEINPIA.

7. A polynucleotide according to claim 1 wherein said encoded polypeptide comprises the amino acid sequences of SEQ ID Nos: 4, 8, 12 and 16.

8. A polynucleotide according to claim 1 wherein said encoded polypeptide comprises the amino acid sequence given in SEQ ID NO: 24.

9. A polynucleotide according to claim 1 which comprises:
(a) the ahpC polynucleotide of SEQ ID NO: 1 or a variant thereof having at least 70% homology to SEQ ID NO: 1 across the full length of SEQ ID NO: 1 or a fragment of SEQ ID NO: 1 which encodes at least one amino acid sequence selected from the group consisting of amino acids 48 to 56 of SEQ ID NO: 4, amino acids 90 to 101 of SEQ ID NO: 4 and amino acids 161 to 169 of SEQ ID NO: 4;
(b) the gsd polynucleotide of SEQ ID NO: 5 or a variant thereof having at least 70% homology to SEQ ID NO: 5 across the full length of SEQ ID NO: 5 or a fragment of SEQ ID NO: 5 which encodes at least one amino acid sequence selected from the group consisting of amino acids 1 to 32 of SEQ ID NO: 8, amino acids 58 to 68 of SEQ ID NO: 8, amino acids 99 to 119 of SEQ ID NO: 8, amino acids 123 to 147 of SEQ ID NO: 8, amino acids 159 to 169 of SEQ ID NO: 8, amino acids 180 to 194 of SEQ ID NO: 8, amino acids 200 to 231 of SEQ ID NO: 8, amino acids 64 to 76 of SEQ ID NO: 8, amino acids 95 to 110 of SEQ ID NO: 8, amino acids 192 to 206 of SEQ ID NO: 8 and amino acids 223 to 240 of SEQ ID NO: 8;
(c) the p12 polynucleotide of SEQ ID NO: 9 or a variant thereof having at least 70% homology to SEQ ID NO: 9 across the full length of SEQ ID NO: 9 or a fragment of SEQ ID NO: 9 which encodes at least one amino acid sequence selected from the group consisting of amino acids 33 to 56 of SEQ ID NO: 12, amino acids 98 to 117 of SEQ ID NO: 12 and amino acids 3 to 10 of SEQ ID NO: 12; and
(d) the mpa polynucleotide of SEQ ID NO: 13 or a variant thereof having at least 70% homology to SEQ ID NO: 13 across the full length of SEQ ID NO: 13 or a fragment of SEQ ID NO: 13 which encodes an epitope which encodes at least one amino acid sequence selected from the group consisting of amino acids 130 to 160 of SEQ ID NO: 16, amino acids 56 to 64 of SEQ ID NO: 16, amino acids 150 to 160 of SEQ ID NO: 16 and amino acids 177 to 185 of SEQ ID NO: 16.

10. A polynucleotide according to claim 9 wherein said ahpC polynucleotide has the sequence given in SEQ ID NO: 3.

11. A polynucleotide according to claim 9 wherein said gsd polynucleotide has the sequence given in SEQ ID NO: 7.

12. A polynucleotide according to claim 9 wherein said p12 polynucleotide has the sequence given in SEQ ID NO: 11.

13. A polynucleotide according to claim 9 wherein said mpa polynucleotide has the sequence given in SEQ ID NO: 15.

14. A polynucleotide according to claim 9 which comprises the nucleic acid sequences of SEQ ID Nos: 3, 7, 11 and 15.

15. A polynucleotide according to claim 9 which comprises the nucleic acid sequence given in SEQ ID NO: 23.

16. A vector comprising a polynucleotide according to claim 1.

17. A vector capable of expressing an ahpC polypeptide, a gsd polypeptide, a p12 polypeptide and an mpa polypeptide as defined in claim 1.

18. A vector according to claim 16 which is a poxvirus vector, an adenovirus vector or a plasmid.

19. A host cell comprising a vector according to claim 16.

20. A host cell which is capable of expressing a polypeptide as defined in claim 1.

21. A kit for use in treating or preventing *Mycobacterium avium* subspecies *paratuberculosis* (MAP) infection or a condition or symptom associated with MAP infection, said kit comprising (i) at least one polynucleotide according to claim 1 and (ii) at least one other therapeutic agent, for simultaneous, sequential or separate use.

22. A kit for use in treating or preventing a condition or symptom associated with *Mycobacterium avium* subspecies *paratuberculosis* (MAP) infection, said kit comprising (i) at least one polynucleotide according to claim 1 and (ii) at least one other therapeutic agent, for simultaneous, sequential or separate use.

* * * * *

SEQUENCE LISTING

<160> NUMBER OF SEQ ID NOS: 167

<210> SEQ ID NO 1
<211> LENGTH: 606
<212> TYPE: DNA
<213> ORGANISM: Mycobacterium avium subsp. paratuberculosis

<400> SEQUENCE: 1

```
atgcctctgc tgaccatcgg cgatcagttc cccgcctacg agcttgaccg cgtgatcgcg      60
ggcgacctgt ccaaggtcga cgccaagcag cccggtgact acttcaccac cgtcaccagc     120
gaggaccacg ccggcaagtg gcgcgtggtg ttcttctggc ccaaggactt caccttcgtc     180
tgccccaccg agatcgccac cttcggcaag ctcaacgacg agttcgagga ccgcgacgcc     240
caggtgctcg gcgtctcgat cgacagcgag ttcgtccact tcaactggcg cgcccagcac     300
gaggacctga agaacctgcc gttcccgatg ctctcggaca tcaagcgcga actgagcctg     360
gccaccggtg ttctcaacgc cgacggcgtg gccgaccggg ccaccttcat cgtcgacccg     420
aacaacgaga tccagttcgt ctcggtcacc gcgggttcgg tgggccgcaa cgtcgaggaa     480
```

-continued

```
gtgctgcggg tgctggatgc gctgcagtcc gacgagctgt gcgcgtgcaa ctggcgcaag    540
ggtgacccga cgctgaacgc caccgaactg ctcaaggcct tgcttaaaa gggcgaattc     600 gtttaa                                                                606
```

<210> SEQ ID NO 2
<211> LENGTH: 195
<212> TYPE: PRT
<213> ORGANISM: Mycobacterium avium subsp. paratuberculosis

<400> SEQUENCE: 2

```
Met Pro Leu Leu Thr Ile Gly Asp Gln Phe Pro Ala Tyr Glu Leu Asp
1               5                   10                  15

Arg Val Ile Ala Gly Asp Leu Ser Lys Val Asp Ala Lys Gln Pro Gly
            20                  25                  30

Asp Tyr Phe Thr Thr Val Thr Ser Glu Asp His Ala Gly Lys Trp Arg
        35                  40                  45

Val Val Phe Phe Trp Pro Lys Asp Phe Thr Phe Val Cys Pro Thr Glu
    50                  55                  60

Ile Ala Thr Phe Gly Lys Leu Asn Asp Glu Phe Glu Asp Arg Asp Ala
65                  70                  75                  80

Gln Val Leu Gly Val Ser Ile Asp Ser Glu Phe Val His Phe Asn Trp
                85                  90                  95

Arg Ala Gln His Glu Asp Leu Lys Asn Leu Pro Phe Pro Met Leu Ser
            100                 105                 110

Asp Ile Lys Arg Glu Leu Ser Leu Ala Thr Gly Val Leu Asn Ala Asp
        115                 120                 125

Gly Val Ala Asp Arg Ala Thr Phe Ile Val Asp Pro Asn Asn Glu Ile
    130                 135                 140

Gln Phe Val Ser Val Thr Ala Gly Ser Val Gly Arg Asn Val Glu Glu
145                 150                 155                 160

Val Leu Arg Val Leu Asp Ala Leu Gln Ser Asp Glu Leu Cys Ala Cys
                165                 170                 175

Asn Trp Arg Lys Gly Asp Pro Thr Leu Asn Ala Thr Glu Leu Leu Lys
            180                 185                 190

Ala Ser Ala
195
```

<210> SEQ ID NO 3
<211> LENGTH: 585
<212> TYPE: DNA
<213> ORGANISM: Artificial Sequence
<220> FEATURE:
<223> OTHER INFORMATION: Synthetic Construct

<400> SEQUENCE: 3

```
ccccttctca ctatcggaga ccagttcccc gcttacgaac ttacagctct tatcgctgga    60
gatctgagta aggttgacgc caaacagccc ggcgattatt tcactaccgt taccagtgag   120
gatcacgcag gtaaatggag agtcgtcttc ttctggccta agacttcac ctttgtgtgc    180 cctactgaga tcgcaacatt cgggaagctg aacgatgagt tcgaagatcg agacgcacag   240
gttttgggcg tgtctatcga ttccgagttc gtgcacttca ctggagagc acagcatgaa   300 gatctcaaga accttccatt ccccatgctc agcgacatca gagagaact gagcttggca   360 acaggtgttc tgaatgctga tggcgttgct gacagagcaa cattcattgt tgaccccaat   420
aacgagatcc agttcgtttc cgttactgct ggttctgtcg gtagaaacgt tgaagaggtc   480
```
ctgagagttc tcgacgcact tcagagtgat gaactgtgtg cctgcaattg gcggaaagga      540
gatcctactc tcaatgccac agagctgctt aaagcaagtg ctctc                      585

<210> SEQ ID NO 4
<211> LENGTH: 195
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (48)..(56)
<223> OTHER INFORMATION: strong class II human epitope
<220> FEATURE:
<221> NAME/KEY: MISC_FEATURE
<222> LOCATION: (90)..(101)
<223> OTHER INFORMATION: strong class II human epitope
<220> FEATURE:
<221> NAME/KEY: MISC_FEATURE
<222> LOCATION: (161)..(169)
<223> OTHER INFORMATION: strong class II human epitope

<400> SEQUENCE: 4

Pro Leu Leu Thr Ile Gly Asp Gln Phe Pro Ala Tyr Glu Leu Thr Ala
1               5                   10                  15

Leu Ile Ala Gly Asp Leu Ser Lys Val Asp Ala Lys Gln Pro Gly Asp
            20                  25                  30

Tyr Phe Thr Thr Val Thr Ser Glu Asp His Ala Gly Lys Trp Arg Val
        35                  40                  45

Val Phe Phe Trp Pro Lys Asp Phe Thr Phe Val Cys Pro Thr Glu Ile
    50                  55                  60

Ala Thr Phe Gly Lys Leu Asn Asp Glu Phe Glu Asp Arg Asp Ala Gln
65                  70                  75                  80

Val Leu Gly Val Ser Ile Asp Ser Glu Phe Val His Phe Asn Trp Arg
                85                  90                  95

Ala Gln His Glu Asp Leu Lys Asn Leu Pro Phe Pro Met Leu Ser Asp
            100                 105                 110

Ile Lys Arg Glu Leu Ser Leu Ala Thr Gly Val Leu Asn Ala Asp Gly
        115                 120                 125

Val Ala Asp Arg Ala Thr Phe Ile Val Asp Pro Asn Asn Glu Ile Gln
    130                 135                 140

Phe Val Ser Val Thr Ala Gly Ser Val Gly Arg Asn Val Glu Glu Val
145                 150                 155                 160

Leu Arg Val Leu Asp Ala Leu Gln Ser Asp Glu Leu Cys Ala Cys Asn
                165                 170                 175

Trp Arg Lys Gly Asp Pro Thr Leu Asn Ala Thr Glu Leu Leu Lys Ala
            180                 185                 190

Ser Ala Leu
        195

<210> SEQ ID NO 5
<211> LENGTH: 801
<212> TYPE: DNA
<213> ORGANISM: Mycobacterium avium subsp. paratuberculosis

<400> SEQUENCE: 5
atgactgcgc agtgttctc gataattatc cctaccttca atgcagcggt gacgctgcaa      60
gcctgcctcg gaagcatcgt cgggcagacc taccgggaag tggaagtggt ccttgtcgac    120
ggcggttcga ccgatcggac cctcgacatc gcgaacagtt tccgcccgga actcggctcg    180

```
cgactggtcg ttcacagcgg gcccgatgat ggcccctacg acgccatgaa ccgcggcgtc    240
ggcgtagcca caggcgaatg ggtactttt ttaggcgccg acgacaccct ctacgaacca    300
accacgttgg cccaggtagc cgcttttctc ggcgaccatg cggcaagcca tcttgtctat    360
ggcgatgttg tgatgcgttc gacgaaaagc cggcatgccg acctttcga cctcgaccgc    420 ctcctatttg agacgaattt gtgccaccaa tcgatctttt accgccgtga gcttttcgac    480
ggcatcggcc ttacaacct gcgctaccga gtctgggcgg actgggactt caatattcgc    540
tgcttctcca acccggcgct gattacccgc tacatggacg tcgtgatttc gaatacaac    600 gacatgaccg gcttcagcat gaggcagggg actgataaag agttcagaaa acggctgcca    660
atgtacttct gggttgcagg gtgggagact tgcaggcgca tgctggcgtt tttgaaagac    720
aaggagaatc gccgtctggc cttgcgtacg cggttgataa gggttaaggc cgtctccaaa    780
gaacgaagcg cagaaccgta g                                              801
```

<210> SEQ ID NO 6
<211> LENGTH: 266
<212> TYPE: PRT
<213> ORGANISM: Mycobacterium avium subsp. paratuberculosis

<400> SEQUENCE: 6

```
Met Thr Ala Pro Val Phe Ser Ile Ile Pro Thr Phe Asn Ala Ala
1               5                   10                  15

Val Thr Leu Gln Ala Cys Leu Gly Ser Ile Val Gly Gln Thr Tyr Arg
                20                  25                  30

Glu Val Glu Val Val Leu Val Asp Gly Gly Ser Thr Asp Arg Thr Leu
            35                  40                  45

Asp Ile Ala Asn Ser Phe Arg Pro Glu Leu Gly Ser Arg Leu Val Val
        50                  55                  60

His Ser Gly Pro Asp Asp Gly Pro Tyr Asp Ala Met Asn Arg Gly Val
65                  70                  75                  80

Gly Val Ala Thr Gly Glu Trp Val Leu Phe Leu Gly Ala Asp Asp Thr
                85                  90                  95

Leu Tyr Glu Pro Thr Thr Leu Ala Gln Val Ala Ala Phe Leu Gly Asp
            100                 105                 110

His Ala Ala Ser His Leu Val Tyr Gly Asp Val Val Met Arg Ser Thr
        115                 120                 125

Lys Ser Arg His Ala Gly Pro Phe Asp Leu Asp Arg Leu Leu Phe Glu
130                 135                 140

Thr Asn Leu Cys His Gln Ser Ile Phe Tyr Arg Arg Glu Leu Phe Asp
145                 150                 155                 160

Gly Ile Gly Pro Tyr Asn Leu Arg Tyr Arg Val Trp Ala Asp Trp Asp
                165                 170                 175

Phe Asn Ile Arg Cys Phe Ser Asn Pro Ala Leu Ile Thr Arg Tyr Met
            180                 185                 190

Asp Val Val Ile Ser Glu Tyr Asn Asp Met Thr Gly Phe Ser Met Arg
        195                 200                 205

Gln Gly Thr Asp Lys Glu Phe Arg Lys Arg Leu Pro Met Tyr Phe Trp
210                 215                 220

Val Ala Gly Trp Glu Thr Cys Arg Arg Met Leu Ala Phe Leu Lys Asp
225                 230                 235                 240

Lys Glu Asn Arg Arg Leu Ala Leu Arg Thr Arg Leu Ile Arg Val Lys
                245                 250                 255

Ala Val Ser Lys Glu Arg Ser Ala Glu Pro
```

260               265

<210> SEQ ID NO 7
<211> LENGTH: 729
<212> TYPE: DNA
<213> ORGANISM: Artificial Sequence
<220> FEATURE:
<223> OTHER INFORMATION: Synthetic Construct

<400> SEQUENCE: 7
ggatccattg tcggacagac ctatagagag gtggaagttg tcctggtcga tggtggatct      60
acagatagga ctctcgacat tgccaactcc tttagaccag agctcggttc aaggctcgtt     120
gttcattctg gaccagatga tggaccatac gacgccatga acagaggtgt tggagttgct     180
acaggagaat gggtcttgtt ccttggagct gatgacactc tgtacgaacc gactacattg     240
gctcaggttg cagcattttt gggagatcat gcagcttctc accttgtgta cggagatgtg     300
gtcatgagat ccaccaagtc cagacatgct ggaccattcg atcttgacag actcctgttc     360
gagaccaacc tctgtcatca gagcatcttc tacagacggg aactcttcga cggaattgga     420
ccttacaacc tcaggtacag ggtttgggca gactgggatt caacatcag gtgcttctcg      480 aacccagctt tgatcacacg gtacatggat gttgtgatct ccgagtacaa cgatatgacc     540
ggcttctcca tgagacaggg aaccgacaaa gagttcagga agcgcttgcc aatgtacttc     600
tgggttgctg gatgggaaac atgtcggaga atgcttgctt tcctgaagga caaggagaac     660
aggagacttg ctctcaggac tagactcatc agggtcaaag cagtgtccaa ggaaaggagt     720
gctgaacct                                                            729

<210> SEQ ID NO 8
<211> LENGTH: 243
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(32)
<223> OTHER INFORMATION: Class I epitope
<220> FEATURE:
<221> NAME/KEY: MISC_FEATURE
<222> LOCATION: (58)..(68)
<223> OTHER INFORMATION: Class I epitope
<220> FEATURE:
<221> NAME/KEY: MISC_FEATURE
<222> LOCATION: (64)..(76)
<223> OTHER INFORMATION: Strong class II human epitope
<220> FEATURE:
<221> NAME/KEY: MISC_FEATURE
<222> LOCATION: (95)..(110)
<223> OTHER INFORMATION: Strong class II human epitope
<220> FEATURE:
<221> NAME/KEY: MISC_FEATURE
<222> LOCATION: (99)..(119)
<223> OTHER INFORMATION: Class I epitope
<220> FEATURE:
<221> NAME/KEY: MISC_FEATURE
<222> LOCATION: (123)..(147)
<223> OTHER INFORMATION: Class I epitope
<220> FEATURE:
<221> NAME/KEY: MISC_FEATURE
<222> LOCATION: (159)..(169)
<223> OTHER INFORMATION: Class I epitope
<220> FEATURE:
<221> NAME/KEY: MISC_FEATURE
<222> LOCATION: (180)..(194)
<223> OTHER INFORMATION: Class I epitope
<220> FEATURE:
<221> NAME/KEY: MISC_FEATURE
<222> LOCATION: (192)..(206)
<223> OTHER INFORMATION: Strong class II human epitope
<220> FEATURE:
<221> NAME/KEY: MISC_FEATURE
<222> LOCATION: (200)..(231)
<223> OTHER INFORMATION: Class I epitope
<220> FEATURE:
<221> NAME/KEY: MISC_FEATURE
<222> LOCATION: (223)..(240)
<223> OTHER INFORMATION: Strong class II human epitope

<400> SEQUENCE: 8

Gly Ser Ile Val Gly Gln Thr Tyr Arg Glu Val Glu Val Val Leu Val
1               5                   10                  15

Asp Gly Gly Ser Thr Asp Arg Thr Leu Asp Ile Ala Asn Ser Phe Arg
            20                  25                  30

Pro Glu Leu Gly Ser Arg Leu Val His Ser Gly Pro Asp Asp Gly
        35                  40                  45

Pro Tyr Asp Ala Met Asn Arg Gly Val Gly Val Ala Thr Gly Glu Trp
    50                  55                  60

Val Leu Phe Leu Gly Ala Asp Asp Thr Leu Tyr Glu Pro Thr Thr Leu
65                  70                  75                  80

Ala Gln Val Ala Ala Phe Leu Gly Asp His Ala Ala Ser His Leu Val
                85                  90                  95

Tyr Gly Asp Val Val Met Arg Ser Thr Lys Ser Arg His Ala Gly Pro
            100                 105                 110

Phe Asp Leu Asp Arg Leu Leu Phe Glu Thr Asn Leu Cys His Gln Ser
        115                 120                 125

Ile Phe Tyr Arg Arg Glu Leu Phe Asp Gly Ile Gly Pro Tyr Asn Leu
    130                 135                 140

Arg Tyr Arg Val Trp Ala Asp Trp Asp Phe Asn Ile Arg Cys Phe Ser
145                 150                 155                 160

Asn Pro Ala Leu Ile Thr Arg Tyr Met Asp Val Val Ile Ser Glu Tyr
                165                 170                 175

Asn Asp Met Thr Gly Phe Ser Met Arg Gln Gly Thr Asp Lys Glu Phe
            180                 185                 190

Arg Lys Arg Leu Pro Met Tyr Phe Trp Val Ala Gly Trp Glu Thr Cys
        195                 200                 205

Arg Arg Met Leu Ala Phe Leu Lys Asp Lys Glu Asn Arg Arg Leu Ala
    210                 215                 220

Leu Arg Thr Arg Leu Ile Arg Val Lys Ala Val Ser Lys Glu Arg Ser
225                 230                 235                 240

Ala Glu Pro

<210> SEQ ID NO 9
<211> LENGTH: 417
<212> TYPE: DNA
<213> ORGANISM: Mycobacterium avium subsp. paratuberculosis

<400> SEQUENCE: 9
cgatttcgcc gccaccgcca cgccgaaatc atcctgagca tgcccggatt cggcgtcatc    60
ctgggcgctg agttcctcgc cgccaccggc ggggacatgg ccgcattcgc ctccgccgac   120
cgcctcgccg cgtcgccgg cctggcgccg gtaccacgag attccggccg catcagcgga   180
aacctcaaac gccccgacg ctacgaccgg cgcctgctgc gcgcctgcta cctgtcggcc   240
ttggtcagca tccgcaccga ccctcctcg cgcacctact acgaccgaaa acgcaccgaa   300
ggaaaacgcc acacccaagc cgtcctcgcc ctggcccgcc gccgcctcaa cgtcctgtgg   360

```
gccatgctgc gcgaccacgc tgtctaccac cccgcaacca ctaccgcggc ggcttga       417
```

```
<210> SEQ ID NO 10
<211> LENGTH: 138
<212> TYPE: PRT
<213> ORGANISM: Mycobacterium avium subsp. paratuberculosis

<400> SEQUENCE: 10
```

```
Arg Phe Arg Arg His Arg His Ala Glu Ile Ile Leu Ser Met Pro Gly
 1               5                  10                  15

Phe Gly Val Ile Leu Gly Ala Glu Phe Leu Ala Ala Thr Gly Gly Asp
            20                  25                  30

Met Ala Ala Phe Ala Ser Ala Asp Arg Leu Ala Gly Val Ala Gly Leu
        35                  40                  45

Ala Pro Val Pro Arg Asp Ser Gly Arg Ile Ser Gly Asn Leu Lys Arg
    50                  55                  60

Pro Arg Arg Tyr Asp Arg Arg Leu Leu Arg Ala Cys Tyr Leu Ser Ala
65                  70                  75                  80

Leu Val Ser Ile Arg Thr Asp Pro Ser Ser Arg Thr Tyr Tyr Asp Arg
                85                  90                  95

Lys Arg Thr Glu Gly Lys Arg His Thr Gln Ala Val Leu Ala Leu Ala
            100                 105                 110

Arg Arg Arg Leu Asn Val Leu Trp Ala Met Leu Arg Asp His Ala Val
        115                 120                 125

Tyr His Pro Ala Thr Thr Thr Ala Ala Ala
    130                 135
```

```
<210> SEQ ID NO 11
<211> LENGTH: 420
<212> TYPE: DNA
<213> ORGANISM: Artificial Sequence
<220> FEATURE:
<223> OTHER INFORMATION: Synthetic Construct

<400> SEQUENCE: 11
agaattcgga gacatagaca tgcagagatc atcctgagca tgcctggatt tggcgttatc       60
ctcggagctg aatttcttgc agcaacagga ggtgatatgg cagctttcgc atcagctgac      120
agattggctg gagttgcagg tttggctcca gttccaagag attcagggag aatcagcggt      180
aacctcaaga gacctagacg ctacgacaga agactgctta gagcctgcta tctgagtgct      240
ttggttagca ttagaaccga cccctctagt cgaacctact acgataggaa gcggactgaa      300
ggtaagagac atacccaggc agtgttggca cttgctagaa gacggcttaa tgttctgtgg      360
gctatgctga gagatcatgc cgtgtaccat cctgctacca aacagctgc tgctagactt       420
```

```
<210> SEQ ID NO 12
<211> LENGTH: 140
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(10)
<223> OTHER INFORMATION: Strong class II human epitope
<220> FEATURE:
<221> NAME/KEY: MISC_FEATURE
<222> LOCATION: (33)..(56)
<223> OTHER INFORMATION: Class I epitope
<220> FEATURE:
<221> NAME/KEY: MISC_FEATURE
```

-continued

<222> LOCATION: (98)..(117)
<223> OTHER INFORMATION: Class I epitope

<400> SEQUENCE: 12

Arg Ile Arg Arg His Arg His Ala Glu Ile Ile Leu Ser Met Pro Gly
1               5                   10                  15

Phe Gly Val Ile Leu Gly Ala Glu Phe Leu Ala Ala Thr Gly Gly Asp
            20                  25                  30

Met Ala Ala Phe Ala Ser Ala Asp Arg Leu Ala Gly Val Ala Gly Leu
        35                  40                  45

Ala Pro Val Pro Arg Asp Ser Gly Arg Ile Ser Gly Asn Leu Lys Arg
    50                  55                  60

Pro Arg Arg Tyr Asp Arg Arg Leu Leu Arg Ala Cys Tyr Leu Ser Ala
65                  70                  75                  80

Leu Val Ser Ile Arg Thr Asp Pro Ser Ser Arg Thr Tyr Tyr Asp Arg
                85                  90                  95

Lys Arg Thr Glu Gly Lys Arg His Thr Gln Ala Val Leu Ala Leu Ala
            100                 105                 110

Arg Arg Arg Leu Asn Val Leu Trp Ala Met Leu Arg Asp His Ala Val
        115                 120                 125

Tyr His Pro Ala Thr Thr Thr Ala Ala Ala Arg Leu
    130                 135                 140

<210> SEQ ID NO 13
<211> LENGTH: 1335
<212> TYPE: DNA
<213> ORGANISM: Mycobacterium avium subsp. paratuberculosis

<400> SEQUENCE: 13
gtgactgaag ccaatgagtg caactcggcg tcgcgaaagg tttcagtcgc ggttgagcaa      60
gacaccgcaa gactactgga gtgcgtgcac aagcgccccc agctcgcggc tgaaagcgga     120
tgcaaagggg ttcgaagctt gagcaacatg cgaaggggag aacggcctat gagcctggga     180
caggttttcg acccgcgcgc gaatgcactt aatgcgtggc gcttggtgtt ggcgagcggg     240
gtgatcctat ggcattcgtt tccgctcact ggacgtatgc cgtgggcgcc gttcgtccag     300
ttgcttggcc ttgatgcgt tgatggtttc tttgcggtct ccggctatct catcgtctcg     360
agctggcttc gcaacccgca tcccgcccaa tacttcaccg ctcgatgtct tcgtattctc     420
ccgggtctgt ggatctgtct catcttgacg gcgtttgtca tcgctccgat aggtgtgggc     480
gcccagggcg gttcggccgc gaaactactg atgtccggcg ctccgatcga gtatgtgcta     540
aaagacagtg cggttggat ggttaagttc gatatcggtg gcacacctcg cgatattcca     600
gttgcgggta tttggaacgg ttctctgtgg acattgggtt gggaggtgct ttgctatatc     660
ggcgtagcag tatttggtat gctcggactt cttagtcgcc gttggttcgt tccagggata     720
ttgatcctgg cgctgtcgtg gtcggtgttc ttgccggcat ggggcggaat acacgcgatc     780
gcctccaatg ctgcgcgatt cgctgtgatg ttttcggccg gagcgttgct gtatcaattc     840
cgtaacgtga ttccggctcg gtggtccttc gttgccgtcg gcctcattat cgttgtggtt     900
tcctctgccg tgctgccgga ctaccggttg gtggcggccc ttccgatggc gtacctaatc     960
atcgcttcgg gttcgctcat ccacaatcaa aggatgaggt ccgcaccga tctatcctat    1020
ggagtatata tttatgcgtt ccaattcag caagtgctgg tcctgtgtgg attcgccgag    1080
ataaatccaa tcgctttctg cgcgatttct gtcgcagcta ttttgccgct cgccgcgctc    1140
agttggttct tggtcgagaa acctgcgttg tcctggaaga gtcgtctccg gcggaaaaac    1200

-continued

```
agttcaattg cgctagccaa tatggaagat ggtggatcag tcggccgctc aaatgacatt      1260
cccggaaggc gggcccgctt tattggcgag aaagccgaag atcctcccgc gccgagccca      1320
agaccggctt tgtaa                                                        1335
```

<210> SEQ ID NO 14
<211> LENGTH: 444
<212> TYPE: PRT
<213> ORGANISM: Mycobacterium avium subsp. paratuberculosis

<400> SEQUENCE: 14

```
Val Thr Glu Ala Asn Glu Cys Asn Ser Ala Ser Arg Lys Val Ser Val
1               5                   10                  15

Ala Val Glu Gln Asp Thr Ala Arg Leu Leu Glu Cys Val His Lys Arg
            20                  25                  30

Pro Gln Leu Ala Ala Glu Ser Gly Cys Lys Gly Val Arg Ser Leu Ser
        35                  40                  45

Asn Met Arg Arg Gly Glu Arg Pro Met Ser Leu Gly Gln Val Phe Asp
    50                  55                  60

Pro Arg Ala Asn Ala Leu Asn Ala Trp Arg Leu Val Leu Ala Ser Gly
65                  70                  75                  80

Val Ile Leu Trp His Ser Phe Pro Leu Thr Gly Arg Met Pro Trp Ala
                85                  90                  95

Pro Phe Val Gln Leu Leu Gly Leu Gly Cys Val Asp Gly Phe Phe Ala
            100                 105                 110

Val Ser Gly Tyr Leu Ile Val Ser Ser Trp Leu Arg Asn Pro His Pro
        115                 120                 125

Ala Gln Tyr Phe Thr Ala Arg Cys Leu Arg Ile Leu Pro Gly Leu Trp
    130                 135                 140

Ile Cys Leu Ile Leu Thr Ala Phe Val Ile Ala Pro Ile Gly Val Gly
145                 150                 155                 160

Ala Gln Gly Gly Ser Ala Ala Lys Leu Leu Met Ser Gly Ala Pro Ile
                165                 170                 175

Glu Tyr Val Leu Lys Asp Ser Ala Val Trp Met Val Lys Phe Asp Ile
            180                 185                 190

Gly Gly Thr Pro Arg Asp Ile Pro Val Ala Gly Ile Trp Asn Gly Ser
        195                 200                 205

Leu Trp Thr Leu Gly Trp Glu Val Leu Cys Tyr Ile Gly Val Ala Val
    210                 215                 220

Phe Gly Met Leu Gly Leu Leu Ser Arg Arg Trp Phe Val Pro Gly Ile
225                 230                 235                 240

Leu Ile Leu Ala Leu Ser Trp Ser Val Phe Leu Pro Ala Trp Gly Gly
                245                 250                 255

Ile His Ala Ile Ala Ser Asn Ala Ala Arg Phe Ala Val Met Phe Ser
            260                 265                 270

Ala Gly Ala Leu Leu Tyr Gln Phe Arg Asn Val Ile Pro Ala Arg Trp
        275                 280                 285

Ser Phe Val Ala Val Gly Leu Ile Ile Val Val Ser Ser Ala Val
    290                 295                 300

Leu Pro Asp Tyr Arg Leu Val Ala Ala Leu Pro Met Ala Tyr Leu Ile
305                 310                 315                 320

Ile Ala Ser Gly Ser Leu Ile His Asn Gln Arg Met Arg Phe Arg Thr
                325                 330                 335

Asp Leu Ser Tyr Gly Val Tyr Ile Tyr Ala Phe Pro Ile Gln Gln Val
```

-continued

```
                     340                 345                 350
Leu Val Leu Cys Gly Phe Ala Glu Ile Asn Pro Ile Ala Phe Cys Ala
            355                 360                 365
Ile Ser Val Ala Ala Ile Leu Pro Leu Ala Ala Leu Ser Trp Phe Leu
    370                 375                 380
Val Glu Lys Pro Ala Leu Ser Trp Lys Ser Arg Leu Arg Arg Lys Asn
385                 390                 395                 400
Ser Ser Ile Ala Leu Ala Asn Met Glu Asp Gly Gly Ser Val Gly Arg
                405                 410                 415
Ser Asn Asp Ile Pro Gly Arg Arg Ala Arg Phe Ile Gly Glu Lys Ala
            420                 425                 430
Glu Asp Pro Pro Ala Pro Ser Pro Arg Pro Ala Leu
        435                 440
```

<210> SEQ ID NO 15
<211> LENGTH: 738
<212> TYPE: DNA
<213> ORGANISM: Artificial Sequence
<220> FEATURE:
<223> OTHER INFORMATION: Synthetic Construct

<400> SEQUENCE: 15

| | | | | | |
|---|---|---|---|---|---|
| aagcttcgca | gaggtgagag | acctatgagt | cttggccagg | tcttttgatcc | tagagctaat | 60 |
| gcactgcact | ctttccctct | tacaggacgc | atgccttggg | ctccatttat | cgttagttcc | 120 |
| tggctcagaa | accctcatcc | agctcagtac | ttcacagcca | gatgtctcag | aatccttcct | 180 |
| ggtctttgga | ttggagcaca | gggtggttcc | gcagctaagc | tgttgatgag | tggtgcacca | 240 |
| atcgaatacg | tcctgaaaga | ctcagcagtg | tggatgttca | agttcgacat | tggaggaaca | 300 |
| ccaagggata | ttcctgtcgc | tggtatctgg | aatggaagtt | tgtggacccc | agcatgggga | 360 |
| ggtattcatg | ctatcgcttc | caacgcttac | cagttccgaa | atgtgatccc | tgcaagatgg | 420 |
| tctgtgagtt | cagccgtgtt | gccaaactat | agacttgttg | ctgctctccc | catggcctac | 480 |
| cataatcagc | gaatgaggtt | tcggacagat | ctgtcctatg | tgtgtacgg | gttcgctgaa | 540 |
| atcaatccca | tcgctctggt | tgagaaacct | gccctgtctt | ggaaatccag | actgagacgg | 600 |
| aagaactctt | ccatcgctct | cgcaaacatg | gaagatggtg | gtagtgttgg | aaggagtaac | 660 |
| gacatccctg | ggaggagggc | tagatttatt | ggtgagaaag | ccgaagatcc | tcctgctcca | 720 |
| tctcctagac | ccgccttg | | | | | 738 |

<210> SEQ ID NO 16
<211> LENGTH: 246
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (56)..(64)
<223> OTHER INFORMATION: Strong class II human epitope
<220> FEATURE:
<221> NAME/KEY: MISC_FEATURE
<222> LOCATION: (130)..(160)
<223> OTHER INFORMATION: Class I epitope
<220> FEATURE:
<221> NAME/KEY: MISC_FEATURE
<222> LOCATION: (150)..(160)
<223> OTHER INFORMATION: Strong class II human epitope

<400> SEQUENCE: 16

Lys Leu Arg Arg Gly Glu Arg Pro Met Ser Leu Gly Gln Val Phe Asp

```
               1               5                  10                 15
Pro Arg Ala Asn Ala Leu His Ser Phe Pro Leu Thr Gly Arg Met Pro
                20                 25                 30

Trp Ala Pro Phe Ile Val Ser Ser Trp Leu Arg Asn Pro His Pro Ala
                35                 40                 45

Gln Tyr Phe Thr Ala Arg Cys Leu Arg Ile Leu Pro Gly Leu Trp Ile
                50                 55                 60

Gly Ala Gln Gly Gly Ser Ala Ala Lys Leu Leu Met Ser Gly Ala Pro
65                  70                 75                 80

Ile Glu Tyr Val Leu Lys Asp Ser Ala Val Trp Met Phe Lys Phe Asp
                85                 90                 95

Ile Gly Gly Thr Pro Arg Asp Ile Pro Val Ala Gly Ile Trp Asn Gly
                100                105                110

Ser Leu Trp Thr Pro Ala Trp Gly Gly Ile His Ala Ile Ala Ser Asn
                115                120                125

Ala Tyr Gln Phe Arg Asn Val Ile Pro Ala Arg Trp Ser Val Ser Ser
                130                135                140

Ala Val Leu Pro Asn Tyr Arg Leu Val Ala Ala Leu Pro Met Ala Tyr
145                 150                155                160

His Asn Gln Arg Met Arg Phe Arg Thr Asp Leu Ser Tyr Gly Val Tyr
                165                170                175

Gly Phe Ala Glu Ile Asn Pro Ile Ala Leu Val Glu Lys Pro Ala Leu
                180                185                190

Ser Trp Lys Ser Arg Leu Arg Arg Lys Asn Ser Ser Ile Ala Leu Ala
                195                200                205

Asn Met Glu Asp Gly Gly Ser Val Gly Arg Ser Asn Asp Ile Pro Gly
                210                215                220

Arg Arg Ala Arg Phe Ile Gly Glu Lys Ala Glu Asp Pro Pro Ala Pro
225                 230                235                240

Ser Pro Arg Pro Ala Leu
                245

<210> SEQ ID NO 17
<211> LENGTH: 21
<212> TYPE: DNA
<213> ORGANISM: Artificial Sequence
<220> FEATURE:
<223> OTHER INFORMATION: Synthetic Construct

<400> SEQUENCE: 17
atgcagatct tcgtcaaact g                                           21

<210> SEQ ID NO 18
<211> LENGTH: 30
<212> TYPE: DNA
<213> ORGANISM: Artificial Sequence
<220> FEATURE:
<223> OTHER INFORMATION: Synthetic Construct

<400> SEQUENCE: 18
gaggattcca aaccctcttc tcggtcttga                                  30

<210> SEQ ID NO 19
<211> LENGTH: 2472
<212> TYPE: DNA
<213> ORGANISM: Artificial Sequence
<220> FEATURE:
<223> OTHER INFORMATION: Synthetic Construct
```

<400> SEQUENCE: 19

```
cccottctca ctatcggaga ccagttcccc gcttacgaac ttacagctct tatcgctgga      60
gatctgagta aggttgacgc caaacagccc ggcgattatt tcactaccgt taccagtgag     120
gatcacgcag gtaaatggag agtcgtcttc ttctggccta aagacttcac ctttgtgtgc     180
cctactgaga tcgcaacatt cgggaagctg aacgatgagt tcgaagatcg agacgcacag     240
gttttgggcg tgtctatcga ttccgagttc gtgcacttca actggagagc acagcatgaa     300
gatctcaaga accttccatt ccccatgctc agcgacatca agagagaact gagcttggca     360
acaggtgttc tgaatgctga tggcgttgct gacagagcaa cattcattgt tgaccccaat     420
aacgagatcc agttcgtttc cgttactgct ggttctgtcg gtagaaacgt tgaagaggtc     480
ctgagagttc tcgacgcact tcagagtgat gaactgtgtg cctgcaattg gcggaaagga     540
gatcctactc tcaatgccac agagctgctt aaagcaagtg ctctcggatc cattgtcgga     600
cagacctata gagaggtgga agttgtcctg gtcgatggtg gatctacaga taggactctc     660
gacattgcca actcctttag accagagctc ggttcaaggc tcgttgttca ttctggacca     720
gatgatggac catacgacgc catgaacaga ggtgttggag ttgctacagg agaatgggtc     780
ttgttccttg gagctgatga cactctgtac gaaccgacta cattggctca ggttgcagca     840
ttttgggag atcatgcagc ttctcacctt gtgtacggag atgtggtcat gagatccacc     900
aagtccagac atgctggacc attcgatctt gacagactcc tgttcgagac caacctctgt     960
catcagagca tcttctacag acgggaactc ttcgacggaa ttggaccctta caacctcagg    1020
tacagggttt gggcagactg ggatttcaac atcaggtgct tctcgaaccc agcttttgatc    1080
acacggtaca tggatgttgt gatctccgag tacaacgata tgaccggctt ctccatgaga    1140
cagggaaccg acaaagagtt caggaagcgc ttgccaatgt acttctgggt tgctggatgg    1200
gaaacatgtc ggagaatgct tgctttcctg aaggacaagg agaacaggag acttgctctc    1260
aggactagac tcatcagggt caaagcagtg tccaaggaaa ggagtgctga acctagaatt    1320
cggagacata gacatgcaga gatcatcctg agcatgcctg gatttggcgt tatcctcgga    1380
gctgaatttc ttgcagcaac aggaggtgat atggcagctt tcgcatcagc tgacagattg    1440
gctggagttg caggttttggc tccagttcca agagattcag ggagaatcag cggtaacctc    1500
aagagaccta gacgctacga cagaagactg cttagagcct gctatctgag tgctttggtt    1560
agcattagaa ccgacccctc tagtcgaacc tactacgata ggaagcggac tgaaggtaag    1620
agacataccc aggcagtgtt ggcacttgct agaagacggc ttaatgttct gtgggctatg    1680
ctgagagatc atgccgtgta ccatcctgct accacaacag ctgctgctag acttaagctt    1740
cgcagaggtg agagacctat gagtcttggc caggtctttg atcctagagc taatgcactg    1800
cactctttcc ctcttacagg acgcatgcct tgggctccat ttatcgttag ttcctggctc    1860
agaaaccctc atccagctca gtacttcaca gccagatgtc tcagaatcct tcctggtctt    1920
tggattggag cacagggtgg ttccgcagct aagctgttga tgagtggtgc accaatcgaa    1980
tacgtcctga aagactcagc agtgtggatg ttcaagttcg acattggagg aacaccaagg    2040
gatattcctg tcgctggtat ctggaatgga agtttgtgga ccccagcatg ggaggtatt     2100
catgctatcc cttccaacgc ttaccagttc cgaaatgtga tccctgcaag atggtctgtg    2160
agttcagccg tgttgccaaa ctatagactt gttgctgctc tccccatggc ctaccataat    2220
cagcgaatga ggtttcggac agatctgtcc tatggtgtgt acgggttcgc tgaaatcaat    2280
cccatcgctc tggttgagaa acctgccctg tcttggaaat ccagactgag acggaagaac   2340
```

```
tcttccatcg ctctcgcaaa catggaagat ggtggtagtg ttggaaggag taacgacatc      2400
cctgggagga gggctagatt tattggtgag aaagccgaag atcctcctgc tccatctcct      2460
agacccgcct tg                                                          2472
```

<210> SEQ ID NO 20
<211> LENGTH: 824
<212> TYPE: PRT
<213> ORGANISM: Artificial Sequence
<220> FEATURE:
<223> OTHER INFORMATION: Synthetic Construct

<400> SEQUENCE: 20

```
Pro Leu Leu Thr Ile Gly Asp Gln Phe Pro Ala Tyr Glu Leu Thr Ala
1               5                   10                  15

Leu Ile Ala Gly Asp Leu Ser Lys Val Asp Ala Lys Gln Pro Gly Asp
            20                  25                  30

Tyr Phe Thr Thr Val Thr Ser Glu Asp His Ala Gly Lys Trp Arg Val
        35                  40                  45

Val Phe Phe Trp Pro Lys Asp Phe Thr Phe Val Cys Pro Thr Glu Ile
    50                  55                  60

Ala Thr Phe Gly Lys Leu Asn Asp Glu Phe Glu Asp Arg Asp Ala Gln
65                  70                  75                  80

Val Leu Gly Val Ser Ile Asp Ser Glu Phe Val His Phe Asn Trp Arg
                85                  90                  95

Ala Gln His Glu Asp Leu Lys Asn Leu Pro Phe Pro Met Leu Ser Asp
            100                 105                 110

Ile Lys Arg Glu Leu Ser Leu Ala Thr Gly Val Leu Asn Ala Asp Gly
        115                 120                 125

Val Ala Asp Arg Ala Thr Phe Ile Val Asp Pro Asn Asn Glu Ile Gln
    130                 135                 140

Phe Val Ser Val Thr Ala Gly Ser Val Gly Arg Asn Val Glu Glu Val
145                 150                 155                 160

Leu Arg Val Leu Asp Ala Leu Gln Ser Asp Glu Leu Cys Ala Cys Asn
                165                 170                 175

Trp Arg Lys Gly Asp Pro Thr Leu Asn Ala Thr Glu Leu Leu Lys Ala
            180                 185                 190

Ser Ala Leu Gly Ser Ile Val Gly Gln Thr Tyr Arg Glu Val Glu Val
        195                 200                 205

Val Leu Val Asp Gly Gly Ser Thr Asp Arg Thr Leu Asp Ile Ala Asn
    210                 215                 220

Ser Phe Arg Pro Glu Leu Gly Ser Arg Leu Val Val His Ser Gly Pro
225                 230                 235                 240

Asp Asp Gly Pro Tyr Asp Ala Met Asn Arg Gly Val Gly Val Ala Thr
                245                 250                 255

Gly Glu Trp Val Leu Phe Leu Gly Ala Asp Asp Thr Leu Tyr Glu Pro
            260                 265                 270

Thr Thr Leu Ala Gln Val Ala Ala Phe Leu Gly Asp His Ala Ala Ser
        275                 280                 285

His Leu Val Tyr Gly Asp Val Val Met Arg Ser Thr Lys Ser Arg His
    290                 295                 300

Ala Gly Pro Phe Asp Leu Asp Arg Leu Leu Phe Glu Thr Asn Leu Cys
305                 310                 315                 320

His Gln Ser Ile Phe Tyr Arg Arg Glu Leu Phe Asp Gly Ile Gly Pro
                325                 330                 335
```

-continued

```
Tyr Asn Leu Arg Tyr Arg Val Trp Ala Asp Trp Asp Phe Asn Ile Arg
            340                 345                 350

Cys Phe Ser Asn Pro Ala Leu Ile Thr Arg Tyr Met Asp Val Val Ile
            355                 360                 365

Ser Glu Tyr Asn Asp Met Thr Gly Phe Ser Met Arg Gln Gly Thr Asp
            370                 375                 380

Lys Glu Phe Arg Lys Arg Leu Pro Met Tyr Phe Trp Val Ala Gly Trp
385                 390                 395                 400

Glu Thr Cys Arg Arg Met Leu Ala Phe Leu Lys Asp Lys Glu Asn Arg
                405                 410                 415

Arg Leu Ala Leu Arg Thr Arg Leu Ile Arg Val Lys Ala Val Ser Lys
            420                 425                 430

Glu Arg Ser Ala Glu Pro Arg Ile Arg Arg His Arg His Ala Glu Ile
        435                 440                 445

Ile Leu Ser Met Pro Gly Phe Gly Val Ile Leu Gly Ala Glu Phe Leu
    450                 455                 460

Ala Ala Thr Gly Gly Asp Met Ala Ala Phe Ala Ser Ala Asp Arg Leu
465                 470                 475                 480

Ala Gly Val Ala Gly Leu Ala Pro Val Pro Arg Asp Ser Gly Arg Ile
                485                 490                 495

Ser Gly Asn Leu Lys Arg Pro Arg Arg Tyr Asp Arg Arg Leu Leu Arg
            500                 505                 510

Ala Cys Tyr Leu Ser Ala Leu Val Ser Ile Arg Thr Asp Pro Ser Ser
        515                 520                 525

Arg Thr Tyr Tyr Asp Arg Lys Arg Thr Glu Gly Lys Arg His Thr Gln
    530                 535                 540

Ala Val Leu Ala Leu Ala Arg Arg Leu Asn Val Leu Trp Ala Met
545                 550                 555                 560

Leu Arg Asp His Ala Val Tyr His Pro Ala Thr Thr Ala Ala Ala
                565                 570                 575

Arg Leu Lys Leu Arg Arg Gly Glu Arg Pro Met Ser Leu Gly Gln Val
            580                 585                 590

Phe Asp Pro Arg Ala Asn Ala Leu His Ser Phe Pro Leu Thr Gly Arg
        595                 600                 605

Met Pro Trp Ala Pro Phe Ile Val Ser Ser Trp Leu Arg Asn Pro His
    610                 615                 620

Pro Ala Gln Tyr Phe Thr Ala Arg Cys Leu Arg Ile Leu Pro Gly Leu
625                 630                 635                 640

Trp Ile Gly Ala Gln Gly Gly Ser Ala Ala Lys Leu Leu Met Ser Gly
                645                 650                 655

Ala Pro Ile Glu Tyr Val Leu Lys Asp Ser Ala Val Trp Met Phe Lys
            660                 665                 670

Phe Asp Ile Gly Gly Thr Pro Arg Asp Ile Pro Val Ala Gly Ile Trp
        675                 680                 685

Asn Gly Ser Leu Trp Thr Pro Ala Trp Gly Ile His Ala Ile Ala
    690                 695                 700

Ser Asn Ala Tyr Gln Phe Arg Asn Val Ile Pro Ala Arg Trp Ser Val
705                 710                 715                 720

Ser Ser Ala Val Leu Pro Asn Tyr Arg Leu Val Ala Ala Leu Pro Met
                725                 730                 735

Ala Tyr His Asn Gln Arg Met Arg Phe Arg Thr Asp Leu Ser Tyr Gly
            740                 745                 750
```

```
Val Tyr Gly Phe Ala Glu Ile Asn Pro Ile Ala Leu Val Glu Lys Pro
        755                 760                 765

Ala Leu Ser Trp Lys Ser Arg Leu Arg Arg Lys Asn Ser Ser Ile Ala
770                 775                 780

Leu Ala Asn Met Glu Asp Gly Gly Ser Val Gly Arg Ser Asn Asp Ile
785                 790                 795                 800

Pro Gly Arg Arg Ala Arg Phe Ile Gly Glu Lys Ala Glu Asp Pro Pro
                805                 810                 815

Ala Pro Ser Pro Arg Pro Ala Leu
            820

<210> SEQ ID NO 21
<211> LENGTH: 2523
<212> TYPE: DNA
<213> ORGANISM: Artificial Sequence
<220> FEATURE:
<223> OTHER INFORMATION: Synthetic Construct

<400> SEQUENCE: 21
```

| | | | | |
|---|---|---|---|---|
| atgcagatct | tcgtcaaact | gccccttctc | actatcggag | accagttccc cgcttacgaa | 60 |
| cttacagctc | ttatcgctgg | agatctgagt | aaggttgacg | ccaaacagcc cggcgattat | 120 |
| ttcactaccg | ttaccagtga | ggatcacgca | ggtaaatgga | gagtcgtctt cttctggcct | 180 |
| aaagacttca | cctttgtgtg | ccctactgag | atcgcaacat | tcgggaagct gaacgatgag | 240 |
| ttcgaagatc | gagacgcaca | ggttttgggc | gtgtctatcg | attccgagtt cgtgcacttc | 300 |
| aactggagag | cacagcatga | agatctcaag | aaccttccat | tccccatgct cagcgacatc | 360 |
| aagagagaac | tgagcttggc | aacaggtgtt | ctgaatgctg | atggcgttgc tgacagagca | 420 |
| acattcattg | ttgaccccaa | taacgagatc | cagttcgttt | ccgttactgc tggttctgtc | 480 |
| ggtagaaacg | ttgaagaggt | cctgagagtt | ctcgacgcac | ttcagagtga tgaactgtgt | 540 |
| gcctgcaatt | ggcggaaagg | agatcctact | ctcaatgcca | cagagctgct taaagcaagt | 600 |
| gctctcggat | ccattgtcgg | acagacctat | agagaggtgg | aagttgtcct ggtcgatggt | 660 |
| ggatctacag | ataggactct | cgacattgcc | aactccttta | gaccagagct cggttcaagg | 720 |
| ctcgttgttc | attctggacc | agatgatgga | ccatacgacg | ccatgaacag aggtgttgga | 780 |
| gttgctacag | agaatgggt  | cttgttcctt | ggagctgatg | acactctgta cgaaccgact | 840 |
| acattggctc | aggttgcagc | attttgggga | gatcatgcag | cttctcacct tgtgtacgga | 900 |
| gatgtggtca | tgagatccac | caagtccaga | catgctggac | cattcgatct tgacagactc | 960 |
| ctgttcgaga | ccaacctctg | tcatcagagc | atcttctaca | acgggaact cttcgacgga | 1020 |
| attggaccttt | acaacctcag | gtacagggtt | tgggcagact | gggatttcaa catcaggtgc | 1080 |
| ttctcgaacc | cagctttgat | cacacggtac | atggatgttg | tgatctccga gtacaacgat | 1140 |
| atgaccggct | ctccatgag  | acagggaacc | gacaaagagt | tcaggaagcg cttgccaatg | 1200 |
| tacttctggg | ttgctggatg | ggaaacatgt | cggagaatgc | ttgctttcct gaaggacaag | 1260 |
| gagaacagga | gacttgctct | caggactaga | ctcatcaggg | tcaaagcagt gtccaaggaa | 1320 |
| aggagtgctg | aacctagaat | tcggagacat | agacatgcag | agatcatcct gagcatgcct | 1380 |
| ggatttggcg | ttatcctcgg | agctgaattt | cttgcagcaa | caggaggtga tatggcagct | 1440 |
| ttcgcatcag | ctgacagatt | ggctggagtt | gcaggtttgg | ctccagttcc aagagattca | 1500 |
| gggagaatca | gcggtaacct | caagagacct | agacgctacg | acagaagact gcttagagcc | 1560 |
| tgctatctga | gtgctttggt | tagcattaga | accgacccct | ctagtcgaac ctactacgat | 1620 |

-continued

```
aggaagcgga ctgaaggtaa gagacatacc caggcagtgt tggcacttgc tagaagacgg    1680
cttaatgttc tgtgggctat gctgagagat catgccgtgt accatcctgc taccacaaca    1740
gctgctgcta gacttaagct tcgcagaggt gagagaccta tgagtcttgg ccaggtcttt    1800
gatcctagag ctaatgcact gcactctttc cctcttacag gacgcatgcc ttgggctcca    1860
tttatcgtta gttcctggct cagaaaccct catccagctc agtacttcac agccagatgt    1920
ctcagaatcc ttcctggtct ttggattgga gcacagggtg gttccgcagc taagctgttg    1980
atgagtggtg caccaatcga atacgtcctg aaagactcag cagtgtggat gttcaagttc    2040
gacattggag aacaccaag ggatattcct gtcgctggta tctggaatgg aagtttgtgg    2100
accccagcat ggggaggtat tcatgctatc gcttccaacg cttaccagtt ccgaaatgtg    2160
atccctgcaa gatggtctgt gagttcagcc gtgttgccaa actatagact tgttgctgct    2220
ctccccatgg cctaccataa tcagcgaatg aggtttcgga cagatctgtc ctatggtgtg    2280
tacgggttcg ctgaaatcaa tcccatcgct ctggttgaga aacctgccct gtcttggaaa    2340
tccagactga gacggaagaa ctcttccatc gctctcgcaa acatggaaga tggtggtagt    2400
gttggaagga gtaacgacat ccctgggagg agggctagat ttattggtga aaagccgaa    2460 gatcctcctg ctccatctcc tagacccgcc ttggaggatt ccaaaccctc ttctcggtct    2520
tga                                                                    2523
```

<210> SEQ ID NO 22
<211> LENGTH: 840
<212> TYPE: PRT
<213> ORGANISM: Artificial Sequence
<220> FEATURE:
<223> OTHER INFORMATION: Synthetic Construct

<400> SEQUENCE: 22

```
Met Gln Ile Phe Val Lys Leu Pro Leu Leu Thr Ile Gly Asp Gln Phe
1               5                   10                  15

Pro Ala Tyr Glu Leu Thr Ala Leu Ile Ala Gly Asp Leu Ser Lys Val
            20                  25                  30

Asp Ala Lys Gln Pro Gly Asp Tyr Phe Thr Thr Val Thr Ser Glu Asp
        35                  40                  45

His Ala Gly Lys Trp Arg Val Val Phe Phe Trp Pro Lys Asp Phe Thr
    50                  55                  60

Phe Val Cys Pro Thr Glu Ile Ala Thr Phe Gly Lys Leu Asn Asp Glu
65                  70                  75                  80

Phe Glu Asp Arg Asp Ala Gln Val Leu Gly Val Ser Ile Asp Ser Glu
                85                  90                  95

Phe Val His Phe Asn Trp Arg Ala Gln His Glu Asp Leu Lys Asn Leu
            100                 105                 110

Pro Phe Pro Met Leu Ser Asp Ile Lys Arg Glu Leu Ser Leu Ala Thr
        115                 120                 125

Gly Val Leu Asn Ala Asp Gly Val Ala Asp Arg Ala Thr Phe Ile Val
    130                 135                 140

Asp Pro Asn Asn Glu Ile Gln Phe Val Ser Val Thr Ala Gly Ser Val
145                 150                 155                 160

Gly Arg Asn Val Glu Glu Val Leu Arg Val Leu Asp Ala Leu Gln Ser
                165                 170                 175

Asp Glu Leu Cys Ala Cys Asn Trp Arg Lys Gly Asp Pro Thr Leu Asn
            180                 185                 190

Ala Thr Glu Leu Leu Lys Ala Ser Ala Leu Gly Ser Ile Val Gly Gln
```

-continued

```
            195                 200                 205
Thr Tyr Arg Glu Val Glu Val Leu Val Asp Gly Gly Ser Thr Asp
    210                 215                 220

Arg Thr Leu Asp Ile Ala Asn Ser Phe Arg Pro Glu Leu Gly Ser Arg
225                 230                 235                 240

Leu Val Val His Ser Gly Pro Asp Asp Gly Pro Tyr Asp Ala Met Asn
                245                 250                 255

Arg Gly Val Gly Val Ala Thr Gly Glu Trp Val Leu Phe Leu Gly Ala
                260                 265                 270

Asp Asp Thr Leu Tyr Glu Pro Thr Thr Leu Ala Gln Val Ala Ala Phe
            275                 280                 285

Leu Gly Asp His Ala Ala Ser His Leu Val Tyr Gly Asp Val Val Met
        290                 295                 300

Arg Ser Thr Lys Ser Arg His Ala Gly Pro Phe Asp Leu Asp Arg Leu
305                 310                 315                 320

Leu Phe Glu Thr Asn Leu Cys His Gln Ser Ile Phe Tyr Arg Arg Glu
                325                 330                 335

Leu Phe Asp Gly Ile Gly Pro Tyr Asn Leu Arg Tyr Arg Val Trp Ala
                340                 345                 350

Asp Trp Asp Phe Asn Ile Arg Cys Phe Ser Asn Pro Ala Leu Ile Thr
            355                 360                 365

Arg Tyr Met Asp Val Val Ile Ser Glu Tyr Asn Asp Met Thr Gly Phe
        370                 375                 380

Ser Met Arg Gln Gly Thr Asp Lys Glu Phe Arg Lys Arg Leu Pro Met
385                 390                 395                 400

Tyr Phe Trp Val Ala Gly Trp Glu Thr Cys Arg Arg Met Leu Ala Phe
                405                 410                 415

Leu Lys Asp Lys Glu Asn Arg Arg Leu Ala Leu Arg Thr Arg Leu Ile
                420                 425                 430

Arg Val Lys Ala Val Ser Lys Glu Arg Ser Ala Glu Pro Arg Ile Arg
            435                 440                 445

Arg His Arg His Ala Glu Ile Ile Leu Ser Met Pro Gly Phe Gly Val
        450                 455                 460

Ile Leu Gly Ala Glu Phe Leu Ala Ala Thr Gly Gly Asp Met Ala Ala
465                 470                 475                 480

Phe Ala Ser Ala Asp Arg Leu Ala Gly Val Ala Gly Leu Ala Pro Val
                485                 490                 495

Pro Arg Asp Ser Gly Arg Ile Ser Gly Asn Leu Lys Arg Pro Arg Arg
                500                 505                 510

Tyr Asp Arg Arg Leu Leu Arg Ala Cys Tyr Leu Ser Ala Leu Val Ser
            515                 520                 525

Ile Arg Thr Asp Pro Ser Ser Arg Thr Tyr Tyr Asp Arg Lys Arg Thr
        530                 535                 540

Glu Gly Lys Arg His Thr Gln Ala Val Leu Ala Leu Ala Arg Arg Arg
545                 550                 555                 560

Leu Asn Val Leu Trp Ala Met Leu Arg Asp His Ala Val Tyr His Pro
                565                 570                 575

Ala Thr Thr Thr Ala Ala Ala Arg Leu Lys Leu Arg Arg Gly Glu Arg
                580                 585                 590

Pro Met Ser Leu Gly Gln Val Phe Asp Pro Arg Ala Asn Ala Leu His
            595                 600                 605

Ser Phe Pro Leu Thr Gly Arg Met Pro Trp Ala Pro Phe Ile Val Ser
        610                 615                 620
```

| Ser | Trp | Leu | Arg | Asn | Pro | His | Pro | Ala | Gln | Tyr | Phe | Thr | Ala | Arg | Cys |
| 625 | | | | 630 | | | | | 635 | | | | | 640 | |

Leu Arg Ile Leu Pro Gly Leu Trp Ile Gly Ala Gln Gly Gly Ser Ala
                    645                 650                 655

Ala Lys Leu Leu Met Ser Gly Ala Pro Ile Glu Tyr Val Leu Lys Asp
                660                 665                 670

Ser Ala Val Trp Met Phe Lys Phe Asp Ile Gly Thr Pro Arg Asp
            675                 680                 685

Ile Pro Val Ala Gly Ile Trp Asn Gly Ser Leu Trp Thr Pro Ala Trp
        690                 695                 700

Gly Gly Ile His Ala Ile Ala Ser Asn Ala Tyr Gln Phe Arg Asn Val
705                 710                 715                 720

Ile Pro Ala Arg Trp Ser Val Ser Ser Ala Val Leu Pro Asn Tyr Arg
                    725                 730                 735

Leu Val Ala Ala Leu Pro Met Ala Tyr His Asn Gln Arg Met Arg Phe
                740                 745                 750

Arg Thr Asp Leu Ser Tyr Gly Val Tyr Gly Phe Ala Glu Ile Asn Pro
            755                 760                 765

Ile Ala Leu Val Glu Lys Pro Ala Leu Ser Trp Lys Ser Arg Leu Arg
        770                 775                 780

Arg Lys Asn Ser Ser Ile Ala Leu Ala Asn Met Glu Asp Gly Gly Ser
785                 790                 795                 800

Val Gly Arg Ser Asn Asp Ile Pro Gly Arg Arg Ala Arg Phe Ile Gly
                    805                 810                 815

Glu Lys Ala Glu Asp Pro Pro Ala Pro Ser Pro Arg Pro Ala Leu Glu
                820                 825                 830

Asp Ser Lys Pro Ser Ser Arg Ser
            835                 840

<210> SEQ ID NO 23
<211> LENGTH: 2522
<212> TYPE: DNA
<213> ORGANISM: Artificial Sequence
<220> FEATURE:
<223> OTHER INFORMATION: Synthetic Construct

<400> SEQUENCE: 23
atgcagatct tcgtcaaact gccccttctc actatcggag accagttccc cgcttacgaa      60
cttacagctc ttatcgctgg agatctgagt aaggttgacg ccaaacagcc cggcgattat     120
ttcactaccg ttaccagtga ggatcacgca ggtaaatgga gagtcgtctt cttctggcct     180
aaagacttca cctttgtgtg ccctactgag atcgcaacat tcgggaagct gaacgatgag     240
ttcgaagatc gagacgcaca ggttttgggc gtgtctatcg attccgagtt cgtgcacttc     300
aactggagag cacagcatga agatctcaag aaccttccat tccccatgct cagcgacatc     360
aagagagaac tgagcttggc aacaggtgtt ctgaatgctg atggcgttgc tgacagagca     420
acattcattg ttgaccccaa taacgagatc cagttcgttt ccgttactgc tggttctgtc     480
ggtagaaacg ttgaagaggt cctgagagtt ctcgacgcac ttcagagtga tgaactgtgt     540
gcctgcaatt ggcggaaagg agatcctact ctcaatgcca cagagctgct taaagcaagt     600
gctctcggat ccattgtcgg acagacctat agagaggtgg aagttgtcct ggtcgatggt     660
ggatctacag ataggactct cgacattgcc aactccttta gaccagagct cggttcaagg     720
ctcgttgttc attctggacc agatgatgga ccatacgacg ccatgaacag aggtgttgga     780

```
gttgctacag gagaatgggt cttgttcctt ggagctgatg acactctgta cgaaccgact    840
acattggctc aggttgcagc attttgggga gatcatgcag cttctcacct tgtgtacgga    900
gatgtggtca tgagatccac caagtccaga catgctggac cattcgatct tgacagactc    960
ctgttcgaga ccaacctctg tcatcagagc atcttctaca gacgggaact cttcgacgga   1020
attggacctt acaacctcag gtacagggtt tgggcagact gggatttcaa catcaggtgc   1080
ttctcgaacc cagctttgat cacacggtac atggatgttg tgatctccga gtacaacgat   1140
atgaccggct ctccatgag acagggaacc gacaaagagt tcaggaagcg cttgccaatg   1200
tacttctggg ttgctggatg ggaaacatgt cggagaatgc ttgctttcct gaaggacaag   1260
gagaacagga gacttgctct caggactaga ctcatcaggg tcaaagcagt gtccaaggaa   1320
aggagtgctg aacctagaat tcggagacat agacatgcag agatcatcct gagcatgcct   1380
ggatttggcg ttatcctcgg agctgaattt cttgcagcaa caggaggtga tatggcagct   1440
ttcgcatcag ctgacagatt ggctggagtt gcaggtttgg ctccagttcc aagagattca   1500
gggagaatca gcggtaacct caagagacct agacgctacg cagaagact gcttagagcc   1560
tgctatctga gtgctttggt tagcattaga accgacccct ctagtcgaac ctactacgat   1620
aggaagcgga ctgaaggtaa gagacatacc caggcagtgt tggcacttgc tagaagacgg   1680
cttaatgttc tgtgggctat gctgagagat catgccgtgt accatcctgc taccacaaca   1740
gctgctgcta gacttaagct tcgcagaggt gagagaccta tgagtcttgg ccaggtcttt   1800
gatcctagag ctaatgcact gcactctttc cctcttacag gacgcatgcc ttgggctcca   1860
tttatcgtta gttcctggct cagaaaccct catccagctc agtacttcac agccagatgt   1920
ctcagaatcc ttcctggtct ttggattgga gcacagggtg gttccgcagc taagctgttg   1980
atgagtggtg caccaatcga atacgtcctg aaagactcag cagtgtggat gttcaagttc   2040
gacattggag aacaccaag ggatattcct gtcgctggta tctggaatgg aagtttgtgg   2100
accccagcat ggggaggtat tcatgctatc gcttccaacg cttaccagtt ccgaaatgtg   2160
atccctgcaa gatggtctgt gagttcagcc gtgttgccaa actatagact tgttgctgct   2220
ctccccatgg cctaccataa tcagcgaatg aggtttcgga cagatctgtc ctatggtgtg   2280
tacgggttcg ctgaaatcaa tcccatcgct ctggttgaga aacctgccct gtcttggaaa   2340
tccagactga cacggaagaa ctcttccatc gctctcgcaa acatggaaga tggtggtagt   2400
gttggaagga gtaacgacat ccctggggagg agggctagat ttattggtga gaaagccgaa   2460
gatcctcctg ctccatctcc tagacccgcc ttgaggattc aaaccctct tctcggtctt   2520
ga                                                                   2522
```

<210> SEQ ID NO 24
<211> LENGTH: 840
<212> TYPE: PRT
<213> ORGANISM: Artificial Sequence
<220> FEATURE:
<223> OTHER INFORMATION: Synthetic Construct

<400> SEQUENCE: 24

Met Gln Ile Phe Val Lys Pro Leu Leu Thr Ile Gly Asp Gln Phe Pro
1               5                   10                  15

Ala Tyr Glu Leu Thr Ala Leu Ile Ala Gly Asp Leu Ser Lys Val Asp
            20                  25                  30

Ala Lys Gln Pro Gly Asp Tyr Phe Thr Thr Val Thr Ser Glu Asp His
        35                  40                  45

```
Ala Gly Lys Trp Arg Val Val Phe Phe Trp Pro Lys Asp Phe Thr Phe
 50                  55                  60

Val Cys Pro Thr Glu Ile Ala Thr Phe Gly Lys Leu Asn Asp Glu Phe
 65                      70                  75                  80

Glu Asp Arg Asp Ala Gln Val Leu Gly Val Ser Ile Asp Ser Glu Phe
                     85                  90                  95

Val His Phe Asn Trp Arg Ala Gln His Glu Asp Leu Lys Asn Leu Pro
             100                 105                 110

Phe Pro Met Leu Ser Asp Ile Lys Arg Glu Leu Ser Leu Ala Thr Gly
         115                 120                 125

Val Leu Asn Ala Asp Gly Val Ala Asp Arg Ala Thr Phe Ile Val Asp
     130                 135                 140

Pro Asn Asn Glu Ile Gln Phe Val Ser Val Thr Ala Gly Ser Val Gly
145                 150                 155                 160

Arg Asn Val Glu Glu Val Leu Arg Val Leu Asp Ala Leu Gln Ser Asp
                 165                 170                 175

Glu Leu Cys Ala Cys Asn Trp Arg Lys Gly Asp Pro Thr Leu Asn Ala
             180                 185                 190

Thr Glu Leu Leu Lys Ala Ser Ala Leu Gly Ser Ile Val Gly Gln Thr
         195                 200                 205

Tyr Arg Glu Val Glu Val Leu Val Asp Gly Gly Ser Thr Asp Arg
210                 215                 220

Thr Leu Asp Ile Ala Asn Ser Phe Arg Pro Glu Leu Gly Ser Arg Leu
225                 230                 235                 240

Val Val His Ser Gly Pro Asp Asp Gly Pro Tyr Asp Ala Met Asn Arg
             245                 250                 255

Gly Val Gly Val Ala Thr Gly Glu Trp Val Leu Phe Leu Gly Ala Asp
         260                 265                 270

Asp Thr Leu Tyr Glu Pro Thr Thr Leu Ala Gln Val Ala Ala Phe Leu
     275                 280                 285

Gly Asp His Ala Ala Ser His Leu Val Tyr Gly Asp Val Val Met Arg
     290                 295                 300

Ser Thr Lys Ser Arg His Ala Gly Pro Phe Asp Leu Asp Arg Leu Leu
305                 310                 315                 320

Phe Glu Thr Asn Leu Cys His Gln Ser Ile Phe Tyr Arg Arg Glu Leu
                 325                 330                 335

Phe Asp Gly Ile Gly Pro Tyr Asn Leu Arg Tyr Arg Val Trp Ala Asp
             340                 345                 350

Trp Asp Phe Asn Ile Arg Cys Phe Ser Asn Pro Ala Leu Ile Thr Arg
         355                 360                 365

Tyr Met Asp Val Val Ile Ser Glu Tyr Asn Asp Met Thr Gly Phe Ser
     370                 375                 380

Met Arg Gln Gly Thr Asp Lys Glu Phe Arg Lys Arg Leu Pro Met Tyr
385                 390                 395                 400

Phe Trp Val Ala Gly Trp Glu Thr Cys Arg Arg Met Leu Ala Phe Leu
                 405                 410                 415

Lys Asp Lys Glu Asn Arg Arg Leu Ala Leu Arg Thr Arg Leu Ile Arg
             420                 425                 430

Val Lys Ala Val Ser Lys Glu Arg Ser Ala Glu Pro Arg Ile Arg Arg
         435                 440                 445

His Arg His Ala Glu Ile Ile Leu Ser Met Pro Gly Phe Gly Val Ile
     450                 455                 460

Leu Gly Ala Glu Phe Leu Ala Ala Thr Gly Gly Asp Met Ala Ala Phe
```

```
                465                 470                 475                 480
Ala Ser Ala Asp Arg Leu Ala Gly Val Ala Gly Leu Ala Pro Val Pro
            485                 490                 495

Arg Asp Ser Gly Arg Ile Ser Gly Asn Leu Lys Arg Pro Arg Arg Tyr
            500                 505                 510

Asp Arg Arg Leu Leu Arg Ala Cys Tyr Leu Ser Ala Leu Val Ser Ile
            515                 520                 525

Arg Thr Asp Pro Ser Ser Arg Thr Tyr Tyr Asp Arg Lys Arg Thr Glu
            530                 535                 540

Gly Lys Arg His Thr Gln Ala Val Leu Ala Leu Ala Arg Arg Arg Leu
545                 550                 555                 560

Asn Val Leu Trp Ala Met Leu Arg Asp His Ala Val Tyr His Pro Ala
                565                 570                 575

Thr Thr Thr Ala Ala Ala Arg Leu Lys Leu Arg Arg Gly Glu Arg Pro
            580                 585                 590

Met Ser Leu Gly Gln Val Phe Asp Pro Arg Ala Asn Ala Leu His Ser
            595                 600                 605

Phe Pro Leu Thr Gly Arg Met Pro Trp Ala Pro Phe Ile Val Ser Ser
            610                 615                 620

Trp Leu Arg Asn Pro His Pro Ala Gln Tyr Phe Thr Ala Arg Cys Leu
625                 630                 635                 640

Arg Ile Leu Pro Gly Leu Trp Ile Gly Ala Gln Gly Gly Ser Ala Ala
            645                 650                 655

Lys Leu Leu Met Ser Gly Ala Pro Ile Glu Tyr Val Leu Lys Asp Ser
            660                 665                 670

Ala Val Trp Met Phe Lys Phe Asp Ile Gly Gly Thr Pro Arg Asp Ile
            675                 680                 685

Pro Val Ala Gly Ile Trp Asn Gly Ser Leu Trp Thr Pro Ala Trp Gly
            690                 695                 700

Gly Ile His Ala Ile Ala Ser Asn Ala Tyr Gln Phe Arg Asn Val Ile
705                 710                 715                 720

Pro Ala Arg Trp Ser Val Ser Ser Ala Val Leu Pro Asn Tyr Arg Leu
            725                 730                 735

Val Ala Ala Leu Pro Met Ala Tyr His Asn Gln Arg Met Arg Phe Arg
            740                 745                 750

Thr Asp Leu Ser Tyr Gly Val Tyr Gly Phe Ala Glu Ile Asn Pro Ile
            755                 760                 765

Ala Leu Val Glu Lys Pro Ala Leu Ser Trp Lys Ser Arg Leu Arg Arg
            770                 775                 780

Lys Asn Ser Ser Ile Ala Leu Ala Asn Met Glu Asp Gly Gly Ser Val
785                 790                 795                 800

Gly Arg Ser Asn Asp Ile Pro Gly Arg Ala Arg Phe Ile Gly Glu
            805                 810                 815

Lys Ala Glu Asp Pro Pro Ala Pro Ser Pro Arg Pro Ala Leu Arg Ile
            820                 825                 830

Pro Asn Pro Leu Leu Gly Leu Asp
            835                 840

<210> SEQ ID NO 25
<211> LENGTH: 9
<212> TYPE: PRT
<213> ORGANISM: Mycobacterium avium subsp. paratuberculosis

<400> SEQUENCE: 25
```

Gly Phe Ala Glu Ile Asn Pro Ile Ala
1               5

<210> SEQ ID NO 26
<211> LENGTH: 2600
<212> TYPE: DNA
<213> ORGANISM: Artificial Sequence
<220> FEATURE:
<223> OTHER INFORMATION: Synthetic Construct

<400> SEQUENCE: 26

| | | | | | |
|---|---|---|---|---|---|
| tacccgggat | attctgcagt | caccgtattt | gacacgatgc | agatcttcgt | caaactgccc | 60 |
| cttctcacta | tcggagacca | gttccccgct | tacgaactta | cagctcttat | cgctggagat | 120 |
| ctgagtaagg | ttgacgccaa | acagcccggc | gattatttca | ctaccgttac | cagtgaggat | 180 |
| cacgcaggta | aatggagagt | cgtcttcttc | tggcctaaag | acttcacctt | tgtgtgccct | 240 |
| actgagatcg | caacattcgg | gaagctgaac | gatgagttcg | aagatcgaga | cgcacaggtt | 300 |
| ttgggcgtgt | ctatcgattc | cgagttcgtg | cacttcaact | ggagagcaca | gcatgaagat | 360 |
| ctcaagaacc | ttccattccc | catgctcagc | gacatcaaga | gagaactgag | cttggcaaca | 420 |
| ggtgttctga | atgctgatgg | cgttgctgac | agagcaacat | tcattgttga | ccccaataac | 480 |
| gagatccagt | tcgtttccgt | tactgctggt | tctgtcggta | gaaacgttga | agaggtcctg | 540 |
| agagttctcg | acgcacttca | gagtgatgaa | ctgtgtgcct | gcaattggcg | gaaaggagat | 600 |
| cctactctca | atgccacaga | gctgcttaaa | gcaagtgctc | tcggatccat | tgtcggacag | 660 |
| acctatagag | aggtggaagt | tgtcctggtc | gatggtggat | ctacagatag | gactctcgac | 720 |
| attgccaact | cctttagacc | agagctcggt | tcaaggctcg | ttgttcattc | tggaccagat | 780 |
| gatggaccat | acgacgccat | gaacagaggt | gttggagttg | ctacaggaga | atgggtcttg | 840 |
| ttccttggag | ctgatgacac | tctgtacgaa | ccgactacat | tggctcaggt | tgcagcattt | 900 |
| ttgggagatc | atgcagcttc | tcaccttgtg | tacgagatgt | ggtcatgag | atccaccaag | 960 |
| tccagacatg | ctggaccatt | cgatcttgac | agactcctgt | tcgagaccaa | cctctgtcat | 1020 |
| cagagcatct | tctacagacg | ggaactcttc | gacggaattg | accttacaa | cctcaggtac | 1080 |
| agggtttggg | cagactggga | tttcaacatc | aggtgcttct | cgaacccagc | tttgatcaca | 1140 |
| cggtacatgg | atgttgtgat | ctccgagtac | aacgatatga | ccggcttctc | catgagacag | 1200 |
| ggaaccgaca | aagagttcag | gaagcgcttg | ccaatgtact | tctgggttgc | tggatgggaa | 1260 |
| acatgtcgga | gaatgcttgc | tttcctgaag | gacaaggaga | acaggagact | tgctctcagg | 1320 |
| actagactca | tcagggtcaa | agcagtgtcc | aaggaaagga | gtgctgaacc | tagaattcgg | 1380 |
| agacatagac | atgcagagat | catcctgagc | atgcctggat | ttggcgttat | cctcggagct | 1440 |
| gaatttcttg | cagcaacagg | aggtgatatg | gcagctttcg | catcagctga | cagattggct | 1500 |
| ggagttgcag | gtttggctcc | agttccaaga | gattcaggga | gaatcagcgg | taacctcaag | 1560 |
| agacctagac | gctacgacag | aagactgctt | agagcctgct | atctgagtgc | tttggttagc | 1620 |
| attagaaccg | acccctctag | tcgaacctac | tacgatagga | agcggactga | aggtaagaga | 1680 |
| catacccagg | cagtgttggc | acttgctaga | agacggctta | atgttctgtg | ggctatgctg | 1740 |
| agagatcatg | ccgtgtacca | tcctgctacc | acaacagctg | ctgctagact | taagcttcgc | 1800 |
| agaggtgaga | gacctatgag | tcttggccag | gtctttgatc | ctagagctaa | tgcactgcac | 1860 |
| tctttccctc | ttacaggacg | catgcctgg | gctccattta | tcgttagttc | ctggctcaga | 1920 |
| aaccctcatc | cagctcagta | cttcacagcc | agatgtctca | gaatccttcc | tggtctttgg | 1980 |

```
attggagcac agggtggttc cgcagctaag ctgttgatga gtggtgcacc aatcgaatac    2040
gtcctgaaag actcagcagt gtggatgttc aagttcgaca ttggaggaac accaagggat    2100
attcctgtcg ctggtatctg gaatggaagt ttgtggaccc cagcatgggg aggtattcat    2160
gctatcgctt ccaacgctta ccagttccga aatgtgatcc ctgcaagatg gtctgtgagt    2220
tcagccgtgt tgccaaacta tagacttgtt gctgctctcc ccatggccta ccataatcag    2280
cgaatgaggt ttcggacaga tctgtcctat ggtgtgtacg ggttcgctga atcaatccc     2340 atcgctctgg ttgagaaacc tgccctgtct tggaaatcca gactgagacg gaagaactct    2400
tccatcgctc tcgcaaacat ggaagatggt ggtagtgttg aaggagtaa cgacatccct    2460 gggaggaggg ctagatttat tggtgagaaa gccgaagatc ctcctgctcc atctcctaga    2520
cccgccttga ggattccaaa ccctcttctc ggtcttgatt gaatatctag acagtgaccc    2580
gggatcgact agatcgatca                                                2600
```

<210> SEQ ID NO 27
<211> LENGTH: 840
<212> TYPE: PRT
<213> ORGANISM: Artificial Sequence
<220> FEATURE:
<223> OTHER INFORMATION: Synthetic Construct

<400> SEQUENCE: 27

```
Met Gln Ile Phe Val Lys Leu Pro Leu Leu Thr Ile Gly Asp Gln Phe
 1               5                  10                  15

Pro Ala Tyr Glu Leu Thr Ala Leu Ile Ala Gly Asp Leu Ser Lys Val
            20                  25                  30

Asp Ala Lys Gln Pro Gly Asp Tyr Phe Thr Thr Val Thr Ser Glu Asp
        35                  40                  45

His Ala Gly Lys Trp Arg Val Phe Phe Trp Pro Lys Asp Phe Thr
    50                  55                  60

Phe Val Cys Pro Thr Glu Ile Ala Thr Phe Gly Lys Leu Asn Asp Glu
65                  70                  75                  80

Phe Glu Asp Arg Asp Ala Gln Val Leu Gly Val Ser Ile Asp Ser Glu
                85                  90                  95

Phe Val His Phe Asn Trp Arg Ala Gln His Glu Asp Leu Lys Asn Leu
            100                 105                 110

Pro Phe Pro Met Leu Ser Asp Ile Lys Arg Glu Leu Ser Leu Ala Thr
        115                 120                 125

Gly Val Leu Asn Ala Asp Gly Val Ala Asp Arg Ala Thr Phe Ile Val
    130                 135                 140

Asp Pro Asn Asn Glu Ile Gln Phe Val Ser Val Thr Ala Gly Ser Val
145                 150                 155                 160

Gly Arg Asn Val Glu Glu Val Leu Arg Val Leu Asp Ala Leu Gln Ser
                165                 170                 175

Asp Glu Leu Cys Ala Cys Asn Trp Arg Lys Gly Asp Pro Thr Leu Asn
            180                 185                 190

Ala Thr Glu Leu Leu Lys Ala Ser Ala Leu Gly Ser Ile Val Gly Gln
        195                 200                 205

Thr Tyr Arg Glu Val Glu Val Val Leu Val Asp Gly Gly Ser Thr Asp
    210                 215                 220

Arg Thr Leu Asp Ile Ala Asn Ser Phe Arg Pro Glu Leu Gly Ser Arg
225                 230                 235                 240

Leu Val Val His Ser Gly Pro Asp Asp Gly Pro Tyr Asp Ala Met Asn
                245                 250                 255
```

-continued

Arg Gly Val Gly Val Ala Thr Gly Glu Trp Val Leu Phe Leu Gly Ala
            260                 265                 270

Asp Asp Thr Leu Tyr Glu Pro Thr Leu Ala Gln Val Ala Ala Phe
            275                 280                 285

Leu Gly Asp His Ala Ala Ser His Leu Val Tyr Gly Asp Val Val Met
            290                 295                 300

Arg Ser Thr Lys Ser Arg His Ala Gly Pro Phe Asp Leu Asp Arg Leu
305                 310                 315                 320

Leu Phe Glu Thr Asn Leu Cys His Gln Ser Ile Phe Tyr Arg Arg Glu
                325                 330                 335

Leu Phe Asp Gly Ile Gly Pro Tyr Asn Leu Arg Tyr Arg Val Trp Ala
            340                 345                 350

Asp Trp Asp Phe Asn Ile Arg Cys Phe Ser Asn Pro Ala Leu Ile Thr
            355                 360                 365

Arg Tyr Met Asp Val Val Ile Ser Glu Tyr Asn Asp Met Thr Gly Phe
            370                 375                 380

Ser Met Arg Gln Gly Thr Asp Lys Glu Phe Arg Lys Arg Leu Pro Met
385                 390                 395                 400

Tyr Phe Trp Val Ala Gly Trp Glu Thr Cys Arg Arg Met Leu Ala Phe
                405                 410                 415

Leu Lys Asp Lys Glu Asn Arg Arg Leu Ala Leu Arg Thr Arg Leu Ile
            420                 425                 430

Arg Val Lys Ala Val Ser Lys Glu Arg Ser Ala Glu Pro Arg Ile Arg
            435                 440                 445

Arg His Arg His Ala Glu Ile Ile Leu Ser Met Pro Gly Phe Gly Val
            450                 455                 460

Ile Leu Gly Ala Glu Phe Leu Ala Ala Thr Gly Gly Asp Met Ala Ala
465                 470                 475                 480

Phe Ala Ser Ala Asp Arg Leu Ala Gly Val Ala Gly Leu Ala Pro Val
                485                 490                 495

Pro Arg Asp Ser Gly Arg Ile Ser Gly Asn Leu Lys Arg Pro Arg Arg
            500                 505                 510

Tyr Asp Arg Arg Leu Leu Arg Ala Cys Tyr Leu Ser Ala Leu Val Ser
            515                 520                 525

Ile Arg Thr Asp Pro Ser Ser Arg Thr Tyr Tyr Asp Arg Lys Arg Thr
            530                 535                 540

Glu Gly Lys Arg His Thr Gln Ala Val Leu Ala Leu Ala Arg Arg Arg
545                 550                 555                 560

Leu Asn Val Leu Trp Ala Met Leu Arg Asp His Ala Val Tyr His Pro
                565                 570                 575

Ala Thr Thr Thr Ala Ala Ala Arg Leu Lys Leu Arg Arg Gly Glu Arg
            580                 585                 590

Pro Met Ser Leu Gly Gln Val Phe Asp Pro Arg Ala Asn Ala Leu His
            595                 600                 605

Ser Phe Pro Leu Thr Gly Arg Met Pro Trp Ala Pro Phe Ile Val Ser
            610                 615                 620

Ser Trp Leu Arg Asn Pro His Pro Ala Gln Tyr Phe Thr Ala Arg Cys
625                 630                 635                 640

Leu Arg Ile Leu Pro Gly Leu Trp Ile Gly Ala Gln Gly Gly Ser Ala
                645                 650                 655

Ala Lys Leu Leu Met Ser Gly Ala Pro Ile Glu Tyr Val Leu Lys Asp
            660                 665                 670

```
Ser Ala Val Trp Met Phe Lys Phe Asp Ile Gly Gly Thr Pro Arg Asp
        675                 680                 685

Ile Pro Val Ala Gly Ile Trp Asn Gly Ser Leu Trp Thr Pro Ala Trp
    690                 695                 700

Gly Gly Ile His Ala Ile Ala Ser Asn Ala Tyr Gln Phe Arg Asn Val
705                 710                 715                 720

Ile Pro Ala Arg Trp Ser Val Ser Ser Ala Val Leu Pro Asn Tyr Arg
                725                 730                 735

Leu Val Ala Ala Leu Pro Met Ala Tyr His Asn Gln Arg Met Arg Phe
            740                 745                 750

Arg Thr Asp Leu Ser Tyr Gly Val Tyr Gly Phe Ala Glu Ile Asn Pro
                755                 760                 765

Ile Ala Leu Val Glu Lys Pro Ala Leu Ser Trp Lys Ser Arg Leu Arg
    770                 775                 780

Arg Lys Asn Ser Ser Ile Ala Leu Ala Asn Met Glu Asp Gly Gly Ser
785                 790                 795                 800

Val Gly Arg Ser Asn Asp Ile Pro Gly Arg Arg Ala Arg Phe Ile Gly
                805                 810                 815

Glu Lys Ala Glu Asp Pro Pro Ala Pro Ser Pro Arg Pro Ala Leu Arg
            820                 825                 830

Ile Pro Asn Pro Leu Leu Gly Leu
        835                 840

<210> SEQ ID NO 28
<211> LENGTH: 15
<212> TYPE: PRT
<213> ORGANISM: Artificial Sequence
<220> FEATURE:
<223> OTHER INFORMATION: Synthetic Construct

<400> SEQUENCE: 28

Leu Pro Leu Leu Thr Ile Gly Asp Gln Phe Pro Ala Tyr Glu Leu
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Synthetic Construct

<400> SEQUENCE: 29

Ile Gly Asp Gln Phe Pro Ala Tyr Glu Leu Thr Ala Leu Ile Ala
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Synthetic Construct

<400> SEQUENCE: 30

Pro Ala Tyr Glu Leu Thr Ala Leu Ile Ala Gly Asp Leu Ser Lys
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthetic Construct
```

<400> SEQUENCE: 31

Thr Ala Leu Ile Ala Gly Asp Leu Ser Lys Val Asp Ala Lys Gln
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic Construct

<400> SEQUENCE: 32

Gly Asp Leu Ser Lys Val Asp Ala Lys Gln Pro Gly Asp Tyr Phe
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Synthetic Construct

<400> SEQUENCE: 33

Val Asp Ala Lys Gln Pro Gly Asp Tyr Phe Thr Thr Val Thr Ser
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic Construct

<400> SEQUENCE: 34

Pro Gly Asp Tyr Phe Thr Thr Val Thr Ser Glu Asp His Ala Gly
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthetic Construct

<400> SEQUENCE: 35

Thr Thr Val Thr Ser Glu Asp His Ala Gly Lys Trp Arg Val Val
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthetic Construct

<400> SEQUENCE: 36

Glu Asp His Ala Gly Lys Trp Arg Val Val Phe Phe Trp Pro Lys
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Synthetic Construct

```
<400> SEQUENCE: 37

Lys Trp Arg Val Val Phe Phe Trp Pro Lys Asp Phe Thr Phe Val
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Synthetic Construct

<400> SEQUENCE: 38

Phe Phe Trp Pro Lys Asp Phe Thr Phe Val Cys Pro Thr Glu Ile
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Synthetic Construct

<400> SEQUENCE: 39

Asp Phe Thr Phe Val Cys Pro Thr Glu Ile Ala Thr Phe Gly Lys
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Synthetic Construct

<400> SEQUENCE: 40

Cys Pro Thr Glu Ile Ala Thr Phe Gly Lys Leu Asn Asp Glu Phe
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Synthetic Construct

<400> SEQUENCE: 41

Ala Thr Phe Gly Lys Leu Asn Asp Glu Phe Glu Asp Arg Asp Ala
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Synthetic Construct

<400> SEQUENCE: 42

Leu Asn Asp Glu Phe Glu Asp Arg Asp Ala Gln Val Leu Gly Val
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Synthetic Construct

<400> SEQUENCE: 43
```

```
Glu Asp Arg Asp Ala Gln Val Leu Gly Val Ser Ile Asp Ser Glu
1               5                   10                  15
```

<210> SEQ ID NO 44
<211> LENGTH: 15
<212> TYPE: PRT
<213> ORGANISM: Artificial Sequence
<220> FEATURE:
<223> OTHER INFORMATION: Synthetic Construct

<400> SEQUENCE: 44

```
Gln Val Leu Gly Val Ser Ile Asp Ser Glu Phe Val His Phe Asn
1               5                   10                  15
```

<210> SEQ ID NO 45
<211> LENGTH: 15
<212> TYPE: PRT
<213> ORGANISM: Artificial Sequence
<220> FEATURE:
<223> OTHER INFORMATION: Synthetic Construct

<400> SEQUENCE: 45

```
Ser Ile Asp Ser Glu Phe Val His Phe Asn Trp Arg Ala Gln His
1               5                   10                  15
```

<210> SEQ ID NO 46
<211> LENGTH: 15
<212> TYPE: PRT
<213> ORGANISM: Artificial Sequence
<220> FEATURE:
<223> OTHER INFORMATION: Synthetic Construct

<400> SEQUENCE: 46

```
Phe Val His Phe Asn Trp Arg Ala Gln His Glu Asp Leu Lys Asn
1               5                   10                  15
```

<210> SEQ ID NO 47
<211> LENGTH: 15
<212> TYPE: PRT
<213> ORGANISM: Artificial Sequence
<220> FEATURE:
<223> OTHER INFORMATION: Synthetic Construct

<400> SEQUENCE: 47

```
Trp Arg Ala Gln His Glu Asp Leu Lys Asn Leu Pro Phe Pro Met
1               5                   10                  15
```

<210> SEQ ID NO 48
<211> LENGTH: 15
<212> TYPE: PRT
<213> ORGANISM: Artificial Sequence
<220> FEATURE:
<223> OTHER INFORMATION: Synthetic Construct

<400> SEQUENCE: 48

```
Glu Asp Leu Lys Asn Leu Pro Phe Pro Met Leu Ser Asp Ile Lys
1               5                   10                  15
```

<210> SEQ ID NO 49
<211> LENGTH: 15
<212> TYPE: PRT
<213> ORGANISM: Artificial Sequence
<220> FEATURE:
<223> OTHER INFORMATION: Synthetic Construct

<400> SEQUENCE: 49

```
Leu Pro Phe Pro Met Leu Ser Asp Ile Lys Arg Glu Leu Ser Leu
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetic Construct

<400> SEQUENCE: 50

Leu Ser Asp Ile Lys Arg Glu Leu Ser Leu Ala Thr Gly Val Leu
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Synthetic Construct

<400> SEQUENCE: 51

Arg Glu Leu Ser Leu Ala Thr Gly Val Leu Asn Ala Asp Gly Val
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Synthetic Construct

<400> SEQUENCE: 52

Ala Thr Gly Val Leu Asn Ala Asp Gly Val Ala Asp Arg Ala Thr
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Synthetic Construct

<400> SEQUENCE: 53

Asn Ala Asp Gly Val Ala Asp Arg Ala Thr Phe Ile Val Asp Pro
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Synthetic Construct

<400> SEQUENCE: 54

Ala Asp Arg Ala Thr Phe Ile Val Asp Pro Asn Asn Glu Ile Gln
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Synthetic Construct

<400> SEQUENCE: 55

Phe Ile Val Asp Pro Asn Asn Glu Ile Gln Phe Val Ser Val Thr
```

```
                1               5                  10                 15
```

<210> SEQ ID NO 56
<211> LENGTH: 15
<212> TYPE: PRT
<213> ORGANISM: Artificial Sequence
<220> FEATURE:
<223> OTHER INFORMATION: Synthetic Construct

<400> SEQUENCE: 56

```
Asn Asn Glu Ile Gln Phe Val Ser Val Thr Ala Gly Ser Val Gly
1               5                  10                 15
```

<210> SEQ ID NO 57
<211> LENGTH: 15
<212> TYPE: PRT
<213> ORGANISM: Artificial Sequence
<220> FEATURE:
<223> OTHER INFORMATION: Synthetic Construct

<400> SEQUENCE: 57

```
Phe Val Ser Val Thr Ala Gly Ser Val Gly Arg Asn Val Glu Glu
1               5                  10                 15
```

<210> SEQ ID NO 58
<211> LENGTH: 15
<212> TYPE: PRT
<213> ORGANISM: Artificial Sequence
<220> FEATURE:
<223> OTHER INFORMATION: Synthetic Construct

<400> SEQUENCE: 58

```
Ala Gly Ser Val Gly Arg Asn Val Glu Glu Val Leu Arg Val Leu
1               5                  10                 15
```

<210> SEQ ID NO 59
<211> LENGTH: 15
<212> TYPE: PRT
<213> ORGANISM: Artificial Sequence
<220> FEATURE:
<223> OTHER INFORMATION: Synthetic Construct

<400> SEQUENCE: 59

```
Arg Asn Val Glu Glu Val Leu Arg Val Leu Asp Ala Leu Gln Ser
1               5                  10                 15
```

<210> SEQ ID NO 60
<211> LENGTH: 15
<212> TYPE: PRT
<213> ORGANISM: Artificial Sequence
<220> FEATURE:
<223> OTHER INFORMATION: Synthetic Construct

<400> SEQUENCE: 60

```
Val Leu Arg Val Leu Asp Ala Leu Gln Ser Asp Glu Leu Cys Ala
1               5                  10                 15
```

<210> SEQ ID NO 61
<211> LENGTH: 15
<212> TYPE: PRT
<213> ORGANISM: Artificial Sequence
<220> FEATURE:
<223> OTHER INFORMATION: Synthetic Construct

<400> SEQUENCE: 61

```
Asp Ala Leu Gln Ser Asp Glu Leu Cys Ala Cys Asn Trp Arg Lys
1               5                  10                 15
```

-continued

<210> SEQ ID NO 62
<211> LENGTH: 15
<212> TYPE: PRT
<213> ORGANISM: Artificial Sequence
<220> FEATURE:
<223> OTHER INFORMATION: Synthetic Construct

<400> SEQUENCE: 62

Asp Glu Leu Cys Ala Cys Asn Trp Arg Lys Gly Asp Pro Thr Leu
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: Synthetic Construct

<400> SEQUENCE: 63

Cys Asn Trp Arg Lys Gly Asp Pro Thr Leu Asn Ala Thr Glu Leu
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: Synthetic Construct

<400> SEQUENCE: 64

Gly Asp Pro Thr Leu Asn Ala Thr Glu Leu Leu Lys Ala Ser Ala
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: Synthetic Construct

<400> SEQUENCE: 65

Asn Ala Thr Glu Leu Leu Lys Ala Ser Ala Leu Gly Ser Arg Ile
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: Synthetic Construct

<400> SEQUENCE: 66

Arg Arg Gly Glu Arg Pro Met Ser Leu Gly Gln Val Phe Asp Pro
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: Synthetic Construct

<400> SEQUENCE: 67

Pro Met Ser Leu Gly Gln Val Phe Asp Pro Arg Ala Asn Ala Leu
1               5                   10                  15

<210> SEQ ID NO 68
<211> LENGTH: 14
<212> TYPE: PRT
<213> ORGANISM: Artificial Sequence
<220> FEATURE:
<223> OTHER INFORMATION: Synthetic Construct

<400> SEQUENCE: 68

His Ser Phe Pro Leu Thr Gly Arg Met Pro Trp Ala Pro Phe
1               5                   10

<210> SEQ ID NO 69
<211> LENGTH: 15
<212> TYPE: PRT
<213> ORGANISM: Artificial Sequence
<220> FEATURE:
<223> OTHER INFORMATION: Synthetic Construct

<400> SEQUENCE: 69

Ile Val Ser Ser Trp Leu Arg Asn Pro His Pro Ala Gln Tyr Phe
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Synthetic Construct

<400> SEQUENCE: 70

Leu Arg Asn Pro His Pro Ala Gln Tyr Phe Thr Ala Arg Cys Leu
1               5                   10                  15

<210> SEQ ID NO 71
<211> LENGTH: 18
<212> TYPE: PRT
<213> ORGANISM: Artificial Sequence
<220> FEATURE:
<223> OTHER INFORMATION: Synthetic Construct

<400> SEQUENCE: 71

Pro Ala Gln Tyr Phe Thr Ala Arg Cys Leu Arg Ile Leu Pro Gly Leu
1               5                   10                  15

Trp Ile

<210> SEQ ID NO 72
<211> LENGTH: 15
<212> TYPE: PRT
<213> ORGANISM: Artificial Sequence
<220> FEATURE:
<223> OTHER INFORMATION: Synthetic Construct

<400> SEQUENCE: 72

Gly Ala Gln Gly Gly Ser Ala Ala Lys Leu Leu Met Ser Gly Ala
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Synthetic Construct

<400> SEQUENCE: 73

Ser Ala Ala Lys Leu Leu Met Ser Gly Ala Pro Ile Glu Tyr Val
1               5                   10                  15

```
<210> SEQ ID NO 74
<211> LENGTH: 15
<212> TYPE: PRT
<213> ORGANISM: Artificial Sequence
<220> FEATURE:
<223> OTHER INFORMATION: Synthetic Construct

<400> SEQUENCE: 74

Leu Met Ser Gly Ala Pro Ile Glu Tyr Val Leu Lys Asp Ser Ala
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Synthetic Construct

<400> SEQUENCE: 75

Pro Ile Glu Tyr Val Leu Lys Asp Ser Ala Val Trp Met Phe Lys
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Synthetic Construct

<400> SEQUENCE: 76

Leu Lys Asp Ser Ala Val Trp Met Phe Lys Phe Asp Ile Gly Gly
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Synthetic Construct

<400> SEQUENCE: 77

Val Trp Met Phe Lys Phe Asp Ile Gly Gly Thr Pro Arg Asp Ile
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Synthetic Construct

<400> SEQUENCE: 78

Phe Asp Ile Gly Gly Thr Pro Arg Asp Ile Pro Val Ala Gly Ile
1               5                   10                  15

<210> SEQ ID NO 79
<211> LENGTH: 17
<212> TYPE: PRT
<213> ORGANISM: Artificial Sequence
<220> FEATURE:
<223> OTHER INFORMATION: Synthetic Construct

<400> SEQUENCE: 79

Thr Pro Arg Asp Ile Pro Val Ala Gly Ile Trp Asn Gly Ser Leu Trp
1               5                   10                  15
```

Thr

<210> SEQ ID NO 80
<211> LENGTH: 13
<212> TYPE: PRT
<213> ORGANISM: Artificial Sequence
<220> FEATURE:
<223> OTHER INFORMATION: Synthetic Construct

<400> SEQUENCE: 80

Pro Ala Trp Gly Gly Ile His Ala Ile Ala Ser Asn Ala
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Synthetic Construct

<400> SEQUENCE: 81

Tyr Gln Phe Arg Asn Val Ile Pro Ala Arg Trp Ser
1               5                   10

<210> SEQ ID NO 82
<211> LENGTH: 15
<212> TYPE: PRT
<213> ORGANISM: Artificial Sequence
<220> FEATURE:
<223> OTHER INFORMATION: Synthetic Construct

<400> SEQUENCE: 82

Val Ser Ser Ala Val Leu Pro Asn Tyr Arg Leu Val Ala Ala Leu
1               5                   10                  15

<210> SEQ ID NO 83
<211> LENGTH: 14
<212> TYPE: PRT
<213> ORGANISM: Artificial Sequence
<220> FEATURE:
<223> OTHER INFORMATION: Synthetic Construct

<400> SEQUENCE: 83

Leu Pro Asn Tyr Arg Leu Val Ala Ala Leu Pro Met Ala Tyr
1               5                   10

<210> SEQ ID NO 84
<211> LENGTH: 16
<212> TYPE: PRT
<213> ORGANISM: Artificial Sequence
<220> FEATURE:
<223> OTHER INFORMATION: Synthetic Construct

<400> SEQUENCE: 84

His Asn Gln Arg Met Arg Phe Arg Thr Asp Leu Ser Tyr Gly Val Tyr
1               5                   10                  15

<210> SEQ ID NO 85
<211> LENGTH: 9
<212> TYPE: PRT
<213> ORGANISM: Artificial Sequence
<220> FEATURE:
<223> OTHER INFORMATION: Synthetic Construct

<400> SEQUENCE: 85

Gly Phe Ala Glu Ile Asn Pro Ile Ala
1               5

-continued

```
<210> SEQ ID NO 86
<211> LENGTH: 15
<212> TYPE: PRT
<213> ORGANISM: Artificial Sequence
<220> FEATURE:
<223> OTHER INFORMATION: Synthetic Construct

<400> SEQUENCE: 86

Leu Val Glu Lys Pro Ala Leu Ser Trp Lys Ser Arg Leu Arg Arg
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Synthetic Construct

<400> SEQUENCE: 87

Ala Leu Ser Trp Lys Ser Arg Leu Arg Arg Lys Asn Ser Ser Ile
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Synthetic Construct

<400> SEQUENCE: 88

Ser Arg Leu Arg Arg Lys Asn Ser Ser Ile Ala Leu Ala Asn Met
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Synthetic Construct

<400> SEQUENCE: 89

Lys Asn Ser Ser Ile Ala Leu Ala Asn Met Glu Asp Gly Gly Ser
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Synthetic Construct

<400> SEQUENCE: 90

Ala Leu Ala Asn Met Glu Asp Gly Gly Ser Val Gly Arg Ser Asn
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Synthetic Construct

<400> SEQUENCE: 91

Glu Asp Gly Gly Ser Val Gly Arg Ser Asn Asp Ile Pro Gly Arg
1               5                   10                  15
```

```
<210> SEQ ID NO 92
<211> LENGTH: 15
<212> TYPE: PRT
<213> ORGANISM: Artificial Sequence
<220> FEATURE:
<223> OTHER INFORMATION: Synthetic Construct

<400> SEQUENCE: 92

Val Gly Arg Ser Asn Asp Ile Pro Gly Arg Arg Ala Arg Phe Ile
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Synthetic Construct

<400> SEQUENCE: 93

Asp Ile Pro Gly Arg Arg Ala Arg Phe Ile Gly Glu Lys Ala Glu
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Synthetic Construct

<400> SEQUENCE: 94

Arg Ala Arg Phe Ile Gly Glu Lys Ala Glu Asp Pro Pro Ala Pro
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: Synthetic Construct

<400> SEQUENCE: 95

Gly Glu Lys Ala Glu Asp Pro Pro Ala Pro Ser Pro Arg Pro Ala Leu
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: Synthetic Construct

<400> SEQUENCE: 96

Arg Ile Arg Arg His Arg His Ala Glu Ile Ile Leu Ser Met Pro
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: Synthetic Construct

<400> SEQUENCE: 97

Arg His Ala Glu Ile Ile Leu Ser Met Pro Gly Phe Gly Val Ile
1               5                   10                  15
```

```
<210> SEQ ID NO 98
<211> LENGTH: 15
<212> TYPE: PRT
<213> ORGANISM: Artificial Sequence
<220> FEATURE:
<223> OTHER INFORMATION: Synthetic Construct

<400> SEQUENCE: 98

Ile Leu Ser Met Pro Gly Phe Gly Val Ile Leu Gly Ala Glu Phe
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: Synthetic Construct

<400> SEQUENCE: 99

Gly Phe Gly Val Ile Leu Gly Ala Glu Phe Leu Ala Ala Thr Gly
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Synthetic Construct

<400> SEQUENCE: 100

Leu Gly Ala Glu Phe Leu Ala Ala Thr Gly Gly Asp Met Ala Ala
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Synthetic Construct

<400> SEQUENCE: 101

Leu Ala Ala Thr Gly Gly Asp Met Ala Ala Phe Ala Ser Ala Asp
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: Synthetic Construct

<400> SEQUENCE: 102

Gly Asp Met Ala Ala Phe Ala Ser Ala Asp Arg Leu Ala Gly Val
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Synthetic Construct

<400> SEQUENCE: 103

Phe Ala Ser Ala Asp Arg Leu Ala Gly Val Ala Gly Leu Ala Pro
1               5                   10                  15

<210> SEQ ID NO 104
```

```
<211> LENGTH: 15
<212> TYPE: PRT
<213> ORGANISM: Artificial Sequence
<220> FEATURE:
<223> OTHER INFORMATION: Synthetic Construct

<400> SEQUENCE: 104

Arg Leu Ala Gly Val Ala Gly Leu Ala Pro Val Pro Arg Asp Ser
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Synthetic Construct

<400> SEQUENCE: 105

Ala Gly Leu Ala Pro Val Pro Arg Asp Ser Gly Arg Ile Ser Gly
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Synthetic Construct

<400> SEQUENCE: 106

Val Pro Arg Asp Ser Gly Arg Ile Ser Gly Asn Leu Lys Arg Pro
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Synthetic Construct

<400> SEQUENCE: 107

Gly Arg Ile Ser Gly Asn Leu Lys Arg Pro Arg Arg Tyr Asp Arg
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Synthetic Construct

<400> SEQUENCE: 108

Asn Leu Lys Arg Pro Arg Arg Tyr Asp Arg Arg Leu Leu Arg Ala
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Synthetic Construct

<400> SEQUENCE: 109

Arg Arg Tyr Asp Arg Arg Leu Leu Arg Ala Cys Tyr Leu Ser Ala
1               5                   10                  15

<210> SEQ ID NO 110
<211> LENGTH: 15
```

```
<212> TYPE: PRT
<213> ORGANISM: Artificial Sequence
<220> FEATURE:
<223> OTHER INFORMATION: Synthetic Construct

<400> SEQUENCE: 110

Arg Leu Leu Arg Ala Cys Tyr Leu Ser Ala Leu Val Ser Ile Arg
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Synthetic Construct

<400> SEQUENCE: 111

Cys Tyr Leu Ser Ala Leu Val Ser Ile Arg Thr Asp Pro Ser Ser
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: Synthetic Construct

<400> SEQUENCE: 112

Leu Val Ser Ile Arg Thr Asp Pro Ser Ser Arg Thr Tyr Tyr Asp
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Synthetic Construct

<400> SEQUENCE: 113

Thr Asp Pro Ser Ser Arg Thr Tyr Tyr Asp Arg Lys Arg Thr Glu
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Synthetic Construct

<400> SEQUENCE: 114

Arg Thr Tyr Tyr Asp Arg Lys Arg Thr Glu Gly Lys Arg His Thr
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Synthetic Construct

<400> SEQUENCE: 115

Arg Lys Arg Thr Glu Gly Lys Arg His Thr Gln Ala Val Leu Ala
1               5                   10                  15

<210> SEQ ID NO 116
<211> LENGTH: 15
<212> TYPE: PRT
```

```
<213> ORGANISM: Artificial Sequence
<220> FEATURE:
<223> OTHER INFORMATION: Synthetic Construct

<400> SEQUENCE: 116

Gly Lys Arg His Thr Gln Ala Val Leu Ala Leu Ala Arg Arg Arg
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Synthetic Construct

<400> SEQUENCE: 117

Gln Ala Val Leu Ala Leu Ala Arg Arg Arg Leu Asn Val Leu Trp
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: Synthetic Construct

<400> SEQUENCE: 118

Leu Ala Arg Arg Arg Leu Asn Val Leu Trp Ala Met Leu Arg Asp
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: Synthetic Construct

<400> SEQUENCE: 119

Leu Asn Val Leu Trp Ala Met Leu Arg Asp His Ala Val Tyr His
1               5                   10                  15

<210> SEQ ID NO 120
<211> LENGTH: 15
<212> TYPE: PRT
<213> ORGANISM: Artificial Sequence
<220> FEATURE:
<223> OTHER INFORMATION: Synthetic Construct

<400> SEQUENCE: 120

Ala Met Leu Arg Asp His Ala Val Tyr His Pro Ala Thr Thr Thr
1               5                   10                  15

<210> SEQ ID NO 121
<211> LENGTH: 14
<212> TYPE: PRT
<213> ORGANISM: Artificial Sequence
<220> FEATURE:
<223> OTHER INFORMATION: Synthetic Construct

<400> SEQUENCE: 121

His Ala Val Tyr His Pro Ala Thr Thr Thr Ala Ala Ala Arg
1               5                   10

<210> SEQ ID NO 122
<211> LENGTH: 15
<212> TYPE: PRT
<213> ORGANISM: Artificial Sequence
```

```
<220> FEATURE:
<223> OTHER INFORMATION: Synthetic Construct

<400> SEQUENCE: 122

Ile Val Gly Gln Thr Tyr Arg Glu Val Glu Val Val Leu Val Asp
1               5                   10                  15

<210> SEQ ID NO 123
<211> LENGTH: 15
<212> TYPE: PRT
<213> ORGANISM: Artificial Sequence
<220> FEATURE:
<223> OTHER INFORMATION: Synthetic Construct

<400> SEQUENCE: 123

Thr Tyr Arg Glu Val Glu Val Val Leu Val Asp Gly Gly Ser Thr
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: Synthetic Construct

<400> SEQUENCE: 124

Glu Val Val Leu Val Asp Gly Gly Ser Thr Asp Arg Thr Leu Asp
1               5                   10                  15

<210> SEQ ID NO 125
<211> LENGTH: 15
<212> TYPE: PRT
<213> ORGANISM: Artificial Sequence
<220> FEATURE:
<223> OTHER INFORMATION: Synthetic Construct

<400> SEQUENCE: 125

Asp Gly Gly Ser Thr Asp Arg Thr Leu Asp Ile Ala Asn Ser Phe
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: Synthetic Construct

<400> SEQUENCE: 126

Asp Arg Thr Leu Asp Ile Ala Asn Ser Phe Arg Pro Glu Leu Gly
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: Synthetic Construct

<400> SEQUENCE: 127

Ile Ala Asn Ser Phe Arg Pro Glu Leu Gly Ser Arg Leu Val Val
1               5                   10                  15

<210> SEQ ID NO 128
<211> LENGTH: 15
<212> TYPE: PRT
<213> ORGANISM: Artificial Sequence
<220> FEATURE:
```

-continued

<223> OTHER INFORMATION: Synthetic Construct

<400> SEQUENCE: 128

Arg Pro Glu Leu Gly Ser Arg Leu Val Val His Ser Gly Pro Asp
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: Synthetic Construct

<400> SEQUENCE: 129

Ser Arg Leu Val Val His Ser Gly Pro Asp Asp Gly Pro Tyr Asp
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: Synthetic Construct

<400> SEQUENCE: 130

His Ser Gly Pro Asp Asp Gly Pro Tyr Asp Ala Met Asn Arg Gly
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: Synthetic Construct

<400> SEQUENCE: 131

Asp Gly Pro Tyr Asp Ala Met Asn Arg Gly Val Gly Val Ala Thr
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: Synthetic Construct

<400> SEQUENCE: 132

Ala Met Asn Arg Gly Val Gly Val Ala Thr Gly Glu Trp Val Leu
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: Synthetic Construct

<400> SEQUENCE: 133

Val Gly Val Ala Thr Gly Glu Trp Val Leu Phe Leu Gly Ala Asp
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: Synthetic Construct

```
<400> SEQUENCE: 134

Gly Glu Trp Val Leu Phe Leu Gly Ala Asp Asp Thr Leu Tyr Glu
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: Synthetic Construct

<400> SEQUENCE: 135

Phe Leu Gly Ala Asp Asp Thr Leu Tyr Glu Pro Thr Thr Leu Ala
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: Synthetic Construct

<400> SEQUENCE: 136

Asp Thr Leu Tyr Glu Pro Thr Thr Leu Ala Gln Val Ala Ala Phe
1               5                   10                  15

<210> SEQ ID NO 137
<211> LENGTH: 15
<212> TYPE: PRT
<213> ORGANISM: Artificial Sequence
<220> FEATURE:
<223> OTHER INFORMATION: Synthetic Construct

<400> SEQUENCE: 137

Pro Thr Thr Leu Ala Gln Val Ala Ala Phe Leu Gly Asp His Ala
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: Synthetic Construct

<400> SEQUENCE: 138

Gln Val Ala Ala Phe Leu Gly Asp His Ala Ala Ser His Leu Val
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: Synthetic Construct

<400> SEQUENCE: 139

Leu Gly Asp His Ala Ala Ser His Leu Val Tyr Gly Asp Val Val
1               5                   10                  15

<210> SEQ ID NO 140
<211> LENGTH: 15
<212> TYPE: PRT
<213> ORGANISM: Artificial Sequence
<220> FEATURE:
<223> OTHER INFORMATION: Synthetic Construct
```

```
<400> SEQUENCE: 140

Ala Ser His Leu Val Tyr Gly Asp Val Val Met Arg Ser Thr Lys
1               5                   10                  15

<210> SEQ ID NO 141
<211> LENGTH: 15
<212> TYPE: PRT
<213> ORGANISM: Artificial Sequence
<220> FEATURE:
<223> OTHER INFORMATION: Synthetic Construct

<400> SEQUENCE: 141

Tyr Gly Asp Val Val Met Arg Ser Thr Lys Ser Arg His Ala Gly
1               5                   10                  15

<210> SEQ ID NO 142
<211> LENGTH: 15
<212> TYPE: PRT
<213> ORGANISM: Artificial Sequence
<220> FEATURE:
<223> OTHER INFORMATION: Synthetic Construct

<400> SEQUENCE: 142

Met Arg Ser Thr Lys Ser Arg His Ala Gly Pro Phe Asp Leu Asp
1               5                   10                  15

<210> SEQ ID NO 143
<211> LENGTH: 17
<212> TYPE: PRT
<213> ORGANISM: Artificial Sequence
<220> FEATURE:
<223> OTHER INFORMATION: Synthetic Construct

<400> SEQUENCE: 143

Ser Arg His Ala Gly Pro Phe Asp Leu Asp Arg Leu Leu Phe Glu Pro
1               5                   10                  15

Phe

<210> SEQ ID NO 144
<211> LENGTH: 16
<212> TYPE: PRT
<213> ORGANISM: Artificial Sequence
<220> FEATURE:
<223> OTHER INFORMATION: Synthetic Construct

<400> SEQUENCE: 144

Asp Leu Asp Arg Leu Leu Phe Glu Thr Asn Leu Cys His Arg Leu Leu
1               5                   10                  15

<210> SEQ ID NO 145
<211> LENGTH: 12
<212> TYPE: PRT
<213> ORGANISM: Artificial Sequence
<220> FEATURE:
<223> OTHER INFORMATION: Synthetic Construct

<400> SEQUENCE: 145

Phe Glu Thr Asn Leu Cys His Gln Ser Ile Phe Tyr
1               5                   10

<210> SEQ ID NO 146
<211> LENGTH: 15
<212> TYPE: PRT
<213> ORGANISM: Artificial Sequence
<220> FEATURE:
<223> OTHER INFORMATION: Synthetic Construct
```

```
<400> SEQUENCE: 146

Thr Asn Leu Cys His Gln Ser Ile Phe Tyr Arg Arg Glu Leu Phe
1               5                   10                  15

<210> SEQ ID NO 147
<211> LENGTH: 15
<212> TYPE: PRT
<213> ORGANISM: Artificial Sequence
<220> FEATURE:
<223> OTHER INFORMATION: Synthetic Construct

<400> SEQUENCE: 147

Gln Ser Ile Phe Tyr Arg Arg Glu Leu Phe Asp Gly Ile Gly Pro
1               5                   10                  15

<210> SEQ ID NO 148
<211> LENGTH: 15
<212> TYPE: PRT
<213> ORGANISM: Artificial Sequence
<220> FEATURE:
<223> OTHER INFORMATION: Synthetic Construct

<400> SEQUENCE: 148

Arg Arg Glu Leu Phe Asp Gly Ile Gly Pro Tyr Asn Leu Arg Tyr
1               5                   10                  15

<210> SEQ ID NO 149
<211> LENGTH: 15
<212> TYPE: PRT
<213> ORGANISM: Artificial Sequence
<220> FEATURE:
<223> OTHER INFORMATION: Synthetic Construct

<400> SEQUENCE: 149

Asp Gly Ile Gly Pro Tyr Asn Leu Arg Tyr Arg Val Trp Ala Asp
1               5                   10                  15

<210> SEQ ID NO 150
<211> LENGTH: 15
<212> TYPE: PRT
<213> ORGANISM: Artificial Sequence
<220> FEATURE:
<223> OTHER INFORMATION: Synthetic Construct

<400> SEQUENCE: 150

Tyr Asn Leu Arg Tyr Arg Val Trp Ala Asp Trp Asp Phe Asn Ile
1               5                   10                  15

<210> SEQ ID NO 151
<211> LENGTH: 15
<212> TYPE: PRT
<213> ORGANISM: Artificial Sequence
<220> FEATURE:
<223> OTHER INFORMATION: Synthetic Construct

<400> SEQUENCE: 151

Arg Val Trp Ala Asp Trp Asp Phe Asn Ile Arg Cys Phe Ser Asn
1               5                   10                  15

<210> SEQ ID NO 152
<211> LENGTH: 15
<212> TYPE: PRT
<213> ORGANISM: Artificial Sequence
<220> FEATURE:
<223> OTHER INFORMATION: Synthetic Construct
```

-continued

```
<400> SEQUENCE: 152

Trp Asp Phe Asn Ile Arg Cys Phe Ser Asn Pro Ala Leu Ile Thr
1               5                   10                  15

<210> SEQ ID NO 153
<211> LENGTH: 15
<212> TYPE: PRT
<213> ORGANISM: Artificial Sequence
<220> FEATURE:
<223> OTHER INFORMATION: Synthetic Construct

<400> SEQUENCE: 153

Arg Cys Phe Ser Asn Pro Ala Leu Ile Thr Arg Tyr Met Asp Val
1               5                   10                  15

<210> SEQ ID NO 154
<211> LENGTH: 15
<212> TYPE: PRT
<213> ORGANISM: Artificial Sequence
<220> FEATURE:
<223> OTHER INFORMATION: Synthetic Construct

<400> SEQUENCE: 154

Pro Ala Leu Ile Thr Arg Tyr Met Asp Val Val Ile Ser Glu Tyr
1               5                   10                  15

<210> SEQ ID NO 155
<211> LENGTH: 15
<212> TYPE: PRT
<213> ORGANISM: Artificial Sequence
<220> FEATURE:
<223> OTHER INFORMATION: Synthetic Construct

<400> SEQUENCE: 155

Arg Tyr Met Asp Val Val Ile Ser Glu Tyr Asn Asp Met Thr Gly
1               5                   10                  15

<210> SEQ ID NO 156
<211> LENGTH: 15
<212> TYPE: PRT
<213> ORGANISM: Artificial Sequence
<220> FEATURE:
<223> OTHER INFORMATION: Synthetic Construct

<400> SEQUENCE: 156

Val Ile Ser Glu Tyr Asn Asp Met Thr Gly Phe Ser Met Arg Gln
1               5                   10                  15

<210> SEQ ID NO 157
<211> LENGTH: 15
<212> TYPE: PRT
<213> ORGANISM: Artificial Sequence
<220> FEATURE:
<223> OTHER INFORMATION: Synthetic Construct

<400> SEQUENCE: 157

Asn Asp Met Thr Gly Phe Ser Met Arg Gln Gly Thr Asp Lys Glu
1               5                   10                  15

<210> SEQ ID NO 158
<211> LENGTH: 15
<212> TYPE: PRT
<213> ORGANISM: Artificial Sequence
<220> FEATURE:
<223> OTHER INFORMATION: Synthetic Construct

<400> SEQUENCE: 158
```

```
Phe Ser Met Arg Gln Gly Thr Asp Lys Glu Phe Arg Lys Arg Leu
1               5                   10                  15
```

<210> SEQ ID NO 159
<211> LENGTH: 15
<212> TYPE: PRT
<213> ORGANISM: Artificial Sequence
<220> FEATURE:
<223> OTHER INFORMATION: Synthetic Construct

<400> SEQUENCE: 159

```
Gly Thr Asp Lys Glu Phe Arg Lys Arg Leu Pro Met Tyr Phe Trp
1               5                   10                  15
```

<210> SEQ ID NO 160
<211> LENGTH: 15
<212> TYPE: PRT
<213> ORGANISM: Artificial Sequence
<220> FEATURE:
<223> OTHER INFORMATION: Synthetic Construct

<400> SEQUENCE: 160

```
Phe Arg Lys Arg Leu Pro Met Tyr Phe Trp Val Ala Gly Trp Glu
1               5                   10                  15
```

<210> SEQ ID NO 161
<211> LENGTH: 15
<212> TYPE: PRT
<213> ORGANISM: Artificial Sequence
<220> FEATURE:
<223> OTHER INFORMATION: Synthetic Construct

<400> SEQUENCE: 161

```
Pro Met Tyr Phe Trp Val Ala Gly Trp Glu Thr Cys Arg Arg Met
1               5                   10                  15
```

<210> SEQ ID NO 162
<211> LENGTH: 15
<212> TYPE: PRT
<213> ORGANISM: Artificial Sequence
<220> FEATURE:
<223> OTHER INFORMATION: Synthetic Construct

<400> SEQUENCE: 162

```
Val Ala Gly Trp Glu Thr Cys Arg Arg Met Leu Ala Phe Leu Lys
1               5                   10                  15
```

<210> SEQ ID NO 163
<211> LENGTH: 15
<212> TYPE: PRT
<213> ORGANISM: Artificial Sequence
<220> FEATURE:
<223> OTHER INFORMATION: Synthetic Construct

<400> SEQUENCE: 163

```
Thr Cys Arg Arg Met Leu Ala Phe Leu Lys Asp Lys Glu Asn Arg
1               5                   10                  15
```

<210> SEQ ID NO 164
<211> LENGTH: 15
<212> TYPE: PRT
<213> ORGANISM: Artificial Sequence
<220> FEATURE:
<223> OTHER INFORMATION: Synthetic Construct

<400> SEQUENCE: 164

```
Leu Ala Phe Leu Lys Asp Lys Glu Asn Arg Arg Leu Ala Leu Arg
1               5                   10                  15

<210> SEQ ID NO 165
<211> LENGTH: 15
<212> TYPE: PRT
<213> ORGANISM: Artificial Sequence
<220> FEATURE:
<223> OTHER INFORMATION: Synthetic Construct

<400> SEQUENCE: 165

Asp Lys Glu Asn Arg Arg Leu Ala Leu Arg Thr Arg Leu Ile Arg
1               5                   10                  15

<210> SEQ ID NO 166
<211> LENGTH: 15
<212> TYPE: PRT
<213> ORGANISM: Artificial Sequence
<220> FEATURE:
<223> OTHER INFORMATION: Synthetic Construct

<400> SEQUENCE: 166

Arg Leu Ala Leu Arg Thr Arg Leu Ile Arg Val Lys Ala Val Ser
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: Synthetic Construct

<400> SEQUENCE: 167

Thr Arg Leu Ile Arg Val Lys Ala Val Ser Lys Glu Arg Ser Ala
1               5                   10                  15
```